(12) United States Patent
Tung et al.

(10) Patent No.: US 7,759,382 B2
(45) Date of Patent: Jul. 20, 2010

(54) ACYLATED AMINO ACID AMIDYL PYRAZOLES AND RELATED COMPOUNDS

(75) Inventors: Jay S. Tung, Belmont, CA (US); Lee H. Latimer, Oakland, CA (US); Jing Wu, Redwood City, CA (US); Albert Garofalo, South San Francisco, CA (US); Michael A. Pleiss, Sunnyvale, CA (US); Darren Dressen, Fremont, CA (US); Ashley Guinn, Santa Monica, CA (US); Scott A. Jenkins, Tucson, AZ (US); Jennifer Sealy, Oakland, CA (US); John Tucker, San Diego, CA (US); David W. G. Wone, Newark, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 721 days.

(21) Appl. No.: 10/559,823

(22) PCT Filed: Jun. 4, 2004

(86) PCT No.: PCT/US2004/018202

§ 371 (c)(1),
(2), (4) Date: Mar. 1, 2007

(87) PCT Pub. No.: WO2005/009344

PCT Pub. Date: Feb. 3, 2005

(65) Prior Publication Data

US 2007/0197624 A1    Aug. 23, 2007

Related U.S. Application Data

(60) Provisional application No. 60/476,369, filed on Jun. 5, 2003.

(51) Int. Cl.
*A61K 31/415* (2006.01)
*C07D 231/10* (2006.01)

(52) U.S. Cl. ............... 514/407; 548/356.1; 548/371.4; 548/371.7; 514/403; 514/406

(58) Field of Classification Search ............ 548/356.1, 548/371.4, 371.7; 514/403, 406, 407
See application file for complete search history.

(56) References Cited

U.S. PATENT DOCUMENTS

| 6,153,652 A | 11/2000 | Wu et al. |
| 6,191,166 B1 | 2/2001 | Audia et al. |
| 6,207,710 B1 | 3/2001 | Audia et al. |
| 6,211,235 B1 | 4/2001 | Wu et al. |
| 2006/0052426 A1 | 3/2006 | Despeyroux et al. |

FOREIGN PATENT DOCUMENTS

| EP | 0308885 A1 | 3/1989 |
| WO | WO99/57098 A2 | 11/1999 |
| WO | WO 99/66934 | 12/1999 |
| WO | WO 00/38618 | 7/2000 |
| WO | WO 00/77030 | 12/2000 |
| WO | WO01/12189 A1 | 2/2001 |
| WO | WO2004/033434 A1 | 4/2004 |

OTHER PUBLICATIONS

Supplementary European Search Report for EP04776373, dated Oct. 16, 2008.

*Primary Examiner*—Golam M Shameem
(74) *Attorney, Agent, or Firm*—Howrey LLP; Viola T. Kung

(57) ABSTRACT

This invention is directed to acylated amino acid amidyl pyrazoles and related compounds of Formula I. The invention is also directed to a pharmaceutical formation comprising such compound or in a pharmaceutically acceptable salt form thereof. The invention is further directed to a method for inhibiting β-amyloid peptide release and/or synthesis, a method for inhibiting γ-secretase activity, and a method for treating neurological disorders associated with β-amyloid peptide production. The method comprises administering to a host a pharmaceutical formulation comprising an effective amount of a compound of Formula I. The compounds of Formula I are useful in the prevention and treatment of Alzheimer's disease.

10 Claims, No Drawings

US 7,759,382 B2

ACYLATED AMINO ACID AMIDYL PYRAZOLES AND RELATED COMPOUNDS

This application is a National Stage of International Application PCT/US2004/018202, filed Jun. 4, 2004, published Feb. 3, 2005, under PCT Article 21(2) in English; which claims the priority of U.S. Provisional Application 60/476,369, filed Jun. 5, 2003. The contents of the above applications are incorporated herein by reference in their entirety.

FIELD OF THE INVENTION

This invention relates to acylated amino acid amidyl pyrazoles and related compounds that inhibit β-amyloid peptide release and/or its synthesis, and, accordingly, have utility in treating Alzheimer's disease.

BACKGROUND OF THE INVENTION

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39-43 amino acids designated the β-amyloid peptide (βAP) or sometimes Aβ, AβP or β/A4. β-Amyloid peptide was first purified and a partial amino acid sequence was provided by Glenner, et al. (Biochem. Biophys. Res. Commun., 120: 885-890) 1984)). β-amyloid peptide is a small fragment of a much larger precursor protein (APP), normally produced by cells in tissues of various animals.

Aβ is derived from cleavage of APP by protease systems, collectively termed secretases. APP is first cleaved by β secretase to yield a β stub, which is then cleaved by γ secretase to yield a β-amyloid fragment that is secreted. β secretase generates the N-terminus of Aβ. γ secretase generates C-terminal fragments ending at position 38, 39, 40, 42, and 43 or generating C-terminal extended precursors that are subsequently truncated to the above polypeptides.

U.S. Pat. No. 6,153,652 discloses N-(aryl/heteroaryl/alkyacetyl)amino acid amides, which inhibit β amyloid peptide release and/or its synthesis, and methods for treating Alzheimer's disease with such compounds. U.S. Pat. Nos. 6,191,166 and 6,211,235 each discloses a class of compounds, which inhibit β amyloid peptide release and/or its synthesis, and methods for treating Alzheimer's disease with such compounds. WO 00/38618 discloses succinoylaminobenzodiazepines and related structures and methods for inhibiting γ-secretase activity. WO 00/77030 discloses statine-derived tetrapeptide inhibitors of beta-secretase. WO 99/66934 discloses certain cyclic amino acid compounds that inhibit β-amyloid peptide release and/or its synthesis and methods for treating Alzheimer's disease with such compounds.

Despite the progress which has been made in understanding the underlying mechanisms of AD and other β-amyloid peptide related diseases, there remains a need to develop methods and compositions for treatment of the disease. The treatment methods could be based on drugs that are capable of inhibiting β-amyloid peptide release and/or its synthesis in vivo. Methods of treatment could target the formation of Aβ through the enzymes involved in the proteolytic processing of β-amyloid precursor protein. Compounds that inhibit γ-secretase activity, either directly or indirectly, control the production of AP. Such inhibition of γ secretase could thereby reduce production of Aβ, which, thereby, reduces or prevents the neurological disorders associated with β-amyloid peptide.

SUMMARY OF THE INVENTION

This invention is directed to a class of compounds that inhibit β-amyloid peptide release and/or its synthesis. The class of compounds having the described properties are defined by formula I below:

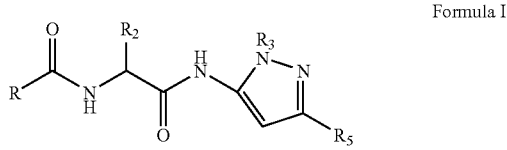

Formula I

The present invention is also directed to a pharmaceutical formation comprising such compound in a pharmaceutically acceptable salt form or prodrug thereof.

The present invention is directed to a method for inhibiting β-amyloid peptide release and/or synthesis and a method for inhibiting γ-secretase activity. The present invention is also directed to a method for treating neurological disorders associated with β-amyloid peptide production. The method comprises the steps of administering to a host a pharmaceutical formulation comprising an effective amount of a compound of Formula I. The compounds of Formula I are useful in the prevention of AD in patients susceptible to AD and/or in the treatment of patients with AD.

DETAILED DESCRIPTION OF THE INVENTION

This invention is directed to compounds that inhibit β-amyloid peptide release and/or its synthesis.

The class of compounds having the described properties is defined by Formula I below:

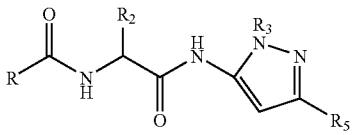

Formula I or a pharmaceutically acceptable salt thereof, wherein R is substituted or unsubstituted aryl, cycloalkyl, heterocyclic, alkoxy, cycloalkoxy, aryloxy, heteroaryloxy, alkylamino, cycloalkylamino, arylamino, heteroarylamino; or R is

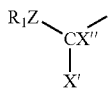

wherein X' and X" are each independently hydrogen, hydroxy or fluoro, provided when one of X' and X" is fluoro, the other is not hydroxy; or X' and X" together form an oxo group, Z is selected from the group consisting of alkyl, nitrogen, oxygen, sulfur and a bond covalently linking $R_1$ to —CX'X"—

$R_1$ is selected from the group consisting of hydrogen, substituted or unsubstituted alkyl, alkenyl, aryl, cycloalkyl, cycloalkenyl, heteroaryl, and heterocyclic;

$R_2$ is selected from the group consisting of hydrogen, $C_1$-$C_4$ alkyl, alkylalkoxy, alkylthioalkoxy, —$COOR_{2a}$, and —$COR_{2a}$ wherein $R_{2a}$ is hydrogen, $C_{1-4}$ alkyl (such as ethyl), cycloalkyl, or heterocycle (such as pyrrolidinyl);

$R_3$ is H, substituted or unsubstituted, linear-, branched- or cyclo-alkyl or substituted or unsubstituted phenyl;

$R_5$ is —Y—$R_6$, wherein Y is substituted or unsubstituted alkyl, alkenyl, aryl, cycloalkyl, cycloalkenyl, heteroaryl, heterocyclic, or a bond; and $R_6$ is substituted or unsubstituted aryl, heteroaryl, cycloalkyl, heterocycloalkyl, aryloxide, heteroaryl N-oxide, or arylsulfide;

provided when Y is a bond, then either $R_6$ is cycloalkyl, or $R_2$ is alkylalkoxy or alkylthioalkoxy.

Examples of $R_5$ include phenylmethyl, benzhydryl, 1-phenylcyclopropyl, 1-phenylcyclopentyl, 1-phenylcyclohexyl, styryl, 1,1-dimethyl-1-phenylethyl, 1,1-dimethylbutyl, 2,2-dimethyl-2-phenylethyl, 4-phenyltetrahydropyran-4-yl, 1-phenylethyl, 3-phenylpropyl, 1-methyl-1-(phenylthio) ethyl, 1-cyclohexyl-1-methylethyl, 1-methyl-4-phenylpiperidin-4-yl, 1-cyclopropyl-4-phenylpiperidin-4-yl.

A preferred $R_2$ is methyl. A preferred $R_3$ is H or t-butyl. A preferred R is ($R_1$Z)CX'X", wherein said X' is H or OH, X" is H, Z is a bond, and $R_1$ is alkyl, substituted alkyl, aryl, or substituted aryl such as 3,5-difluorophenyl.

Preferred compounds of Formula I are shown as Formula II:

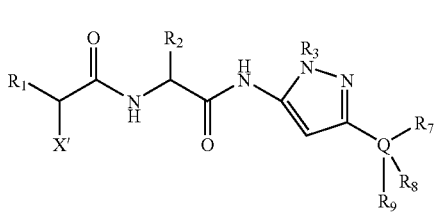

Formula II wherein $R_1$ is alkyl, substituted alkyl, aryl, or substituted aryl; X' is H or OH; $R_2$ is $CH_3$; $R_3$ is H, or t-butyl (with H being more preferred); Q is carbon; $R_7$ is aryl, substituted aryl, or U-Aryl, wherein U is O or $CH_2$; and $R_8$ and $R_9$ are independently H, or alkyl (such as $CH_3$), or $R_8$, $R_9$ and Q taken together form a cycloalkyl or heterocycloalkyl.

DEFINITION

The term "β-amyloid peptide" refers to a 39-43 amino acid peptide having a molecular weight of about 4.2 kD, which peptide is substantially homologous to the form of the protein described by Glenner, et al. (*Biochem. Biophys. Res. Commun.*, 120:885-890 (1984)) including mutations and post-translational modifications of the normal β-amyloid peptide. β-amyloid peptide is approximately a 39-43 amino acid fragment of a large membrane-spanning glycoprotein, referred to as the β-amyloid precursor protein (APP). Its 43-amino acid sequence is disclosed in U.S. Pat. No. 6,153,652.

"Alkyl" refers to monovalent alkyl groups preferably having from 1 to 10 carbon atoms and more preferably 1 to 6 carbon atoms. This term is exemplified by groups such as methyl, ethyl, n-propyl, iso-propyl, n-butyl, iso-butyl, n-hexyl, and the like. The use of the notation "C" followed by a numerical range preceding a defined term, indicates a range of atoms intended to add further to the definition. e.g., ($C_{1-6}$) alkyl defines an alkyl group having from 1 to 6 (inclusive) carbon atoms.

Unless otherwise constrained by a limitation of the alkyl group, alkyl can optionally be substituted with from 1 to 3 substitutents selected from the group consisting of hydroxy, ($C_{1-3}$) alkoxy, ($C_{1-3}$)alkylthioxy, halo, acyl, acyloxy, amino, aminoacyl, acylamino, alkoxycarbonyl, carboxyl, cyano, phenyl optionally substituted with 1 to 2 halo atoms and trifluoromethyl.

"Alkoxy" refers to the group "alkyl-O—" where alkyl is as defined herein. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkylalkoxy" refers to the group "-alkylene-O-alkyl," substituted or unsubstituted, which includes by way of example, methylenemethoxy (—$CH_2OCH_3$), ethylenemethoxy (—$CH_2CH_2OCH_3$), methylene-iso-propoxy (—$CH_2$—O—$CH(CH_3)_2$) and the like.

"Alkylthioalkoxy" refers to the group "-alkylene-S-alkyl," substituted or unsubstituted, which includes by way of example, methylenethiomethoxy (—$CH_2SCH_3$), ethylenethiomethoxy (—$CH_2CH_2SCH_3$), methylene-iso-thiopropoxy (—$CH_2$—S—$CH(CH_3)_2$) and the like.

"Alkenyl" refers to alkenyl groups preferably having from 2 to 10 carbon atoms and more preferably 2 to 6 carbon atoms and having at least 1 and preferably from 1-2 sites of alkenyl unsaturation. Preferred alkenyl groups include ethenyl (—CH=CH$_2$), allyl or n-2 propenyl (—CH$_2$CH=CH$_2$), isopropenyl (—C(CH$_3$)=CH$_2$), 2-butenyl (—CH$_2$CH=CHCH$_3$) and the like.

"Alkynyl" refers to alkynyl groups preferably having from 2 to 10 carbon atoms and more preferably 2 to 6 carbon atoms and having at least 1 and preferably from 1-2 sites of alkynyl unsaturation. Preferred alkynyl groups include ethynyl (—C≡CH), propargyl (—CH$_2$—C≡CH) and the like.

"Acyl" refers to the groups alkyl-C(O)—, aryl-C(O)—, and heteroaryl-C(O)— where alkyl, aryl and heteroaryl are as defined herein.

"Acylamino" refers to the group —C(O)NRR where each R is independently hydrogen or alkyl where alkyl is as defined herein.

"Aminoacyl" refers to the group —NRC(O)R where each R is independently hydrogen or alkyl where alkyl is as defined herein.

"Acyloxy" refers to the groups alkyl-C(O)O—, aryl-C(O)O—, heteroaryl-C(O)O—, and heterocyclic-C(O)O— where alkyl, aryl, heteroaryl and heterocyclic are as defined herein.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

"Arylalkyl" refers to aryl-alkyl- groups preferably having from 1 to 6 carbon atoms in the alkyl moiety and from 6 to 10 carbon atoms in the aryl moiety. Such arylalkyl groups are exemplified by benzyl, phenethyl and the like.

"Arylalkenyl" refers to aryl-alkenyl- groups preferably having from 1 to 6 carbon atoms in the alkenyl moiety and from 6 to 10 carbon atoms in the aryl moiety.

"Arylalkynyl" refers to aryl-alkynyl- groups preferably having from 1 to 6 carbon atoms in the alkynyl moiety and from 6 to 10 carbon atoms in the aryl moiety.

"Aryloxy" refers to the group aryl-O— wherein the aryl group is as defined above including optionally substituted aryl groups as also defined above.

The terms "amide" and "amido" refer to a functional group containing a carbon atom double-bonded to an oxygen atom and additionally singly bonded to a nitrogen atom [—C(O)—N]. "Primary" amide describes an unsubstituted amide group [—C(O)—NH$_2$]. "Secondary" and "tertiary" amides are amides in which nitrogen is substituted with one and two non-hydrogen groups respectively.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Cycloalkenyl" refers to cyclic alkenyl groups of from 4 to 8 carbon atoms having a single cyclic ring and at least one point of internal unsaturation which can be optionally substituted with from 1 to 3 alkyl groups. Examples of suitable cycloalkenyl groups include, for instance, cyclobut-2-phenyl, cyclopent-3-phenyl, cyclooct-3-phenyl and the like.

"Halo" or "halogen" refers to fluoro, chloro, bromo and iodo and preferably is either chloro or fluoro.

"Heteroaryl" refers to a monovalent aromatic carbocyclic group of from 1 to 10 carbon atoms and 1 to 4 heteroatoms selected from oxygen, nitrogen and sulfur within the ring. Such heteroaryl groups can have a single ring (e.g., pyridyl or furyl) or multiple condensed rings (e.g., indolizinyl or benzothienyl).

"Heterocycle" or "heterocyclic" refers to a saturated or unsaturated group having a single ring or multiple condensed rings, from 1 to 8 carbon atoms and from 1 to 4 hetero atoms selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Preferred heterocycles include piperidinyl, pyrrolidinyl and tetrahydrofuryl.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

"Thiol" refers to the group —SH.

"Thioalkoxy" refers to the group —S-alkyl.

"Thioaryloxy" refers to the group aryl-S— wherein the aryl group is as defined above including optionally substituted aryl groups as also defined above.

Unless otherwise constrained by the definition for the individual substitutent, aryl, cycloalkyl, heteroaryl, and heterocyclic groups can be optionally substituted with 1 to 3 substitutents selected from the group consisting of alkyl, alkenyl, aryl, cycloalkyl, cycloalkenyl, heteroaryl, heterocyclic, alkaryl, alkcycloalkyl, alkcycloalkenyl, alkheteroaryl, alkheterocyclic, alkoxy, aryloxy, halo, nitro, hydroxy, amino, acyl, acyloxy, aminoacyl, acylamino, carboxy, cyano, alkoxycarbonyl, thioalkoxy, thioaryloxy and the like. Preferred substitutents include alkyl, alkoxy, halo, cyano, nitro, hydroxy, trihalomethyl, thioalkoxy, and amino.

"Pharmaceutically acceptable salt" refers to pharmaceutically acceptable salts of a compound of Formula I which salts are derived from a variety of organic and inorganic counter ions well known in the art and include, by way of example only, lithium, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Pharmaceutical Formulations

When employed as pharmaceuticals, the compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions that contain, as the active ingredient, one or more of the compounds of Formula I, or a pharmaceutically accepted form or prodrug thereof, associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 1 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carriers.

The active compound is effective over a wide dosage range and is generally administered in a pharmaceutically effective amount. The amount of the compound actually administered will be determined by a physician, in view of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention can be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, herein incorporated by reference. Such patches may be constructed for continuous, pulsatile, or on demand delivery of pharmaceutical agents.

Often, it is desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mace Publishing Company, Philadelphia, Pa., 17th ed. (1985).

Utility

The present invention is directed to a method for inhibiting β-amyloid peptide release and/or synthesis in a cell and a method for inhibiting γ-secretase activity. The invention is also directed to a method for preventing or treating of neurological disorders associated with β-amyloid peptide production. The method comprises the steps of administering to a host in need of such treatment a pharmaceutical formulation comprising a therapeutically effective amount of a compound of Formula I. The compounds of Formula I are useful in the prevention of AD in patients susceptible to AD and/or in the treatment of patients with AD.

Aβ production has been implicated in the pathology of Alzheimer's Disease (AD). The compounds of the present invention have utility for the prevention and treatment of AD by inhibiting Aβ production. Methods of treatment target formation of Aβ production through the enzymes involved in the proteolytic processing of β-amyloid precursor protein. Compounds that inhibit γ secretase activity, either directly or indirectly, control the production of Aβ. Such inhibition of γ secretase reduces production of Aβ, and is expected to reduce or prevent the neurological disorders associated with Aβ such as Alzheimer's Disease.

Compounds of Formula I are expected to possess γ-secretase inhibitory activity or inhibit Aβ production. Cellular screening methods for inhibitors of Aβ production, testing methods for the in vivo suppression of Aβ production, and assays for the detection of secretase activity are known in the art and have been disclosed in many publications, including WO 98/22493 and WO 01/19797, EP 0652009, U.S. Pat. Nos. 5,703,129 5,593,846; 6,211,235 and 6,207,710, all hereby incorporated by reference.

Compounds provided by this invention are useful as standards and reagents in determining the ability of a potential pharmaceutical reagent to inhibit Aβ production. These can be provided in a kit comprising a compound of this invention.

A compound is considered to be active if it has an $IC_{50}$ or $K_i$ value of less than about 100 μM for the inhibition of Aβ production.

Synthesis and Preparation of Compounds Having Formula I

The compounds of the present invention can be prepared in a number of ways known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substitutents which are compatible with the reaction conditions will be readily apparent to one skilled in the art and alternate methods must then be used.

Construction of Acylated Amino Acid Amidyl Pyrazoles.

A variety of substituted acylated amino acid amidyl pyrazoles can be prepared using the corresponding carboxylic acids in this fashion. The following Methods A-f show general methods for preparing acylated amino acid amidyl pyrazoles.

Synthesis of Pyrazoles (Type 8 and 9).

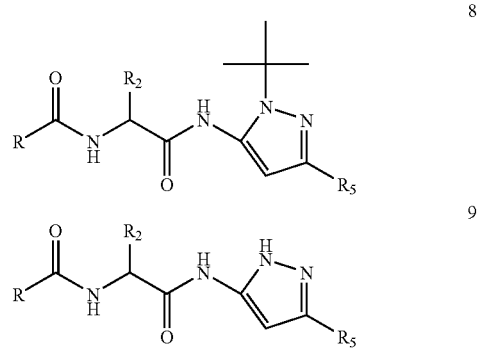

A variety of 5' substituted pyrazoles can be prepared using carboxylic acid (1), amino acids (4, natural and unnatural) and an additional carboxylic acid (7). In some instances, protecting group strategies on R, $R_2$ and/or $R_5$ are required, the methods described in Protective Groups In Organic Synthesis (Theodora W. Greene and Peter G. M. Wuts, Wiley and Sons) were employed to address these cases.

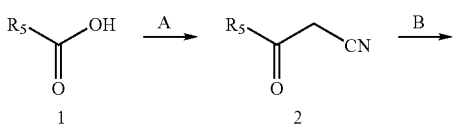

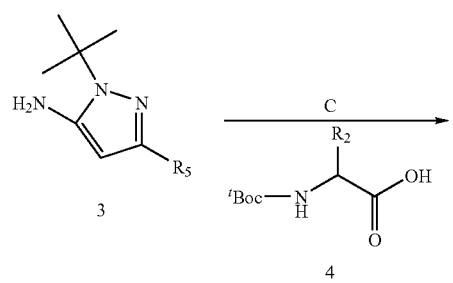

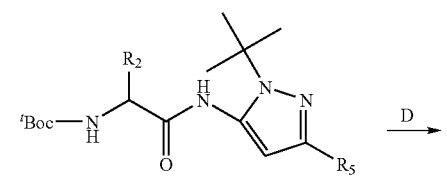

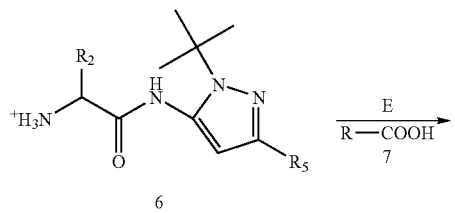

-continued

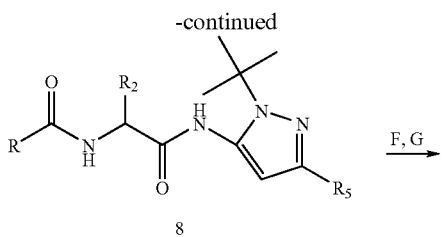

8

F, G →

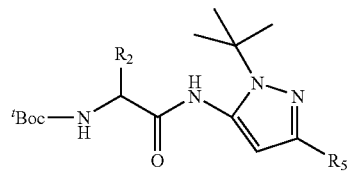

5

Method D

A solution of N-tert-butyl protected pyrazole 5 is stirred in a solution of methylene chloride/trifluoroacetic acid. The volatiles are evaporated off to yield the corresponding salt of the desired amine 6.

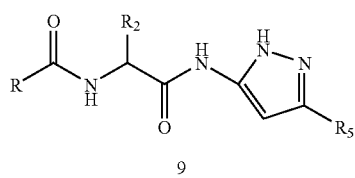

9

Method A

In a dried round bottom flask, a solution of carboxylic acid 1 is prepared. To the reaction solution, N,N'-carbonyldiimidazole is added. In a separate round bottom flask, a solution of cyanoacetic acid is added with isopropylmagnesium chloride. The two reaction mixtures are mixed together and after a time sufficient for reaction, combined with acetic acid to bring to ~pH 5. The crude material is further processed to give a yellowish oil as ketonitrile product 2.

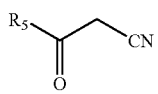

2

Method B

A solution of ketonitrile 2, tert-butylhydrazine, and triethylamine in absolute ethanol is refluxed for a time sufficient for reaction to proceed. After cooling to room temperature, the reaction solution is concentrated, extracted with EtOAc, and dried. The residual crude material is flash chromatographed to afford the t-butyl amino pyrazole 3.

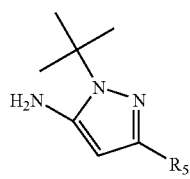

3

Method C

General Procedure for POCl₃ Coupling of t-butyl amino pyrazole 3 with amino acid 4. A solution of 3 and amino acid 4 in suitable solvent is added with POCl₃. The reaction mixture is then extracted, dried, and the solvent removed. Purification of the material affords product 5.

6

Method E

The carboxylic acid 7, amine 6, triethylamine (TEA) and hydroxybenzotriazole hydrate (HOBT) are mixed. The mixture is then added with 1-ethyl-3-(3'-dimethylaminopropyl) carbodiimide hydrochloride (EDCI). The reaction mixture is then purified to yield the desired product 8.

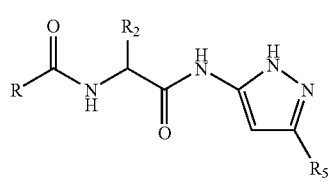

8

Method F

A solution of N-tert-butyl protected pyrazole 8 in formic acid is refluxed then added to saturated NaHCO₃(aq). The quenched solution is extracted, dried, and vacuum filtered. The crude material is chromatographed on silica to give the t-butyl deprotected product 9. In the event that functionalities on R, R₂ or R₅ have been formylated as a result of Method F, the resulting formyl group is removed.

9

EXAMPLES

Examples A-H show methods for preparing acylated amino acid amidyl pyrazoles.

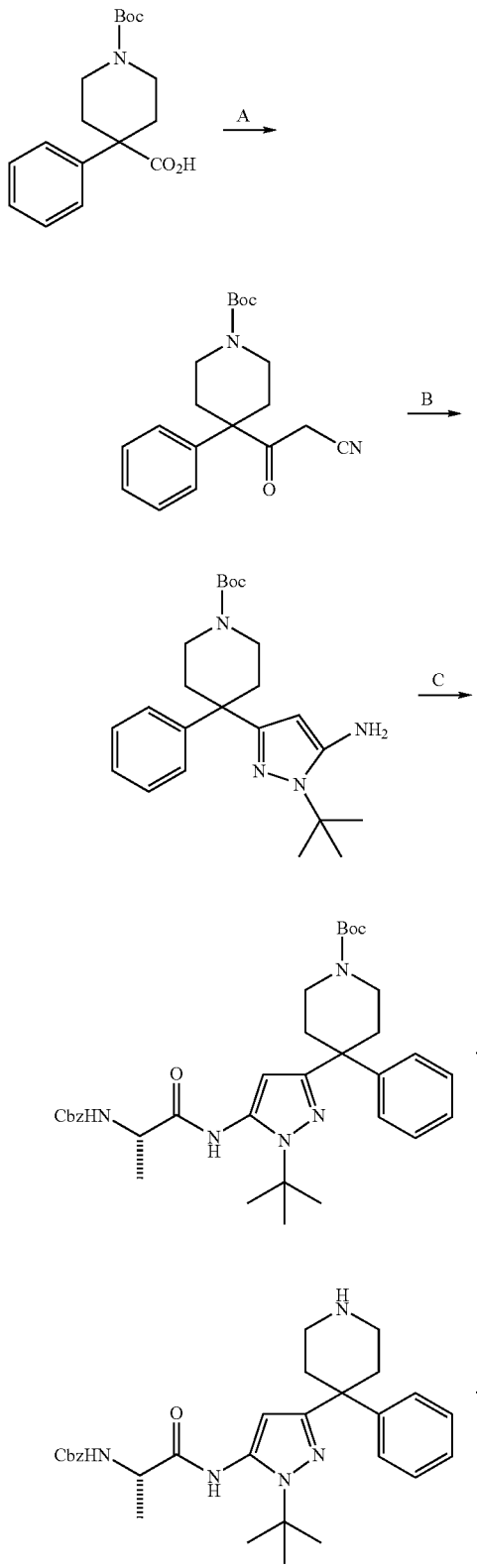

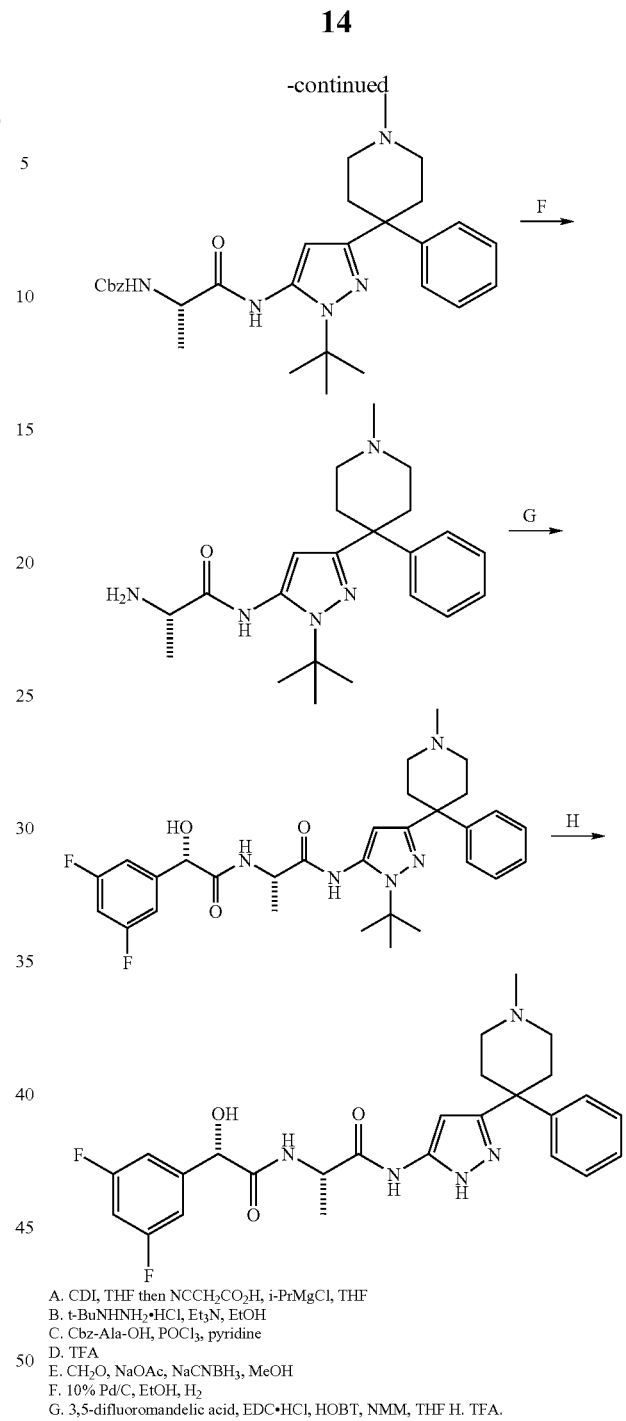

A. CDI, THF then NCCH$_2$CO$_2$H, i-PrMgCl, THF
B. t-BuNHNH$_2$·HCl, Et$_3$N, EtOH
C. Cbz-Ala-OH, POCl$_3$, pyridine
D. TFA
E. CH$_2$O, NaOAc, NaCNBH$_3$, MeOH
F. 10% Pd/C, EtOH, H$_2$
G. 3,5-difluoromandelic acid, EDC·HCl, HOBT, NMM, THF H. TFA.

Example A 4-(2-Cyanoacetyl)-4-phenylpiperidine-1-carboxylic acid tert-butyl ester. A solution of 2.52 g (30 mmol) of cyanoacetic acid in 80 mL of dry THF was stirred at −78° C. as 24.6 mL (49.2 mmol) of 2.0 M i-PrMgCl in THF was added. After 1 h, a solution of 3.00 g (10 mmol) 1-tert-butoxycarbonyl-4-phenylpiperidine-4-carboxylic acid (Maybridge, cat. no. JFD 01929) and 1.93 g (12 mmol) of 1,1'-carbonyldiimidazole in 20 mL of THF was added. The reaction mixture was allowed to warm to rt. After 16 h, the mixture was poured into 300 mL of water and the pH lowered to 4 with conc. AcOH. The mixture was then extracted with EtOAc, dried over MgSO$_4$ and concentrated. Purification on silica gel using 1:1 EtOAc-hexanes as eluant afforded 4-(2-cyanoacetyl)-4-phenylpiperidine-1-carboxylic acid tert-butyl ester.

Example B 4-(5-Amino-1-tert-butyl-1H-pyrazol-3-yl)-4-phenylpiperidine-1-carboxylic acid tert-butyl ester. A solution of 1.66 g (5.0 mmol) of 4-(2-cyanoacetyl)-4-phenylpiperidine-1-carboxylic acid tert-butyl ester, 2.20 mL (16 mmol) of $Et_3N$ and 2.00 g (16 mmol) of tert-butylhydrazine hydrochloride in 20 mL of absolute EtOH was heated to 100° C. in a sealed tube. After 64 h, the reaction mixture was cooled to rt and concentrated. Purification on silica gel using 30:70 EtOAc-hexanes as eluant afforded 4-(5-amino-1-tert-butyl-1H-pyrazol-3-yl)-4-phenylpiperidine-1-carboxylic acid tert-butyl ester.

Example C

4-[5-(2-Benzyloxycarbonylamino-propionylamino)-1-tert-butyl-1H-pyrazol-3-yl]-4-phenylpiperidine-1-carboxylic acid tert-butyl ester. A solution of 0.68 g (1.7 mmol) of 4-(5-amino-1-tert-butyl-1H-pyrazol-3-yl)-4-phenylpiperidine-1-carboxylic acid tert-butyl ester and 0.39 g (1.7 mmol) of carbobenzyloxy-L-alanine in 9.0 mL of dry pyridine was stirred at −10° C. as 0.18 mL (1.9 mmol) of $POCl_3$ was added. After 25 min, the reaction mixture was poured into 1M HCl and extracted with EtOAc. The organic layer washed with sat. aq. $NaHCO_3$, dried over $MgSO_4$ and concentrated. Purification on silica gel using 50:50 EtOAc-hexanes as eluant afforded 4-[5-(2-benzyloxycarbonylamino-propionylamino)-1-tert-butyl-1H-pyrazol-3-yl]-4-phenylpiperidine-1-carboxylic acid tert-butyl ester.

Example D

{1-[2-tert-Butyl-5-(4-phenylpiperidin-4-yl)-2H-pyrazol-3-ylcarbamoyl]ethyl}carbamic acid benzyl ester. A solution of 0.54 g (0.9 mmol) of 4-[5-(2-benzyloxycarbonylamino-propionylamino)-1-tert-butyl-1H-pyrazol-3-yl]-4-phenylpiperidine-1-carboxylic acid tert-butyl ester in 4.0 mL of neat trifluoroacetic acid was stirred at rt for 15 min. The reaction mixture was then poured into sat. aq. $NaHCO_3$ and extracted with EtOAc. The organic layer was dried over $MgSO_4$ and concentrated to afford {1-[2-tert-butyl-5-(4-phenylpiperidin-4-yl)-2H-pyrazol-3-ylcarbamoyl]ethyl}-carbamic acid benzyl ester which was used without further purification.

Example E

{1-[2-tert-Butyl-5-(1-methyl-4-phenylpiperidin-4-yl)-2H-pyrazol-3-ylcarbamoyl]ethyl}carbamic acid benzyl ester. A solution of 0.67 g (1.3 mmol) of {1-[2-tert-butyl-5-(4-phenylpiperidin-4-yl)-2H-pyrazol-3-ylcarbamoyl] ethyl}carbamic acid benzyl ester, 0.33 mL (4.0 mmol) of 37% aq. formaldehyde, 0.33 g (4.0 mmol) of NaOAc and 0.27 g (4.3 mmol) of $NaCNBH_3$ in 10 mL of MeOH was stirred at rt. After 16 h, the reaction mixture was concentrated and extracted with water and EtOAc. The organic layer was dried over $MgSO_4$, and concentrated. Purification on silica gel using 4% $Et_3N$-MeOH as eluant afforded {1-[2-tert-butyl-5-(1-methyl-4-phenylpiperidin-4-yl)-2H-pyrazol-3-ylcarbamoyl]ethyl}carbamic acid benzyl ester.

Example F

2-Amino-N-[2-tert-butyl-5-(1-methyl-4-phenylpiperidin-4-yl)-2H-pyrazol-3-yl]propionamide. A suspension of 0.36 g (0.7 mmol) of {1-[2-tert-butyl-5-(1-methyl-4-phenylpiperidin-4-yl)-2H-pyrazol-3-ylcarbamoyl]ethyl}carbamic acid benzyl ester and 0.36 g of 10% Pd/C in 5.0 mL of absolute EtOH was agitated under 30 psi $H_2$ for 16 h. The reaction mixture was filtered through Celite and 0.36 g of fresh 10% Pd/C was added to the filtrate which was again agitated under 30 psi $H_2$ for 16 h. This process was repeated once more and, after a final filtration, the filtrate was concentrated. Purification on silica gel using 4% $Et_3N$-MeOH as eluant afforded 2-amino-N-[2-tert-butyl-5-(1-methyl-4-phenylpiperidin-4-yl)-2H-pyrazol-3-yl]propionamide.

Example G

N-[2-tert-Butyl-5-(1-methyl-4-phenylpiperidin-4-yl)-2H-pyrazol-3-yl]-2-[2-(3,5-difluorophenyl)-2-hydroxyacetylamino]propionamide. A solution of 0.14 g (0.4 mmol) of 2-amino-N-[2-tert-butyl-5-(1-methyl-4-phenylpiperidin-4-yl)-2H-pyrazol-3-yl]propionamide and 0.08 g (0.4 mmol) of (S)-3,5-difluoromandelic acid (Garofalo, et al. *Bioorg. Med. Chem. Lett.* 2002, 12, 3051) in 5.0 mL of THF was stirred at rt as 0.06 g (0.4 mmol) of HOBT and 0.08 mL (0.7 mmol) of NMM was added followed by 0.90 g (0.5 mmol) of EDC.HCl. After 16 h, the reaction was quenched with 1M HCl and extracted with EtOAc. The organic layer washed with sat. aq. $NaHCO_3$, dried over $MgSO_4$ and concentrated. Purification on silica gel using 4% $Et_3N$-MeOH as eluant afforded N-[2-tert-butyl-5-(1-methyl-4-phenylpiperidin-4-yl)-2H-pyrazol-3-yl]-2-[2-(3,5-difluorophenyl)-2-hydroxyacetylamino]propionamide.

Example H

2-[2-(3,5-Difluorophenyl)-2-hydroxyacetylamino]-N-[5-(1-methyl-4-phenylpiperidin-4-yl)-2H-pyrazol-3-yl]propionamide. A solution of 0.04 g (0.1 mmol) of N-[2-tert-butyl-5-(1-methyl-4-phenylpiperidin-4-yl)-2H-pyrazol-3-yl]-2-[2-(3,5-difluorophenyl)-2-hydroxyacetylamino] propionamide in 2.0 mL of neat trifluoroacetic acid was refluxed for 15 min. The reaction mixture was then cooled to rt, quenched with sat. aq. $NaHCO_3$ and extracted with EtOAc. The organic layer was dried over $Na_2SO_4$ and concentrated. Purification on silica gel afforded 2-[2-(3,5-difluorophenyl)-2-hydroxyacetylamino]-N-[5-(1-methyl-4 phenylpiperidin-4-yl)-2H-pyrazol-3-yl]propionamide.

Methods A-E or A-F were utilized to prepared the following compounds (Examples 1-107).

Example 1

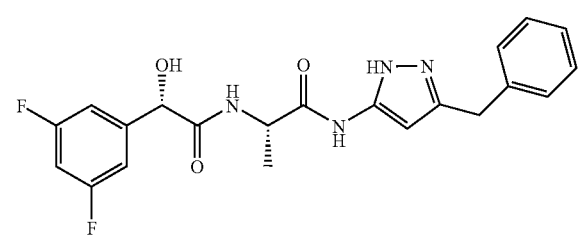

MS 415.0 (M+H), 436.8 (M+Na), 452.6 (M+K).

Anal Calcd for $C_{21}H_{20}F_2N_4O_3$: C, 60.87; H, 4.86; N, 13.52. Found: C, 60.73; H, 4.73; N, 13.28.

¹H NMR (CDCl₃, 300 MHz) δ 11.97 (s, 1H), 7.99 (d, J=9.3 Hz, 1H), 7.21 (m, 5H), 7.09 (d, J=6.1 Hz, 2H), 6.79 (m, 1H), 6.37 (s, 1H), 5.11 (s, 1H), 4.74 (m, 1H), 3.85 (m, 2H), 1.35 (d, J=6.6 Hz, 3H).

Example 2

MS 415.2 (M+H), 436.8 (M+Na).

Anal Calcd for C₂₁H₂₀F₂N₄O₃·¼H₂O: C, 60.21; H, 4.93; N, 13.57. Found: C, 60.24; H, 4.76; N, 13.31.

¹H NMR (CDCl₃, 300 MHz) δ 11.82 (s, 1H), 8.03 (d, J=9.3 Hz, 1H), 7.23 (m, 5H), 6.95 (d, J=6.0 Hz, 2H), 6.57 (m, 1H), 6.21 (s, 1H), 5.16 (s, 1H), 4.87 (m, 1H), 3.84 (m, 2H), 1.41 (d, J=6.6 Hz, 3H).

Example 3

MS 440.8 (M+H), 463.2 (M+Na).

Anal Calcd for C₂₃H₂₂F₂N₄O₃: C, 62.72; H, 5.03; N, 12.72. Found: C, 62.69; H, 5.03; N, 12.68.

¹H NMR (CDCl₃, 300 MHz) δ 11.55 (s, 1H), 11.33 (s(br), 1H), 7.70 (d, J=9.9 Hz, 1H), 7.23 (m, 5H), 7.04 (d, J=7.1 Hz, 2H), 6.76 (t, J=8.2 Hz, 1H), 6.30 (s, 1H), 5.39 (s(br), 1H), 4.71 (m, 1H), 1.33 (m, 7H).

Example 4

MS 469.3 (M+H), 491.3 (M+Na).

Anal Calcd for C₂₅H₂₆F₂N₄O₃: C, 64.09; H, 5.59; N, 11.96. Found: C, 64.06; H, 5.52; N, 11.66.

¹H NMR (CDCl₃, 300 MHz) δ 12.01 (s, 1H), 11.75 (s(br), 1H), 7.84 (d, J=9.3 Hz, 1H), 7.18 (m, 7H), 6.81 (t, J=8.8 Hz, 1H), 6.43 (s, 1H), 5.95 (s(br), 1H), 5.14 (s, 1H), 4.73 (m, 1H), 2.35 (m, 2H), 2.14 (m, 2H), 1.65 (m, 4H), 1.41 (d, J=6.6 Hz, 3H).

Example 5

MS 477.0 (M+H).

Anal Calcd for C₂₃H₂₃ClF₂N₄O₃: C, 57.93; H, 4.86; N, 11.75. Found: C, 57.68; H, 4.92; N, 11.83.

¹H NMR (CDCl₃, 300 MHz) δ 11.75 (s(br), 1H), 7.75 (d, J=9.3 Hz, 1H), 7.16 (m, 4H), 7.02 (d, J=6.0 Hz, 2H), 6.77 (t, J=8.8 Hz, 1H), 6.50 (s, 1H), 5.08 (s, 1H), 4.74 (m, 1H), 1.64 (s, 6H), 1.43 (d, J=6.6 Hz, 3H).

Example 6

MS 488.3 (M+H), 510.1 (M+Na).

Anal Calcd for C₂₃H₂₃F₂N₅O₅·H₂O: C, 55.64; H, 4.87; N, 14.11. Found: C, 55.60; H, 4.82; N, 13.88.

¹H NMR (CDCl₃, 300 MHz) δ 12.14 (s(br), 1H), 12.03 (s(br), 1H), 8.04 (d, J=8.9 Hz, 2H), 7.95 (d, J=8.2 Hz, 1H), 7.33 (d, J=8.8 Hz, 2H), 7.01 (d, J=6.0 Hz, 2H), 6.77 (m, 1H), 5.98 (s(br), 1H), 5.11 (s, 1H), 4.74 (m, 1H), 1.68 (s, 3H), 1.66 (s, 3H), 1.44 (d, J=6.6 Hz, 3M).

Example 7

MS 505.3 (M+H), 527.1 (M+Na).

Anal Calcd for C₂₈H₂₆F₂N₄O₃·¾H₂O: C, 64.92; H, 5.35; N, 10.81. Found: C, 64.94; H, 5.24; N, 10.81.

¹H NMR (CD₃OD, 300 MHz) δ 7.24 (m, 6H), 7.09 (m, 6H), 6.83 (m, 1H), 6.13 (s, 1H), 5.04 (s, 1H), 4.46 (m, 1H), 2.10 (s, 3H), 1.36 (d, J=7.14, 3H).

Example 8

MS 491.1 (M+H), 513.1 (M+Na).
Anal Calcd for C₂₇H₂₄F₂N₄O₃: C, 66.11; H, 4.93; N, 11.42. Found: C, 65.79; H, 5.22; N, 11.25.
¹H NMR (CDCl₃, 300 MHz) δ 7.74 (d, J=9.3 Hz, 1H), 7.21 (m, 10H), 6.89 (d, J=6.0 Hz, 2H), 6.73 (m, 1H), 6.38 (s, 1H), 5.44 (s, 1H), 4.91 (s, 1H), 4.68 (m, 1H), 1.33 (d, J=7.1 Hz, 3H).

Example 9

MS 427.2 (M+H), 449.2 (M+Na).
Anal Calcd for C₂₂H₂₀F₂N₄O₃·¾H₂O: C, 60.06; H, 4.93; N, 12.74. Found: C, 60.27; H, 4.80; N, 12.83.
¹H NMR (CDCl₃, 300 MHz) δ 12.10 (s, 1H), 7.91 (d, J=9.9 Hz, 1H), 7.32 (m, 5H), 7.17 (d, J=6.0 Hz, 2H), 7.00 (d, J=7.0 Hz, 1H), 6.72 (m, 2H), 6.62 (s, 1H), 5.67 (s(br), 1H), 5.20 (s, 1H), 4.87 (m, 1H), 1.44 (d, J=6.6 Hz, 3H).

Example 10

A solution of 90480 (0.74 mmole) in 15 mL of absolute EtOH was prepared. To the solution, was added 0.32 g of 10% Pd on carbon. The reaction mixture was stirred under a balloon of H₂ for 1 hr. The reaction mixture was filtered through a bed of celite on a fritted filter. The filtrate was concentrated by rotary evaporation. The crude material was flash chromatographed on silica using 10% MeOH/CH₂Cl₂ as eluant to afford the reduced product 90603 (70%).
MS 457.9 (M+H), 479.5 (M+Na).

Anal Calcd for C₂₃H₂₅F₂N₅O₃·⅝H₂O: C, 57.55; H, 5.77; N, 14.59. Found: C, 57.33; H, 5.41; N, 14.26.
¹H NMR (CDCl₃, 300 MHz) δ 11.81 (s, 1H), 7.84 (d, J=9.3 Hz, 1H), 6.95 (m, 2H), 6.71 (m, 1H), 6.53 (m, 3H), 5.80 (s(br), 1H), 4.74 (m, 2H), 3.68 (s(br), 1H), 1.61 (s, 3H), 1.57 (s, 3H), 1.36 (d, J=6.6 Hz, 3H).

Example 11

A solution of 0.21 mmole (1.0 eq.) of 90603 in 1 mL of pyridine was prepared. To the solution, was added 0.53 mmole (2.5 eq.) of acetic anhydride. After stirring the solution for 3.5 days at rt, it was poured into 25 mL of 2 M HCl. The solution was extracted with EtOAc (3×40 mL). The combined organic layers were dried over Na₂SO₄ and vacuum filtered. The filtrate was rotary evaporated. The residual solid was dissolved in 5 mL of MeOH and 0.33 mmole (2 eq.) of LiOH was added to remove undesired acylation of the hydroxyl group. The mixture was stirred at rt for 20 min and rotary evaporated. The solid was dissolved in 15 mL of H₂O. The aqueous layer was extracted with EtOAc (3×40 mL). The combined organic extracts were dried over Na₂SO₄ and vacuum filtered. The filtrate was rotary evaporated. The crude material was flash chromatographed on silica using 10% MeOH/CH₂Cl₂ as eluant to give acylated product 91493 (50%).
MS 499.5 (M+H), 521.3 (M+Na).
Anal Calcd for C₂₅H₂₇F₂N₅O₄·½H₂O: C, 57.03; H, 5.74; N, 13.30. Found: C, 57.03; H, 5.41; N, 12.98.
¹H NMR (CD₃OD, 300 MHz) δ 7.74 (d, J=6.6 Hz, 2H), 7.22 (d, J=6.6 Hz, 2H), 7.14 (d, J=7.1 Hz, 2H), 6.90 (m, 1H), 6.46 (s(br), 1H), 5.11 (s, 1H), 4.55 (m, 1H), 2.12 (m, 3H), 1.70 (s, 6H), 1.44 (d, J=5.5 Hz, 3H).

Example 12

MS 487.3 (M+H), 509.3 (M+Na).
Anal Calcd for C₂₅H₂₅F₃N₄O₃: C, 61.72; H, 5.18; N, 11.52. Found: C, 61.89; H, 5.43; N, 11.14.
¹H NMR (CDCl₃, 300 MHz) δ 12.11 (s, 1H), 11.84 (s(br), 1H), 7.87 (d, J=9.9 Hz, 1H), 7.16 (m, 4H), 6.82 (m, 3H), 6.39 (s, 1H), 5.99 (s(br), 1H), 5.15 (s, 1H), 4.74 (m, 1H), 2.31 (m, 2H), 2.09 (m, 2H), 1.71 (m, 4H), 1.43 (d, J=6.6 Hz, 3H).

Example 13

MS 503.1 (M+H), 525.1 (M+Na).
Anal Calcd for C$_{25}$H$_{25}$F$_2$ClN$_4$O$_3$·1¹/₁₀H$_2$O: C, 57.44; H, 5.24; N, 10.72. Found: C, 57.79; H, 5.04; N, 10.32.
$^1$H NMR (CDCl$_3$, 300 MHz) δ 12.12 (s, 1H), 11.88 (s(br), 1H), 7.90 (d, J=9.9 Hz, 1H), 6.82 (m, 1H), 6.40 (s, 1H), 6.07 (s(br), 1H), 5.17 (s, 1H), 4.74 (m, 1H), 2.33 (m, 2H), 2.08 (m, 2H), 1.68 (m, 4H), 1.44 (d, J=6.6 Hz, 3H).

Example 14

$^1$H NMR (CDCl$_3$, 300 MHz) δ 11.71 (s, 1H), 7.79 (d, J=9.3 Hz, 1H), 7.21 (m, 5H), 7.06 (d, J=6.6 Hz, 2H), 6.77 (m, 1H), 6.43 (s, 1H), 5.11 (s, 1H), 4.71 (m, 1H), 1.58 (d, J=6.6 Hz, 3H), 1.39 (d, J=6.6 Hz, 3H).

Example 15

MS 483.3 (M+H), 505.3 (M+Na), 521.3 (M+K).
Anal Calcd for C$_{26}$H$_{28}$F$_2$N$_4$O$_3$·⁵/₄H$_2$O: C, 61.83; H, 6.09; N, 11.09. Found: C, 62.10; H, 5.97; N, 10.76.
$^1$H-NMR (CDCl$_3$, 300 MHz) δ 12.06 (s, 1H), 11.75 (s(br), 1H), 7.83 (d, J=9.9 Hz, 1H), 7.24 (m, 5H), 7.20 (d, J=6.6 Hz, 2H), 6.79 (m, 1H), 6.44 (s, 1H), 5.84 (s(br), 1H), 5.11 (s, 1H), 4.76 (m, 1H), 2.17 (m, 4H), 1.51 (m, 9H).

Example 16

MS 486.5 (M+H), 508.5 (M+Na).
Anal Calcd for C$_{25}$H$_{25}$F$_3$N$_4$O$_3$: C, 61.72; H, 5.18; N, 11.52. Found: C, 61.45; H, 5.26; N, 11.41.
$^1$H NMR (CDCl$_3$, 300 MHz) δ 11.51 (s(br), 1H), 7.60 (m, 1H), 7.34 (m, 1H), 7.06 (m, 4H), 6.90 (m, 1H), 6.79 (m, 1H), 6.47 (s, 1H), 5.12 (s, 1H), 4.73 (m, 1H), 2.52 (m, 2H), 2.17 (m, 2H), 1.80 (m, 4H), 1.39 (d, J=6.6 Hz, 3H).

Example 17

MS 461.0 (M+H), 482.2 (M+Na).
Anal Calcd for C$_{23}$H$_{23}$F$_3$N$_4$O$_3$: C, 59.99; H, 5.03; N, 12.17. Found: C, 60.08; H, 5.11; N, 11.96.
$^1$H NMR (CD$_3$OD, 300 MHz) δ 7.31 (m, 2H), 7.15 (m, 3H), 7.03 (m, 1H), 6.89 (m, 1H), 6.38 (s(br), 1H), 5.12 (s, 1H), 4.57 (m, 1H), 1.76 (s, 6H), 1.44 (d, J=7.1 Hz, 3H).

Example 18

MS 471.4 (M+H), 493.2 (M+Na).
Anal Calcd for C$_{25}$H$_{28}$F$_2$N$_4$O$_3$: C, 63.82; H, 6.00; N, 11.91. Found: C, 63.45; H, 5.92; N, 11.76.
$^1$H NMR (CD$_3$OD, 300 MHz) δ 7.15 (d, J=6.6 Hz, 2H), 6.90 (m, 4H), 6.46 (s, 1H), 5.12 (s, 1H), 4.57 (m, 1H), 2.28 (s, 6H), 1.69 (s, 6H), 1.45 (d, J=7.1 Hz, 3H).

Example 19

MS 479.0 (M+H), 501.2 (M+Na).

Anal Calcd for $C_{23}H_{22}F_4N_4O_3 \cdot \frac{3}{2}H_2O$: C, 54.65; H, 4.99; N, 11.08. Found: C, 54.95; H, 5.00; N, 10.77.

$^1$H NMR (CD$_3$OD, 300 MHz) δ 7.33 (m, 1H), 7.14 (d, J=6.0 Hz, 2H), 6.92 (m, 3H), 6.39 (s, 1H), 5.12 (s, 1H), 4.56 (m, 1H), 1.75 (s, 6H), 1.44 (d, J=7.1 Hz, 3H).

Example 20

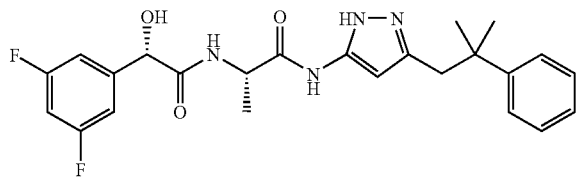

MS 457.2 (M+H), 478.8 (M+Na).

Anal Calcd for $C_{24}H_{26}F_2N_4O_3 \cdot \frac{1}{2}H_2O$: C, 61.93; H, 5.85; N, 12.04. Found: C, 61.75; H, 5.84; N, 11.88.

$^1$H NMR (CDCl$_3$, 300 MHz) δ 11.87 (s, 1H), 7.81 (d, J=9.9 Hz, 1H), 7.18 (m, 3H), 7.08 (m, 3H), 6.83 (m, 1H), 6.11 (s, 1H), 5.07 (s, 1H), 4.53 (m, 1H), 2.81 (d, J=5.3 Hz, 1H), 2.67 (m, 1H), 1.38 (d, J=6.6 Hz, 3H), 1.27 (m, 6H).

Example 21

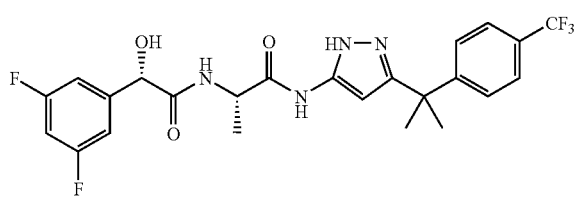

MS 511.0 (M+H), 533.2 (M+Na).

Anal. Calcd for $C_{24}H_{23}F_5N_4O_3$: C, 56.47; H, 4.54; N, 10.98. Found: C, 56.14; H, 4.72; N, 10.79.

$^1$H NMR (CDCl$_3$, 300 MHz) δ 12.18 (s, 1H), 7.97 (d, J=9.9 Hz, 1H), 7.47 (d, J=8.2 Hz, 2H), 7.31 (d, J=8.2 Hz, 2H), 7.03 (d, J=6.5 Hz, 2H), 6.76 (m, 1H), 6.41 (s, 1H), 5.10 (s, 1H), 4.76 (m, 1H), 1.67 (d, J=3.9 Hz, 6H), 1.45 (d, J=6.6 Hz, 3H).

Example 22

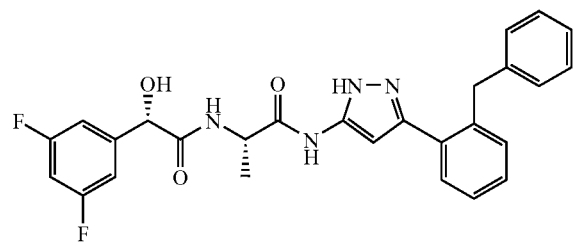

MS 491.4 (M+H), 513.4 (M+Na), 529.4 (M+K).

Anal Calcd for $C_{27}H_{24}F_5N_4O_3$: C, 66.11; H, 4.93; N, 11.42. Found: C, 65.97; H, 4.91; N, 11.18.

$^1$H NMR (CDCl$_3$, 300 MHz) δ 11.89 (s(br), 1H), 7.88 (d, J=9.3 Hz, 1H), 7.44 (m, 1H), 7.28 (m, 2H), 7.10 (m, 6H), 6.96 (d, J=7.1 Hz, 2H), 6.64 (m, 2H), 5.09 (s, 1H), 4.82 (m, 1H), 4.07 (m, 2H) 1.48 (d, J=6.6 Hz, 3H).

Example 23

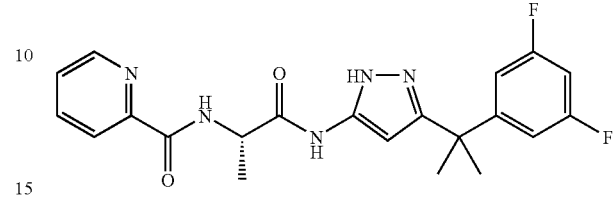

MS 414.0 (M+H), 436.0 (M+Na)

$^1$H NMR (CDCl$_3$, 300 MHz) δ 12.08 (s, 1H), 8.74 (d, J=9.9 Hz, 1H), 8.53 (d, J=4.4 Hz, 1H), 7.91 (d, J=8.2 Hz, 1H), 7.80 (m, 1H), 7.42 (m, 1H), 6.86 (d, J=7.1 Hz, 2H), 6.73 (s, 1H), 6.60 (m, 1H), 5.10 (m, 1H). 1.81 (s, 3H), 1.76 (s, 3H), 1.56 (d, J=6.6 Hz, 3H).

Example 24

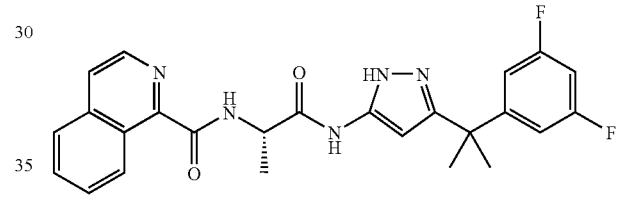

MS 464.0 (M+H), 486.2 (M+Na).

Anal Calcd for $C_{25}H_{23}F_2N_5O_2 \cdot \frac{3}{4}H_2O$: C, 62.94; H, 5.18; N, 14.68. Found: C, 63.09; H, 5.05; N, 14.77.

$^1$H NMR (CDCl$_3$, 300 MHz) δ 12.16 (s, 1H), 9.32 (d, J=8.8 Hz, 1H), 9.01 (d, J=9.9 Hz, 1H), 8.48 (d, J=5.5 Hz, 1H), 7.83 (m, 2H), 7.70 (t, J=7.7 Hz, 1H), 7.54 (t, J=8.2 Hz, 1H), 6.86 (d, J=6.0 Hz, 2H), 6.76 (s, 1H), 6.59 (m, 1H), 5.16 (m, 1H), 1.80 (s, 3H), 1.78 (s, 3H), 1.62 (d, J=6.6 Hz, 3H).

Example 25

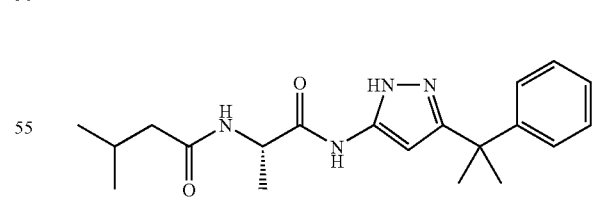

MS 357.2 (M+H).

Anal Calcd for $C_{20}H_{28}N_4O_2$: C, 67.39; H, 7.92; N, 15.72. Found: C, 67.05; H, 7.65; N, 15.72.

$^1$H NMR (CDCl$_3$, 300 MHz) δ 11.95 (s, 1H), 11.87 (s(br), 1H), 7.23 (m, 5H), 6.87 (d, J=9.3 Hz, 1H), 6.63 (s, 1H), 4.94 (m, 1H), 1.99 (m, 3H), 1.76 (s, 3H), 1.74 (s, 3H), 1.41 (d, J=6.6 Hz, 3H), 0.86 (d, J=6.0 Hz, 3H), 0.80 (d, J=5.5 Hz, 3H).

Example 26

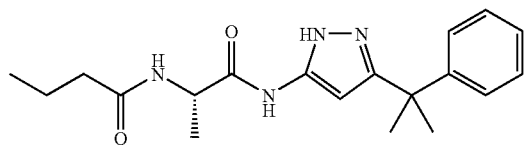

MS 343.1 (M+H).
¹H NMR (CDCl₃, 300 MHz) δ 11.86 (s, 1H), 7.23 (m, 5H), 6.60 (m, 2H), 6.63 (s, 1H), 4.93 (m, 1H), 2.19 (m, 2H), 1.75 (s, 3H), 1.74 (s, 3H), 1.50 (m, 2H), 1.40 (d, J=6.6 Hz, 3H), 0.84 (t, J=7.7 Hz, 3H).

Example 27

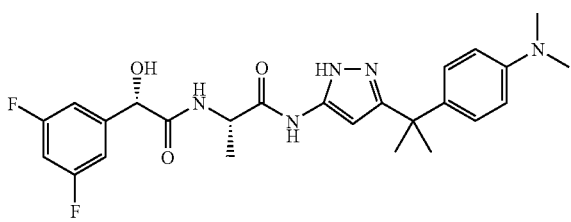

MS 486.1 (M+H).
¹H NMR (CDCl₃, 300 MHz) δ 11.91 (s, 1H), 7.86 (d, J=8.8 Hz, 1H), 7.07 (m, 4H), 6.74 (m, 1H), 6.61 (d, J=8.8 Hz, 2H), 6.49 (s, 1H), 5.06 (s, 1H), 4.75 (m, 1H), 2.83 (s, 6H), 1.63 (s, 6H), 1.40 (d, J=6.6 Hz, 3H).

Example 28

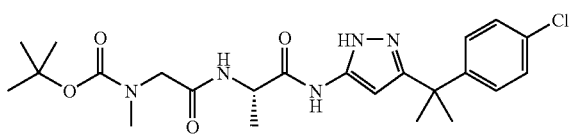

MS 478.1 (M+H).
¹H NMR (CDCl₃, 300 MHz) δ 7.22 (m, 4H), 6.57 (s, 1H), 4.86 (m, 1H), 3.78 (s(br), 2H), 2.88 (s, 3H), 1.72 (s, 3H), 1.71 (s, 3H), 1.40 (m, 12H).

Example 29

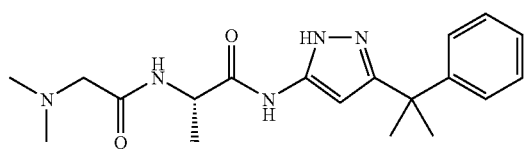

MS 358.1 (M+H).
¹H NMR (CDCl₃, 300 MHz) δ 11.82 (s, 1H), 7.89 (d, J=9.9 Hz, 1H), 7.22 (m, 5H), 6.65 (s, 1H), 4.89 (m, 1H), 2.84 (s, 2H), 2.23 (s, 6H), 1.75 (s, 3H), 1.74 (s, 3H), 1.39 (d, J=7.1 Hz, 3H).

Example 30

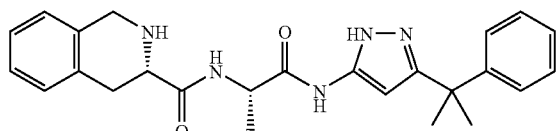

MS 432.1 (M+H).
¹H NMR (CD₃OD, 300 MHz) δ 7.31 (m, 9H), 6.50 (s(br), 1H), 4.68 (m, 1H), 4.19 (m, 2H), 3.81 (m, 1H), 3.12 (m, 2H), 1.85 (s, 6H), 1.62 (s, 3H).

Example 31

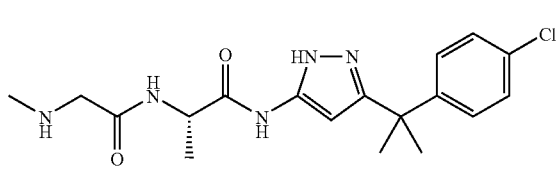

MS 378.1 (M+H).
¹H NMR (CD₃OD, 300 MHz) δ 7.38 (m, 4H), 6.46 (s, 1H), 4.69 (m, 1H), 3.65 (s, 2H), 2.64 (s, 3H), 1.80 (s, 6H), 1.57 (d, J=7.1 Hz, 3H).

Example 32

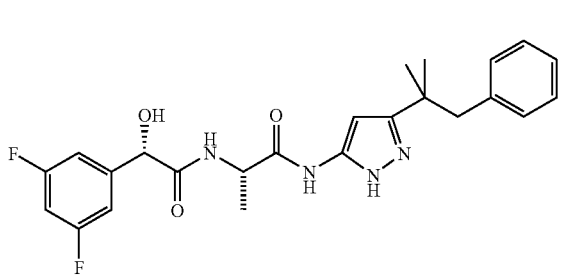

2-[2-(3,5-Difluoro-phenyl)-2-hydroxy-acetylamino]-N-[5-(1,1-dimethyl-2-phenyl-ethyl)-2H-pyrazol-3-yl]-propionamide MS 447 (M+H), 470 (M+Na)

MS 447 (M+H), 470 (M+Na)
¹H NMR (CDCl₃, 300 MHz) δ 7.13 (m, 5H), 6.88 (m, 3H), 6.28 (s, 1H), 5.096 (s, 1H), 4.55 (m, J=6.9, 1H), 2.87 (s, 2H), 1.41 (d, j=6.9 Hz, 3H), 1.283 (s, 6H)

Example 33

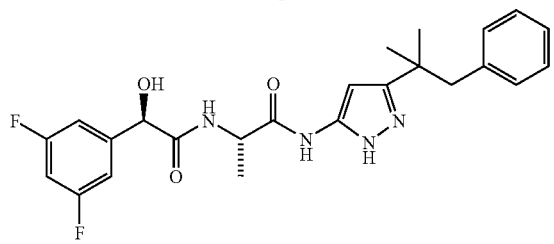

2-[2-(3,5-Difluoro-phenyl)-2-hydroxy-acetylamino]-N-[5-(1,1-dimethyl-2-phenyl-ethyl)-2H-pyrazol-3-yl]-propionamide MS 447 (M+H), 470 (M+Na)

Example 34

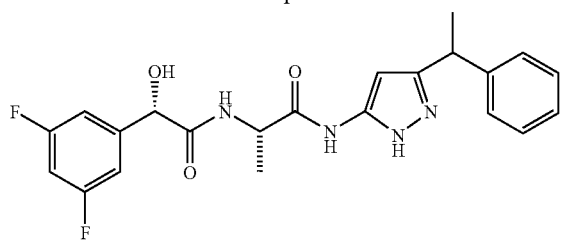

2-[2-(3,5-Difluoro-phenyl)-2-hydroxy-acetylamino]-N-[5-(1-phenyl-ethyl)-2H-pyrazol-3-yl]-propionamide MS 429 (M+H), 452 (M+Na)

Example 35

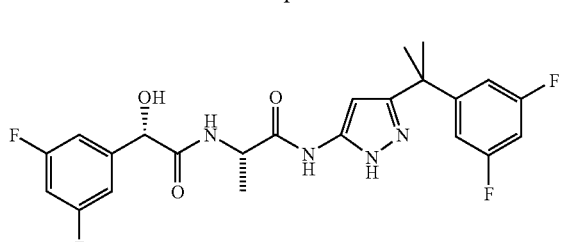

2-[2-(3,5-Difluoro-phenyl)-2-hydroxy-acetylamino]-N{-5-[1-(3,5-difluoro-phenyl)-1-methyl-ethyl]-2H-pyrazol-3-yl}-propionamide MS 479 (M+H)
$^1$H NMR (MeOH, 300 MHz) δ 7.11 (m, 2H), 6.81 (m, 3H), 6.43 (s, 1H), 5.09 (s, 1H), 4.54 (m, J=7.2, 1H), 1.67 (s, 6H), 1.41 (d, j=7.2 Hz, 3H)

Example 36

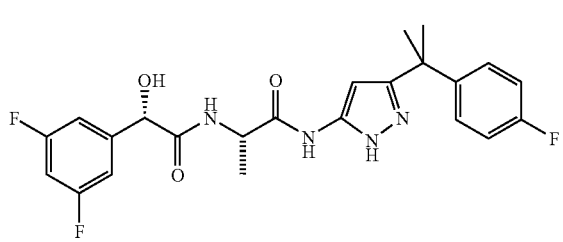

2-[2-(3,5-Difluoro-phenyl)-2-hydroxy-acetylamino]-N-{5-[1-(4-fluoro-phenyl)-1-methyl-ethyl]-2H-pyrazol-3-yl}-propionamide MS 461 (M+H)
$^1$H NMR (MeOH, 300 MHz) δ 7.27 (m, 2.3), 7.12 (m, 2H), 7.00 (m, 2H), 6.85 (m, 1H), 6.40 (s, 1H), 5.09 (s, 1H), 4.53 (m, 1H), 1.68 (s, 6H), 1.42 (d, J=6.9 Hz, 3H)

Example 37

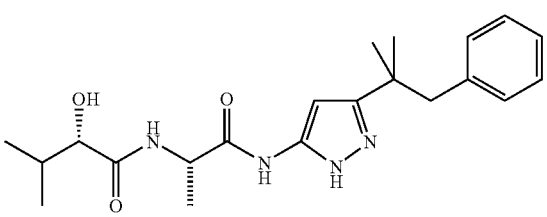

N-{1-[5-(1,1-Dimethyl-2-phenyl-ethyl)-2H-pyrazol-3-ylcarbamoyl]-ethyl}-2-hydroxy-3-methyl-butyramide MS 387 (M+H)
$^1$H NMR (DMSO, 300 MHz) δ 7.13 (m, 3H), 6.87 (m, 2H), 6.29 (s, 1H), 4.63 (m, 1H), 3.90 (d, J=3.6 Hz, 1H), 2.87 (s, 2H), 2.11 (m, 1H), 1.98 (d, J=3.9 Hz, 1H), 1.42 (d, J=6.9 Hz, 3H), 1.28 (s, 6H), 1.01 (d, J=6.9 Hz, 3H), 0.86 (d, J=6.6 Hz, 3H)

Example 38

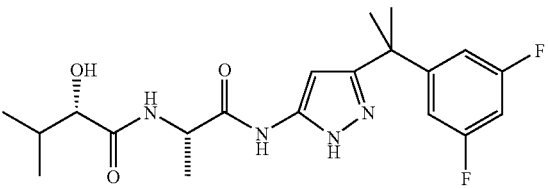

N-(1-{5-[1-(3,5-Difluoro-phenyl)-1-methyl-ethyl]-2H-pyrazol-3-ylcarbamoyl}-ethyl)-2-hydroxy-3-methyl-butyramide MS 409 (M+H)
$^1$H NMR (DMSO, 300 MHz) δ 6.84 (m, 3H), 6.44 (s, 1H), 4.62 (m, 1H), 3.90 (d, J=1.5, 1H), 2.1 (m, 1H), 1.67 (s, 6H), 1.43 (d, J=6.9 Hz, 3H), 1.00 (d, J=6.9 Hz, 3H), 0.85 (d, J=6.6 Hz, 3H)

Example 39

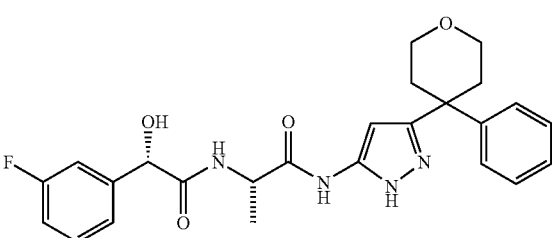

2-[2-(3,5-Difluoro-phenyl)-2-hydroxy-acetylamino]-N-[5-(4-phenyl-tetrahydro-pyran-4-yl)-2H-pyrazol-3-yl]-propionamide MS 485 (M+H), 506.8 (M+Na)
$^1$H NMR (MeOH, 300 MHz) δ 7.25 (m, 4H), 7.09 (m, 3H), 6.85 (m, 1H), 6.44 (s, 1H), 5.06 (s, 1H), 4.51 (m, 1H), 3.78 (m, 2H), 3.60 (m, 2H), 2.27 (m, 4H), 1.36 (d, J=6.9 Hz, 3H)

Example 40

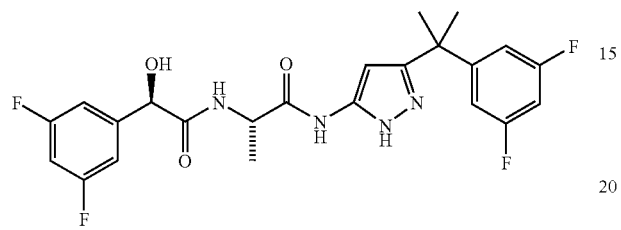

2-[2-(3,5-Difluoro-phenyl)-2-hydroxy-acetylamino]-N-{5-[1-(3,5-difluoro-phenyl)-1-methyl-ethyl]-2H-pyrazol-3-yl}-propionamide

MS 479 (M+H)

Example 41

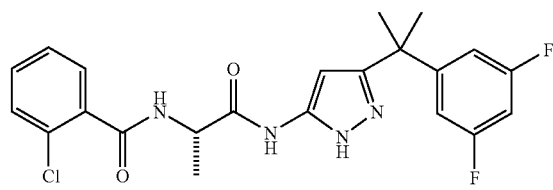

2-Chloro-N-(1-{5-[1-(3,5-difluoro-phenyl)-1-methyl-ethyl]-2H-pyrazol-3-ylcarbamoyl}-ethyl)-benzamide MS 446.8 (M+H), 468.8 (M+Na), 485 (M+K)
Anal Calcd for $C_{22}H_{21}ClF_2N_4O_2$: C, 59.13; H, 4.74; N, 12.54. Found: C, 58.88; H, 4.94; N, 12.19.
$^1$H NMR (MeOH, 300 MHz) δ 7.50 (m, 1H), 7.33 (m, 3H), 6.71 (m, 2H), 6.58 (m, 1H), 4.77 (m, 1H), 1.62 (s, 6H), 1.47 (d, J=9 Hz, 3H)

Example 42

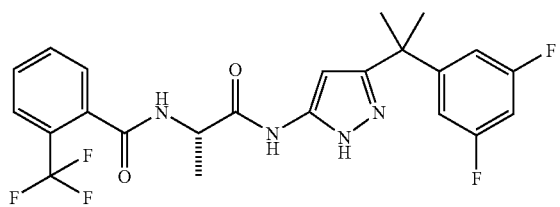

N-(1-{5-[1-(3,5-Difluoro-phenyl)-1-methyl-ethyl]-2H-pyrazol-3-ylcarbamoyl}-ethyl)-2-trifluorom-ethyl-benzamide MS 481 (M+H), 503 (M+Na), 518 (M+K)
Anal Calcd for $C_{23}H_{21}F_5N_4O_2$: C, 57.50; H, 4.41; N, 11.66. Found: C, 57.20; H, 4.57; N, 11.23.
$^1$H NMR (MeOH, 300 MHz) δ 7.66 (m, 4H), 6.79 (m, 3H), 6.51 (m, 1H), 4.67 (m, 1H), 1.66 (s, 6H), 1.46 (d, J=8.7 Hz, 3H)

Example 43

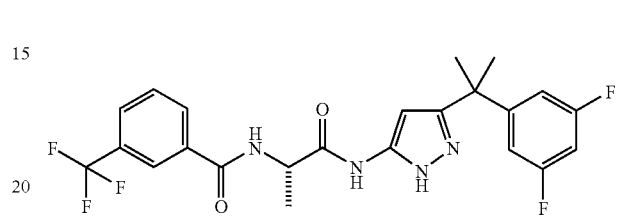

N-(1-{5-[1-(3,5-Difluoro-phenyl)-1-methyl-ethyl]-2H-pyrazol-3-ylcarbamoyl}-ethyl)-3-trifluorom-ethyl-benzamide MS 481 (M+H), 503 (M+Na), 518.8 (M+K)
Anal Calcd for $C_{23}H_{21}F_5N_4O_2$: C, 57.50; H, 4.41; N, 11.66. Found: C, 57.13; H, 4.46; N, 11.41.
$^1$H NMR (MeOH, 300 MHz) δ 8.19 (s, 1H), 8.10 (d, J=7.8 Hz, 1H), 7.80 (d, J=7.8 Hz, 1H) 7.61 (t, J=7.8 Hz, 1H), 6.752 (m, 3H), 6.43 (s, 1H), 4.72 (m, 1H), 1.64 (s, 6H), 1.52 (d, J=7.2 Hz, 3H)

Example 44

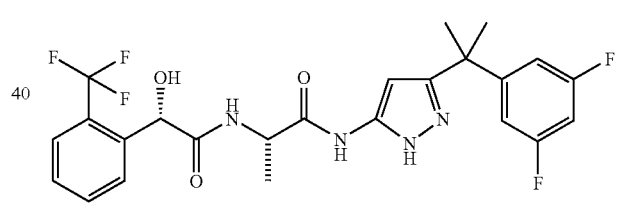

N-{5-[1-(3,5-Difluoro-phenyl)-1-methyl-ethyl]-2H-pyrazol-3-yl}-2-[2-hydroxy-2-(2-trifluoromethyl-phenyl)-acetylamino]-propionamide MS 511.2 (M+H), 533 (M+Na)
$^1$H NMR (MeOH, 300 MHz) δ 7.59 (m, 3H), 7.45 (m, 1H), 6.79 (m, 3H), 6.39 (m, 1H), 5.43 (m, 1H), 5.57 (m, 1H), 1.66 (s, 7H), 1.48 (d, J=6.9 Hz, 3H)

Example 45

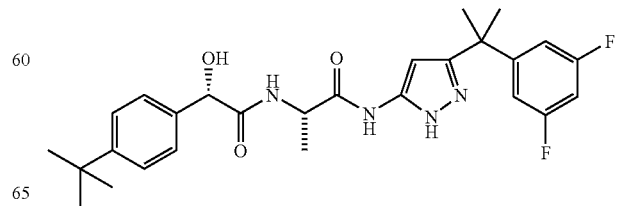

2-[2-(4-tert-Butyl-phenyl)-2-hydroxy-acetylamino]-
N-{5-[1-(3,5-difluoro-phenyl)-1-methyl-ethyl]-2H-
pyrazol-3-yl}-propionamide MS 499.2 (M+H), 521 (M+Na)
$^1$H NMR (MeOH, 300 MHz) δ 7.36 (s, 4H), 6.82 (m, 3H), 6.41 (s, 1H), 5.01 (s, 1H), 4.53 (m, 1H), 1.66 (s, 6H), 1.41 (d, J=6.9 Hz, 3H), 1.28 (s, 9H)

Example 46

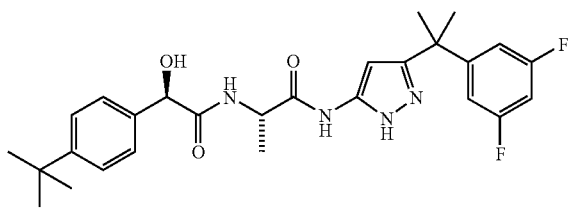

2-[2-(4-tert-Butyl-phenyl)-2-hydroxy-acetylamino]-
N-{5-[1-(3,5-difluoro-phenyl)-1-methyl-ethyl]-2H-
pyrazol-3-yl}-propionamide MS 499.2 M+H), 521 (M+Na)
$^1$H NMR (MeOH, 300 MHz) δ 7.35 (s, 4H), 6.79 (m, 3H), 6.38 (s, 1H), 5.01 (s, 1H), 5.46 (m, 1H), 1.65 (s, 6H), 1.43 (d, J=6.9 Hz, 3H), 1.26 (s, 9H).

Example 47

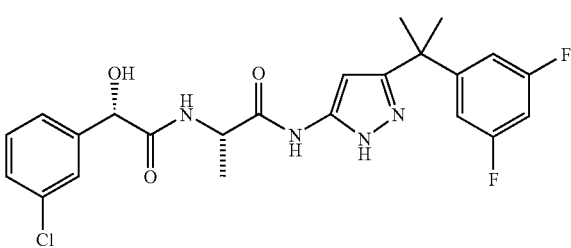

2-[2-(3-Chloro-phenyl)-2-hydroxy-acetylamino]-N-
{5-[1-(3,5-difluoro-phenyl)-1-methyl-ethyl]-2H-
pyrazol-3-yl}-propionamide MS 477.2 (M+H), 499.0 (M+Na), 514.8 (M+K)
Anal Calcd for $C_{23}H_{23}ClF_2N_4O_3$: C, 57.92; H, 4.86; N, 11.75. Found: C, 57.75; H, 5.27; N, 11.23.
$^1$H NMR (MeOH, 300 MHz) δ 7.47 (s, 1H), 7.37 (m, 1H), 7.27 (m, 2H), 6.78 (m, 3H), 6.42 (s, 1H), 5.04 (s, 1H), 4.51 (m, 1H), 1.65 (s, 6H), 1.40 (d, J=7.2 Hz, 3H)

Example 48

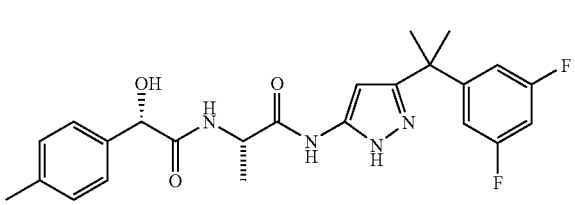

N-{5-[1-(3,5-Difluoro-phenyl)-1-methyl-ethyl]-2H-
pyrazol-3-yl}-2-(2-hydroxy-2-p-tolyl-acetylamino)-
propionamide MS 457.2 (M+H), 479 (M+Na)
$^1$H NMR (MeOH, 300 MHz) δ 7.30 (d, J=8.1 Hz, 2H), 7.13 (d, J=7.8 Hz, 2H), 6.79 (m, 3H), 6.43 (s, 1H), 4.99 (s, 1H), 4.53 (m, 1H), 2.28 (s, 3H), 1.654 (s, 6H), 1.40 (d, J=6.9 Hz, 3H)

Example 49

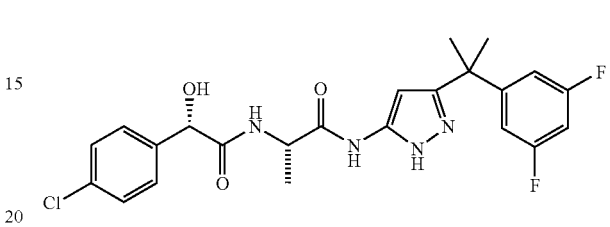

2-[2-(4-Chloro-phenyl)-2-hydroxy-acetylamino]-N-
{5-[1-(3,5-difluoro-phenyl)-1-methyl-ethyl]-2H-
pyrazol-3-yl}-propionamide MS 477.0 (M+H), 498.8 (M+Na), 514.8 (M+K)
Anal Calcd for $C_{23}H_{23}ClF_2N_4O_3$: C, 57.92; H, 4.86; N, 11.75. Found: C, 57.70; H, 4.92; N, 11.43.
$^1$H NMR (MeOH, 300 MHz) δ 7.43 (d, J=8.4 Hz, 2H), 7.30 (d, J=10.8 Hz, 2H), 6.78 (m, 3H), 6.40 (s, 1H), 5.04 (s, 1H), 4.52 (m, 1H), 1.647 (s, 6H), 1.39 (d, J=7.2 Hz, 3H)

Example 50

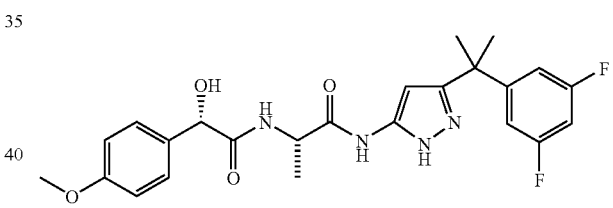

N-{5-[1-(3,5-Difluoro-phenyl)-1-methyl-ethyl]-2H-
pyrazol-3-yl}-2-[2-hydroxy-2-(4-methoxy-phenyl)-
acetylamino]-propionamide MS 473 (M+H), 495 (M+Na)
Anal Calcd for $C_{24}H_{26}F_2N_4O_4$: C, 61.01; H, 5.55; N, 11.86. Found: C, 61.63; H, 5.25; N, 11.11.
$^1$H NMR (MeOH, 300 MHz) δ 7.32 (m, 2H), 6.83 (m, 5H), 6.45 (s, 1H), 4.98 (s, 1H), 4.51 (m, 1H), 3.75 (s, 3H), 1.66 (s, 6H), 1.41 (d, J=6.9 Hz, 3H)

Example 51

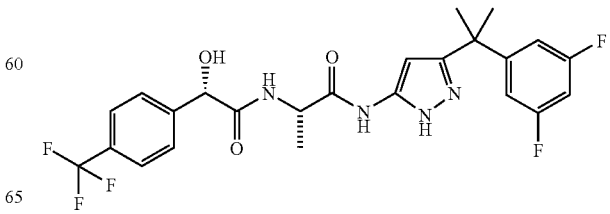

33

N-{5-[1-(3,5-Difluoro-phenyl)-1-methyl-ethyl]-2H-pyrazol-3-yl}-2-[2-hydroxy-2-(4-trifluoromethyl-phenyl)-acetylamino]-propionamide MS 511 (M+H), 532.8 (M+Na)

Anal Calcd for $C_{24}H_{23}F_5N_4O_3$: C, 56.47; H, 4.54; N, 10.98. Found: C, 56.12; H, 4.68; N, 10.53.

$^1$H NMR (MeOH, 300 MHz) δ 7.64 (m, 4H), 6.78 (m, 3H), 6.48 (s, 1H), 5.14 (s, 1H), 4.52 (m, 1H), 1.65 (s, 6H), 1.39 (d, J=6.9 Hz, 3H)

Example 52

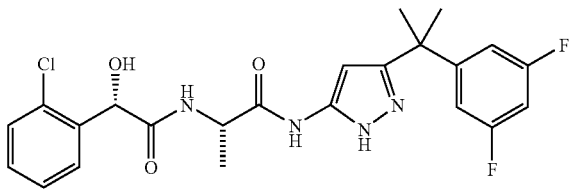

2-[2-(2-Chloro-phenyl)-2-hydroxy-acetylamino]-N-{5-[1-(3,5-difluoro-phenyl)-1-methyl-ethyl]-2H-pyrazol-3-yl}-propionamide

MS 477 (M+H)

$^1$H NMR (MeOH, 300 MHz) δ 7.36 (m, 2H), 7.27 (m, 2H), 6.79 (m, 3H), 6.51 (s, 1H), 5.51 (s, 1H), 4.57 (m, 1H), 1.66 (s, 6H), 1.46 (d, J=6.9 Hz, 3H)

Example 53

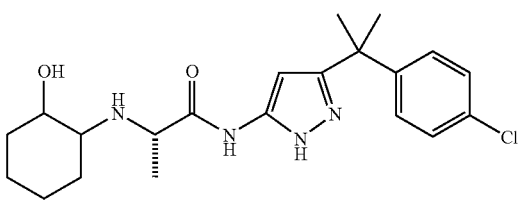

N-{5-[1-(4-Chloro-phenyl)-1-methyl-ethyl]-2H-pyrazol-3-yl}-2-(2-hydroxy-cyclohexylamino)-propionamide

MS 406 (M+H)

$^1$H NMR (CDCl$_3$, 300 MHz) δ 7.24 (m, 4H), 6.53 (s, 1H), 4.67 (m, 6H), 3.82 (m, 1H), 2.66 (m, 1H), 2.09 (m, 1H), 1.58 (m, 13H), 1.17 (m, 3H)

Example 54

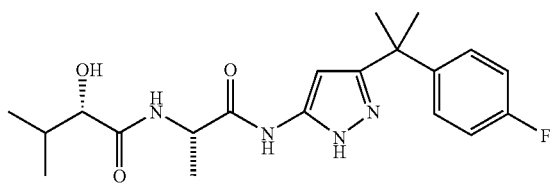

34

N-(1-{5-[1-(4-Fluoro-phenyl)-1-methyl-ethyl]-2H-pyrazol-3-ylcarbamoyl}-ethyl)-2-hydroxy-3-methyl-butyramide

MS 391 (M+H)

$^1$H NMR (MeOH, 300 MHz) δ 7.27 (m, 2H), 6.99 (m, 2H), 6.40 (s, 1H), 4.59 (m, 1H), 3.89 (d, J=3.6 Hz, 1H), 2.11 (m, 1H), 1.69 (s, 6H), 1.44 (d, J=7.2 Hz, 3H), 1.02 (d, J=6.9 Hz, 3H), 0.87 (d, J=6.9 Hz, 3H)

Example 55

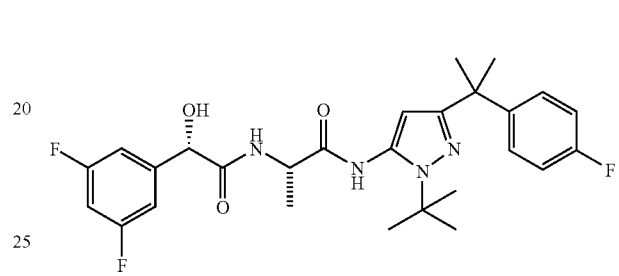

N-{2-tert-Butyl-5-[1-(4-fluoro-phenyl)-1-methyl-ethyl]-2H-pyrazol-3-yl}-2-[2-(3,5-difluoro-phenyl)-2-hydroxy-acetylamino]-propionamide

MS 517 (M+H)

$^1$H NMR (CDCl$_3$, 300 MHz) δ 8.18 (s, 1H), 7.24 (m, 4H), 6.96 (m, 2H), 6.91 (m, 2H), 6.77 (m, 1H), 5.97 (s, 1H), 5.01 (s, 1H), 4.49 (m, 1H), 1.61 (s, 6H), 1.56 (s, 9H), 1.38 (d, J=7.2 Hz, 3H)

Example 56

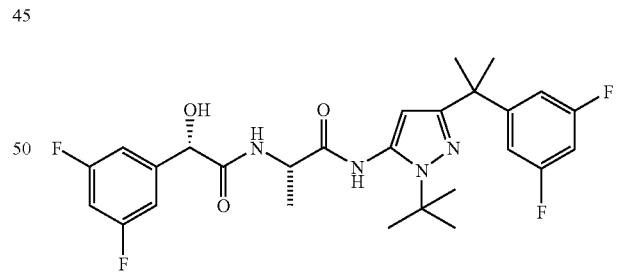

N-{2-tert-Butyl-5-[1-(3,5-difluoro-phenyl)-1-methyl-ethyl]-2H-pyrazol-3-yl}-2-[2-(3,5-difluoro-phenyl)-2-hydroxy-acetylamino]-propionamide

MS 535 (M+H)

$^1$H NMR (CDCl$_3$, 300 MHz) δ 8.44 (s, 1H), 7.38 (d, J=7.8 Hz, 1H), 6.93 (m, 2H), 6.75 (m, 3H), 6.54 (m, 1H), 5.96 (s,

1H), 4.97 (s, 1H), 4.64 (s, 1H), 4.52 (m, 1H), 1.58 (s, 6H), 1.51 (s, 9H), 1.23 (d, J=6.9 Hz, 3H)

Example 57

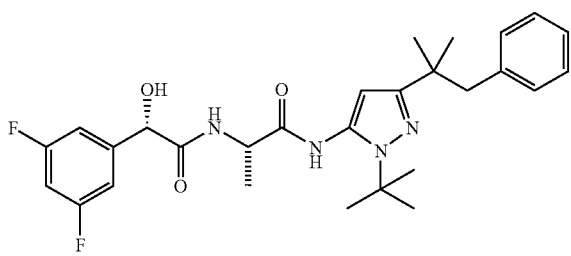

N-[2-tert-Butyl-5-(1,1-dimethyl-2-phenyl-ethyl)-2H-pyrazol-3-yl]-2-[2-(3,5-difluoro-phenyl)-2-hydroxy-acetylamino]-propionamide MS 513 (M+H)
$^1$H NMR (CDCl$_3$, 300 MHz) δ 8.30 (s, 1H), 7.41 (d, J=7.5 Hz, 1H), 7.14 (m, 3H), 6.97 (m, 4H), 6.72 (m, 1H), 6.01 (s, 1H), 5.00 (s, 1H), 4.52 (m, 1H), 2.85 (s, 2H), 1.52 (s, 9H), 1.38 (d, J=6.9 Hz, 3H), 1.18 (s, 6H)

Example 58

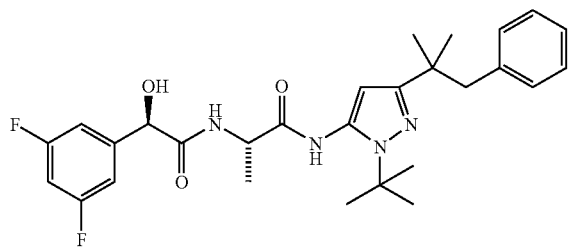

N-[2-tert-Butyl-5-(1,1-dimethyl-2-phenyl-ethyl)-2H-pyrazol-3-yl]-2-[2-(3,5-difluoro-phenyl)-2-hydroxy-acetylamino]-propionamide MS 513 (M+H)
$^1$H NMR (CDCl$_3$, 300 MHz) δ 8.15 (s, 1H), 7.43 (d, J=7.5 Hz, 1H), 7.13 (m, 3H), 6.96 (m, 4H), 6.70 (m, 1H), 5.96 (s, 1H), 5.04 (s, 1H), 4.61 (m, 1H), 4.32 (m, 1H), 2.81 (s, 2H), 1.44 (d, J=6.9 Hz, 3H), 1.17 (s, 6H)

Example 58a

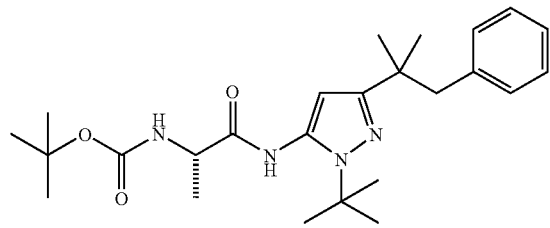

{1-[2-tert-Butyl-5-(1,1-dimethyl-2-phenyl-ethyl)-2H-pyrazol-3-ylcarbamoyl]-ethyl}-carbamic acid tert-butyl ester MS 443 (M+H)
$^1$H NMR (CDCl$_3$, 300 MHz) δ 7.18 (m, 3H), 6.97 (m, 2H), 6.17 (s, 1H), 4.32 (m, 1H), 2.88 (s, 2H), 1.58 (s, 9H), 1.46 (m, 12H), 1.22 (s, 6H)

Example 59

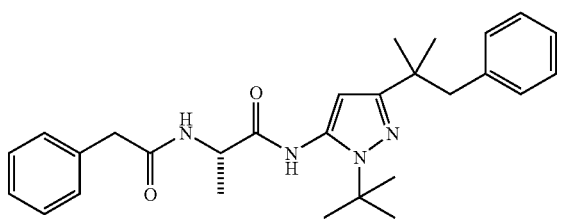

N-[2-tert-Butyl-5-(1,1-dimethyl-2-phenyl-ethyl)-2H-pyrazol-3-yl]-2-phenylacetylamino-propionamide MS 390 (M+H)
$^1$H NMR (CDCl$_3$, 300 MHz) δ 7.40 (m, 5H), 7.16 (m, 3H), 6.94 (m, 3H), 6.25 (s, 1H), 3.77 (s, 2H), 2.86 (s, 2H), 1.29 (s, 9H), 1.21 (s, 6H)

Example 60

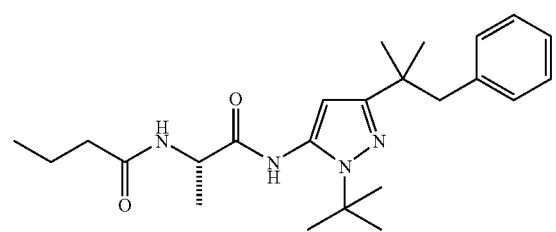

N-{1-[2-tert-Butyl-5-(1,1-dimethyl-2-phenyl-ethyl)-2H-pyrazol-3-ylcarbamoyl]-ethyl}-butyramide MS 342 (M+H)
$^1$H NMR (MeOH, 300 MHz) δ 7.11 (m, 3H), 6.92 (m, 2H), 5.82 (s, 1H), 2.86 (s, 2H), 2.34 (t, J=6.6 Hz, 2H), 1.71 (m, 2H), 1.57 (s, 9H), 1.22 (s, 6H) 1.02 (t, J=7.5 Hz, 3H)

Example 61

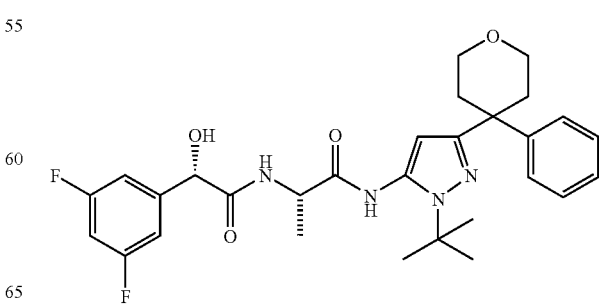

N-[2-tert-Butyl-5-(4-phenyl-tetrahydro-pyran-4-yl)-2H-pyrazol-3-yl]-2-[2-(3,5-difluoro-phenyl)-2-hydroxy-acetylamino]-propionamide MS 541.4 (M+H), 563.4 (M+Na)

Anal Calcd for $C_{29}H_{34}N_4F_2O_3$: C, 64.43; H, 6.34; N, 10.36. Found: C, 64.20; H, 6.22; N, 10.30.

$^1$H NMR (MeOH, 300 MHz) δ 8.43 (s, 1H), 7.24 (m, 5H), 7.09 (m, 1H), 6.91 (m, 2H), 6.70 (m, 1H), 5.91 (s, 1H), 4.90 (s, 1H), 4.78 (s, 1H), 4.42 (m, 1H), 3.73 (m, 4H), 2.38 (m, 2H), 2.12 (m, 3H), 1.51 (s, 9H), 1.20 (d, J=6 Hz, 3H)

Example 62

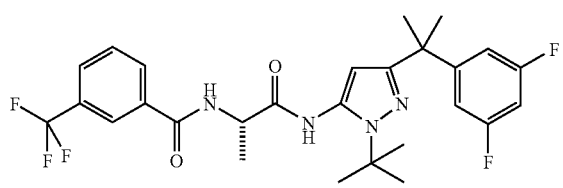

N-(1-{2-tert-Butyl-5-[1-(3,5-difluoro-phenyl)-1-methyl-ethyl]-2H-pyrazol-3-ylcarbamoyl}-ethyl)-3-trifluoromethyl-benzamide MS 537.2 (M+H), 559.2 (M+Na)

Anal Calcd for $C_{27}H_{29}F_5N_4O_2$: C, 60.44; H, 5.45; N, 10.44. Found: C, 60.27; H, 5.26; N, 10.17.

$^1$H NMR (CDCl$_3$, 300 MHz) δ 8.92 (s, 1H), 8.01 (s, 1H), 7.88 (d, J=7.8 Hz, 1H), 7.89 (d, J=7.5 Hz, 1H), 7.68 (d, J=7.8 Hz, 1H), 7.39 (t, J=7.8 Hz, 1H), 6.77 (m, 2H), 6.50 (m, 1H), 5.94 (s, 1H), 5.04 (m, 1H), 1.55 (s, 6H), 1.52 (m, 12H)

Example 63

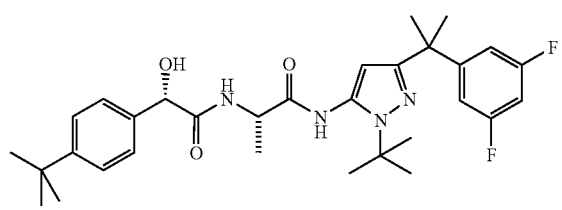

N-{2-tert-Butyl-5-[1-(3,5-difluoro-phenyl)-1-methyl-ethyl]-2H-pyrazol-3-yl}-2-[2-(4-tert-butyl-phenyl)-2-hydroxy-acetylamino]-propionamide MS 555 (M+H), 577.2 (M+Na)

Anal Calcd for $C_{31}H_{40}F_2N_4O_3$: C, 67.13; H, 7.27; N, 10.10. Found: C, 67.07; H, 7.28; N, 9.90.

$^1$H NMR (CDCl$_3$, 300 MHz) δ 8.61 (s, 1H), 7.32 (m, 3H), 7.22 (m, 2H), 6.82 (m, 2H), 6.54 (m, 1H), 5.98 (s, 1H), 4.95 (d, J=3 Hz, 1H), 4.56 (m, 1H), 3.98 (d, J=6 Hz, 1H), 1.58 (s, 6H), 1.48 (s, 9H), 1.28 (m, 12H)

Example 64

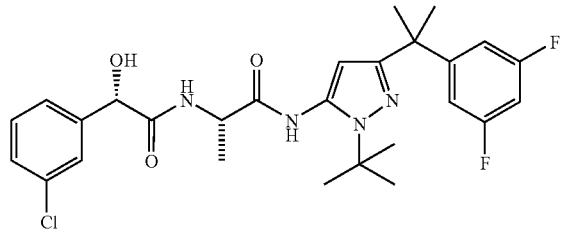

N-{2-tert-Butyl-5-[1-(3,5-difluoro-phenyl)-1-methyl-ethyl]-2H-pyrazol-3-yl}-2-[2-(3-chloro-phenyl)-2-hydroxy-acetylamino]-propionamide MS 533.01 (M+H), 555 (M+Na)

Anal Calcd for $C_{27}H_{31}ClF_2N_4O_3$: C, 60.84; H, 5.86; N, 10.51. Found: C, 60.62; H, 6.03; N, 10.19.

$^1$H NMR (CDCl$_3$, 300 MHz) 8.46 (s, 1H), 7.35 (m, 2H), 7.20 (m, 3H), 6.80 (m, 2H), 6.53 (m, 1H), 5.95 (s, 1H), 4.95 (s, 1H), 4.52 (m, 1H), 1.56 (s, 6H), 1.48 (s, 9H), 1.29 (d, J=6 Hz, 3H)

Example 65

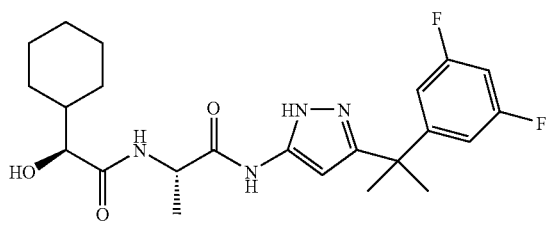

2-(2-Cyclohexyl-2-hydroxy-acetylamino)-N-{5-[1-(3,5-difluoro-phenyl)-1-methyl-ethyl]-2H-pyrazol-3-yl}-propionamide MS 449 (M+H), 471 (M+Na)

Anal. Calcd for $C_{23}H_{30}F_2N_4O_3$: C, 61.59; H, 6.74; N, 12.49. Found: C, 61.66; H, 6.80; N, 12.28.

Example 66

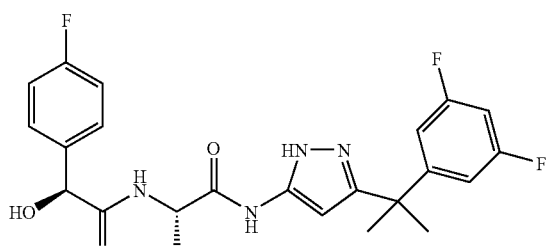

N-{5-[1-(3,5-Difluoro-phenyl)-1-methyl-ethyl]-2H-pyrazol-3-yl}-2-[2-(4-fluoro-phenyl)-2-hydroxy-acetylamino]-propionamide MS 461 (M+H), 483 (M+Na)
Anal. Calcd for $C_{23}H_{23}F_3N_4O_3$: C, 60.00; H, 5.03; N, 12.17. Found: C, 60.20; H, 5.38; N, 11.96.

Example 67

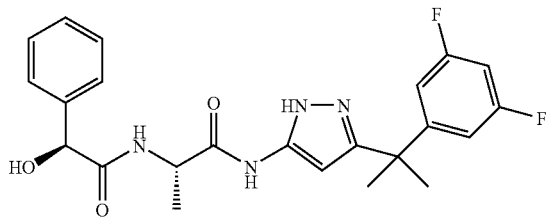

N-{5-[1-(3,5-Difluoro-phenyl)-1-methyl-ethyl]-2H-pyrazol-3-yl}-2-(2-hydroxy-2-phenyl-acetylamino)-propionamide MS 443 (M+H), 465 (M+Na)
Anal. Calcd for $C_{23}H_{24}F_2N_4O_3$: C, 62.43; H, 5.47; N, 12.66. Found: C, 61.89; H, 5.67; N, 12.38.

Example 68

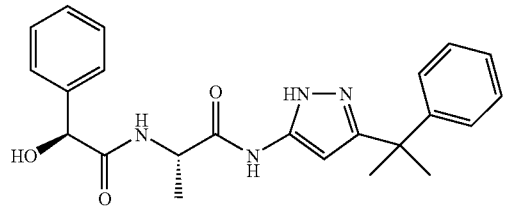

2-(2-Hydroxy-2-phenyl-acetylamino)-N-[5-(1-methyl-1-phenyl-ethyl)-2H-pyrazol-3-yl]-propionamide MS 407 (M+H), 429 (M+Na)
Anal. Calcd for $C_{23}H_{26}N_4O_3$: C, 67.96; H, 6.44; N, 13.78. Found: C, 66.58; H, 6.70; N, 13.66.

Example 69

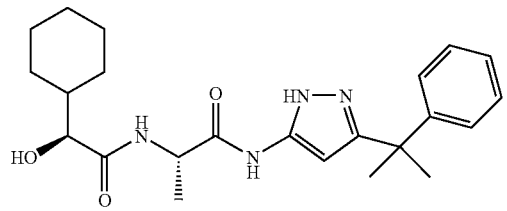

2-(2-Cyclohexyl-2-hydroxy-acetylamino)-N-[5-(1-methyl-1-phenyl-ethyl)-2H-pyrazol-3-yl]-propionamide MS 413 (M+H), 435 (M+Na)

Example 70

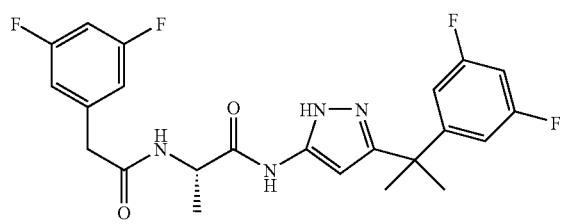

[2-(3,5-Difluoro-phenyl)-acetylamino]-N-{5-[1-(3,5-difluoro-phenyl)-1-methyl-ethyl]-2H-pyrazol-3-yl}-propionamide MS 463 (M+H), 485 (M+Na)
Anal. Calcd for $C_{23}H_{22}F_4N_4O_2$: C, 59.74; H, 4.80; N, 12.12. Found: C, 59.51; H, 4.88; N, 11.91.

Example 71

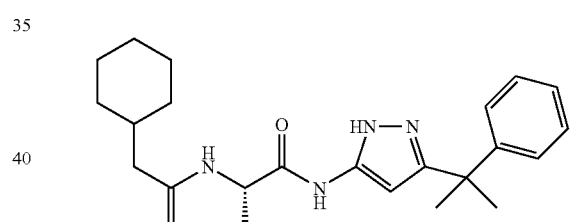

2-(2-Cyclohexyl-acetylamino)-N-[5-(1-methyl-1-phenyl-ethyl)-2H-pyrazol-3-yl]-propionamide MS 397 (M+H), 419 (M+Na)
Anal. Calcd for $C_{23}H_{33}N_4O_2$: C, 69.67; H, 8.13; N, 14.13. Found: C, 69.40; H, 8.20; N, 14.01.

Example 72

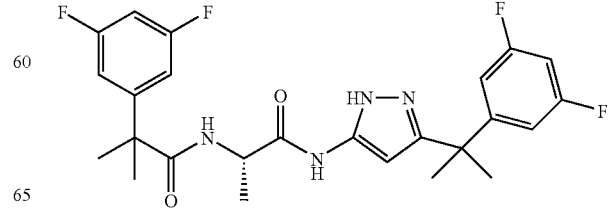

41

2-(3,5-Difluoro-phenyl)-N-(1-{5-[1-(3,5-difluoro-phenyl)-1-methyl-ethyl]-2H-pyrazol-3-ylcarbamoyl}-ethyl)-isobutyramide MS 491 (M+H), 513 (M+Na)
Anal. Calcd for $C_{25}H_{26}F_4N_4O_2$: C, 61.22; H, 5.34; N, 11.42. Found: C, 61.16; H, 5.60; N, 11.19.

Example 73

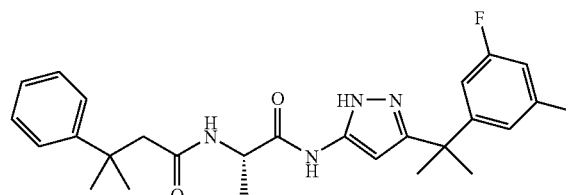

N-(1-{5-[1-(3,5-Difluoro-phenyl)-1-methyl-ethyl]-2H-pyrazol-3-ylcarbamoyl}-ethyl)-3-methyl-3-phenyl-butyramide MS 469 (M+H), 491 (M+Na)
Anal. Calcd for $C_{26}H_{30}F_2N_4O_2$: C, 66.65; H, 6.45; N, 11.96. Found: C, 66.31; H, 6.50; N, 11.89.

Example 74

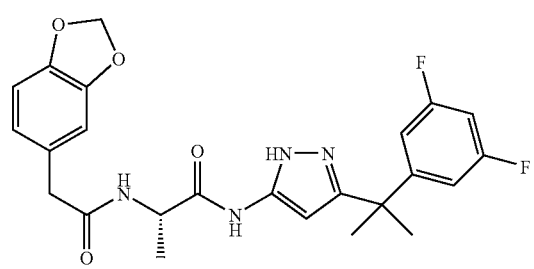

(2-Benzo[1,3]dioxol-5-yl-acetylamino)-N-{5-[1-(3,5-difluoro-phenyl)-1-methyl-ethyl]-2H-pyrazol-3-yl}-propionamide MS 471 (M+H), 493 (M+Na)
Anal. Calcd for $C_{24}H_{24}F_2N_4O_4$: C, 61.27; H, 5.14; N, 11.91. Found: C, 60.72; H, 5.48; N, 11.59.

Example 75

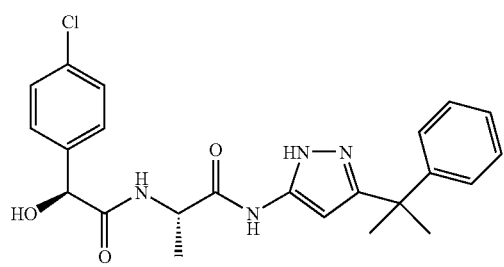

42

2-[2-(4-Chloro-phenyl)-2-hydroxy-acetylamino]-N-[5-(1-methyl-1-phenyl-ethyl)-2H-pyrazol-3-yl]-propionamide MS 463 (M+Na)
Anal. Calcd for $C_{23}H_{25}ClN_4O_3$: C, 62.65; H, 5.71; N, 12.71. Found: C, 62.38; H, 5.97; N, 12.38.

Example 76

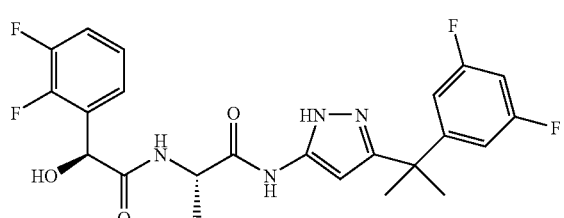

2-[2-(2,3-Difluoro-phenyl)-2-hydroxy-acetylamino]-N-{5-[1-(3,5-difluoro-phenyl)-1-methyl-ethyl]-2H-pyrazol-3-yl}-propionamide MS 479 (M+H)
Anal. Calcd for $C_{23}H_{22}F_4N_4O_3$: C, 57.74; H, 4.63; N, 11.71. Found: C, 57.41; H, 4.89; N, 11.31.

Example 77

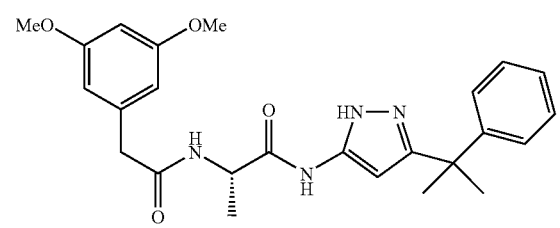

2-[2-(3,5-Dimethoxy-phenyl)-acetylamino]-N-[5-(1-methyl-1-phenyl-ethyl)-2H-pyrazol-3-yl]-propionamide MS 451 (M+H), 473 (M+Na)
Anal. Calcd for $C_{25}H_{30}N_4O_4$: C, 66.65; H, 6.71; N, 12.44. Found: C, 66.11; H, 6.62; N, 12.29.

Example 78

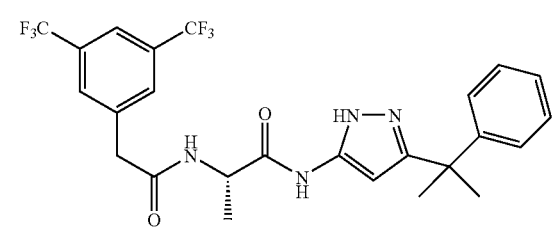

43

2-[2-(3,5-Bis-trifluoromethyl-phenyl)-acetylamino]-N-[5-(1-methyl-1-phenyl-ethyl)-2H-pyrazol-3-yl]-propionamide MS 527 (M+H)
Anal. Calcd for $C_{25}H_{24}F_6N_4O_2$: C, 57.03; H, 4.59; N, 10.64. Found: C, 56.82; H, 4.38; N, 10.54.

Example 79

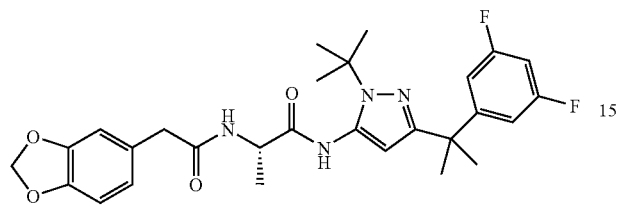

2-(2-Benzo[1,3]dioxol-5-yl-acetylamino)-N-{2-tert-butyl-5-[1-(3,5-difluoro-phenyl)-1-methyl-ethyl]-2H-pyrazol-3-yl}-propionamide MS 527 (M+H), 549 (M+Na)
Anal. Calcd for $C_{28}H_{32}F_2N_4O_4$: C, 63.87; H, 6.13; N, 10.64. Found: C, 63.77; H, 6.02; N, 10.53.

Example 80

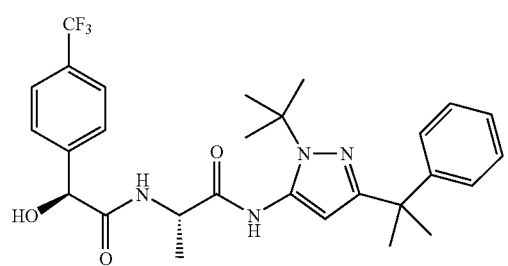

N-[2-tert-Butyl-5-(1-methyl-1-phenyl-ethyl)-2H-pyrazol-3-yl]-2-[2-hydroxy-2-(4-trifluoromethyl-phenyl)-acetyl amino]-propionamide MS 531 (N+H), 553 (M+Na)
Anal. Calcd for $C_{28}H_{33}F_3N_4O_3$: C, 63.38; H, 6.27; N, 10.56. Found: C, 62.99; H, 6.56; N, 10.23.

Example 81

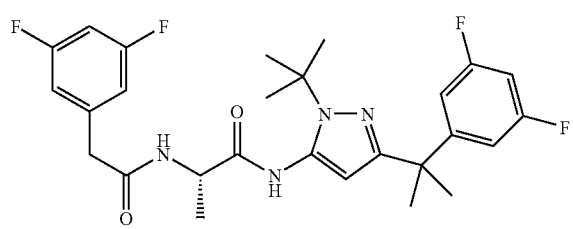

44

N-{2-tert-Butyl-5-[1-(3,5-difluoro-phenyl)-1-methyl-ethyl]-2H-pyrazol-3-yl}-2-[2-(3,5-difluoro-phenyl)-acetylamino]-propionamide MS 519 (M+H), 541 (M+Na)
Anal. Calcd for $C_{27}H_{30}F_4N_4O_2$: C, 62.54; H, 5.83; N, 10.80. Found: C, 62.26; H, 5.74; N, 10.44.

Example 82

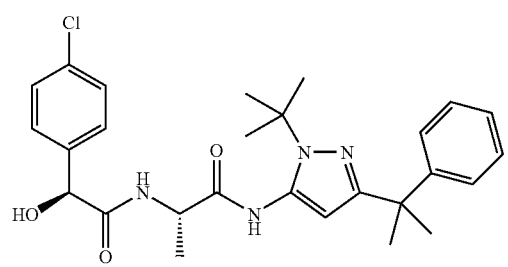

N-[2-tert-Butyl-5-(1-methyl-1-phenyl-ethyl)-2H-pyrazol-3-yl]-2-[2-(4-chloro-phenyl)-2-hydroxy-acetylamino]-propionamide MS 497 (M+H), 519 (M+Na)

Example 83

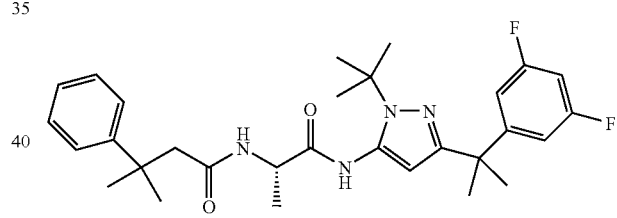

N-(1-{2-tert-Butyl-5-[1-(3,5-difluoro-phenyl)-1-methyl-ethyl]-2H-pyrazol-3-ylcarbamoyl}-ethyl)-3-methyl-3-phenyl-butyramide MS 525 (M+H), 547 (M+Na)
Anal. Calcd for $C_{30}H_{38}F_2N_4O_2$: C, 68.68; H, 7.30; N, 10.68. Found: C, 68.37; H, 7.54; N, 10.52.

Example 84

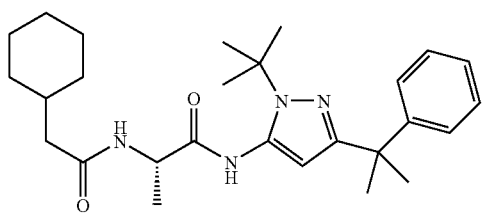

N-[2-tert-Butyl-5-(1-methyl-1-phenyl-ethyl)-2H-pyrazol-3-yl]-2-(2-cyclohexyl-acetylamino)-propionamide MS 453 (M+H), 475 (M+Na)
Anal. Calcd for $C_{27}H_{40}N_4O_2$: C, 71.65; H, 8.91; N, 12.38. Found: C, 71.35; H, 8.66; N, 11.81.

Example 85

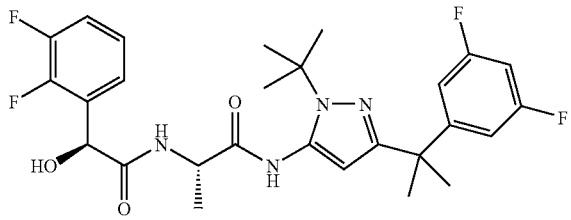

N-{2-tert-Butyl-5-[1-(3,5-difluoro-phenyl)-1-methyl-ethyl]-2H-pyrazol-3-yl}-2-[2-(2,3-difluoro-phenyl)-2-hydroxy-acetylamino]-propionamide MS 535 (M+H), 557 (M+Na)
Anal. Calcd for $C_{27}H_{30}F_4N_4O_3$: C, 60.67; H, 5.66; N, 10.48. Found: C, 60.27; H, 5.71; N, 10.26.

Example 86

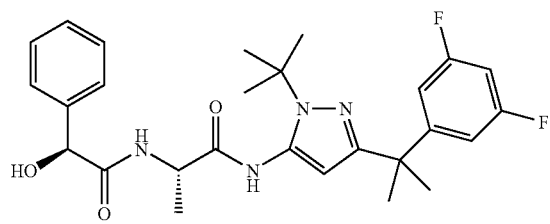

N-{2-tert-Butyl-5-[1-(3,5-difluoro-phenyl)-1-methyl-ethyl]-2H-pyrazol-3-yl}-2-(2-hydroxy-2-phenyl-acetylamino)-propionamide MS 547 (M+H), 569 (M+Na)
Anal. Calcd for $C_{29}H_{34}F_4N_4O_2$: C, 63.72; H, 6.27; N, 10.25. Found: C, 63.53; H, 6.05; N, 10.40.

Example 87

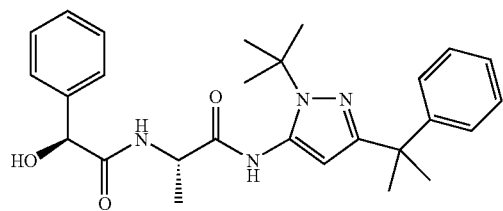

N-[2-tert-Butyl-5-(1-methyl-1-phenyl-ethyl)-2H-pyrazol-3-yl]-2-(2-hydroxy-2-phenyl-acetylamino)-propionamide MS 521 (M+Na)
Anal. Calcd for $C_{27}H_{32}F_2N_4O_3$: C, 65.05; H, 6.47; N, 11.24. Found: C, 64.80; H, 6.45; N, 10.88.

Example 88

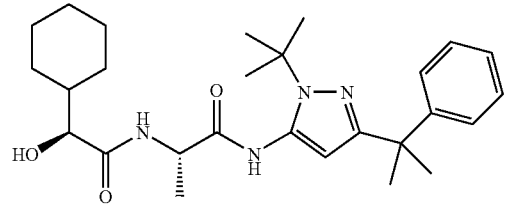

N-[2-tert-Butyl-5-(1-methyl-1-phenyl-ethyl)-2H-pyrazol-3-yl]-2-(2-cyclohexyl-2-hydroxy-acetylamino)-propionamide MS 469 (M+H), 491 (M+Na)
Anal. Calcd for $C_{27}H_{40}N_4O_3$: C, 69.20; H, 8.60; N, 11.96. Found: C, 68.77; H, 8.22; N, 12.04.

Example 88a

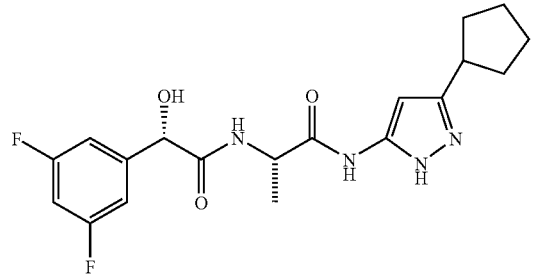

N-(5-Cyclopentyl-2H-pyrazol-3-yl)-2-[2-(3,5-difluoro-phenyl)2-2hydroxy-acetylamino]-propionamide MS 393 (M+H), MS 415 (M+Na).

Example 89

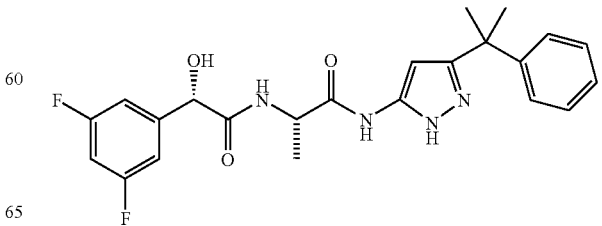

2-[2-(3,5-Difluorophenyl)-2-hydroxy-acetylamino]-
N-[5-(1-methyl-1-phenyl-ethyl)-2H-pyrazol-3-yl]-
propionamide MS 443 (M+H), MS 465 (M+Na).

Example 90

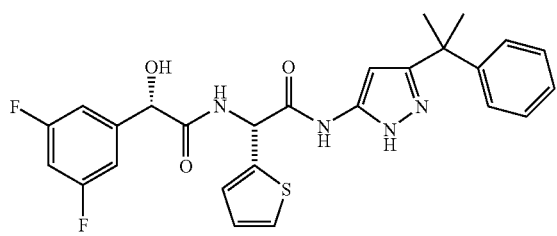

(S)-2-(3,5-difluorophenyl)-2-hydroxy-N—((R)-2-
oxo-2-(3-(2-phenylpropan-2-yl)-1H-pyrazol-5-
ylamino)-1-(thiophen-2-yl)ethyl)acetamide MS 511 (M+H), 533 (M+Na).

Example 91

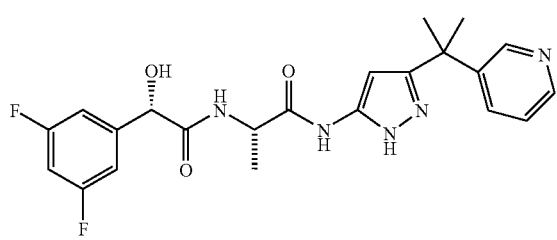

(S)-2-((S)-2-(3,5-difluorophenyl)-2-hydroxyacety-
lamino)-N-(3-(2-(pyridin-3-yl)propan-2-yl)-1H-
pyrazol-5-yl)propanamide

MS 444 (M+H).

Example 92

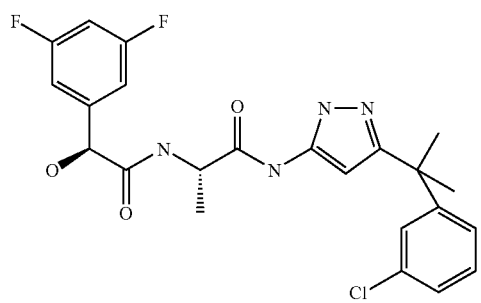

N-{5-[1-(3-Chloro-phenyl)-1-methyl-ethyl]-2H-
pyrazol-3-yl}-2-[2-(3,5-difluoro-phenyl)-2-hydroxy-
acetylamino]-propionamide

MS 477.1 (M+H)

Example 93

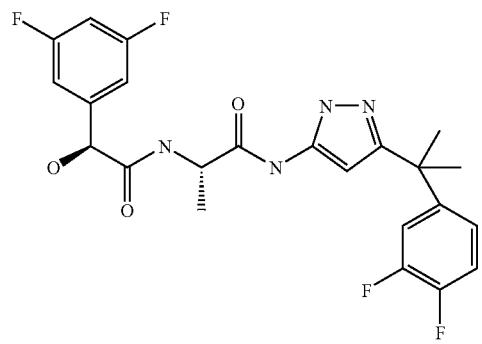

2-[2-(3,5-Difluoro-phenyl)-2-hydroxy-acetylamino]-
N-{5-[1-(3,4-difluoro-phenyl)-1-methyl-ethyl]-2H-
pyrazol-3-yl}-propionamide

MS 479.1 (M+H)

Example 94

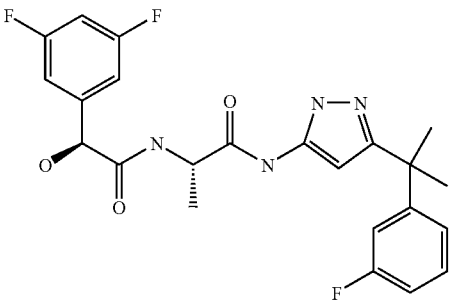

2-[2-(3,5-Difluoro-phenyl)-2-hydroxy-acetylamino]-
N-{5-[1-(3-fluoro-phenyl)-1-methyl ethyl]-2H-pyra-
zol-3-yl}-propionamide

MS 461.1 (M+H)

Example 95

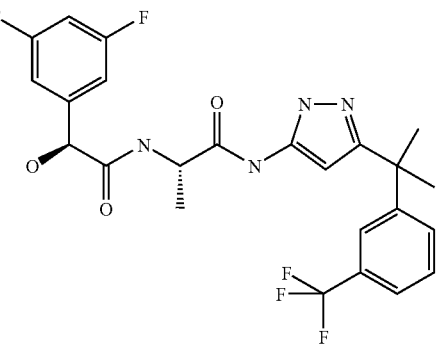

2-[2-(3,5-Difluoro-phenyl)-2-hydroxy-acetylamino]-N-{5-[1-methyl-1-(3-trifluoromethyl phenyl)-ethyl]-2H-pyrazol-3-yl}-propionamide

MS 511.1 (M+H)

Example 96

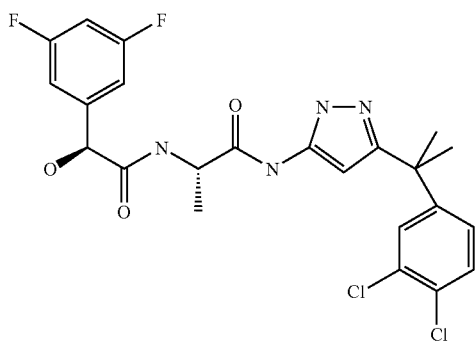

N-{5-[1-(3,4-Dichloro-phenyl)-1-methyl-ethyl]-2H-pyrazol-3-yl}-2-[2-(3,5-difluoro-phenyl)-2-hydroxy-acetylamino]-propionamide

MS 511.0 (M+H)

Example 97

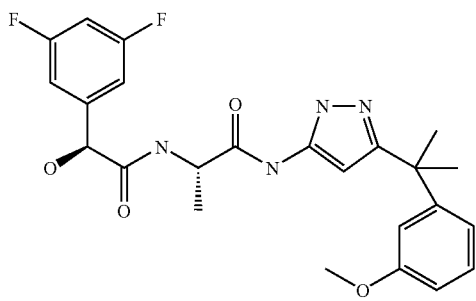

2-[2-(3,5-Difluoro-phenyl)-2-hydroxy-acetylamino]-N-{5-[1-(3-methoxy-phenyl)-1-methyl-ethyl]-2H-pyrazol-3-yl}-propionamide

MS 473.2 (M+H)

Example 98

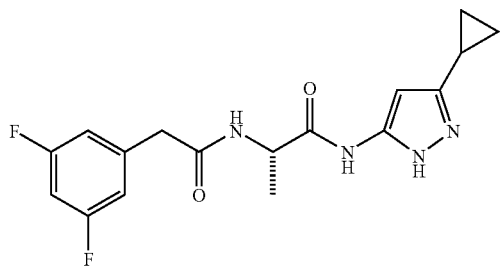

(2S)—N-(5-Cyclopropyl-2H-pyrazol-3-yl)-2-[2-(3,5-difluorophenyl)-acetylamino]-propionamide MS 349 (M+H), 371 (M+Na).

Example 99

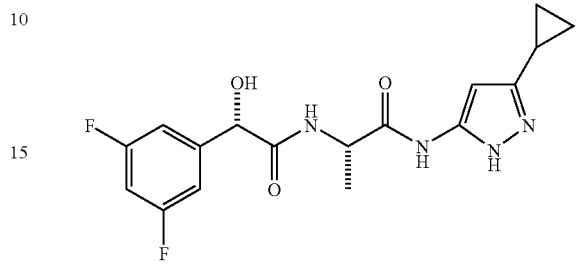

(2S,2'S)—N-(5-Cyclopropyl-2H-pyrazol-3-yl)-2-[2-(3,5-difluorophenyl)-2-hydroxy-acetylamino]-propionamide MS
$^1$H NMR (CDCl$_3$, 300 MHz) δ 12.11 (s, 1H), 8.02 (d, J=9.9 Hz, 1H), 7.16 (d, J=6.1 Hz, 2H), 6.79 (m, 1H), 6.20 (s, 1H), 5.18 (s, 1H), 4.80 (m, 1H), 1.75 (m, 1H), 1.41 (d, J=6.6 Hz, 3H), 0.94 (m, 2H), 0.68 (m, 2H).

Example 100

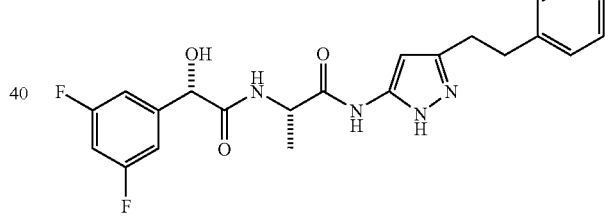

(2S,2'S)-2-[2-(3,5-Difluorophenyl)-2-hydroxyacetylamino]-N-(5-phenethyl-2H-pyrazol-3-yl)-propionamide MS 429 (M+H), 451 (M+Na).

Example 101

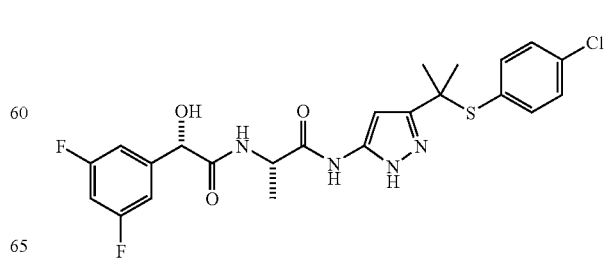

(2S,2'S)—N-{5-[1-(4-Chlorophenylsulfanyl)-1-methylethyl]-2H-pyrazol-3-yl}-2-[2-(3,5-difluorophenyl)-2-hydroxyacetylamino]-propionamide MS 509 (M+H), 531 (M+Na).
Anal Calcd for C$_{23}$H$_{23}$ClF$_2$N$_4$O$_3$S—H$_2$O: C, 52.42; H, 4.78; N, 10.63. Found: C, 52.55; H, 4.90; N, 10.40.

Example 102

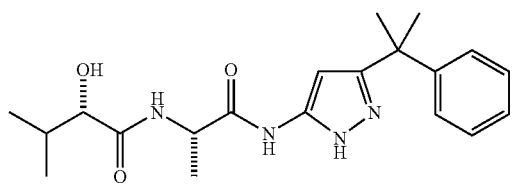

(2S,2'S)-2-Hydroxy-3-methyl-N-{1-[5-(1-methyl-1-phenylethyl)-2H-pyrazol-3-ylcarbamoyl]ethyl}-butyramide

MS 373 (M+H).

Example 103

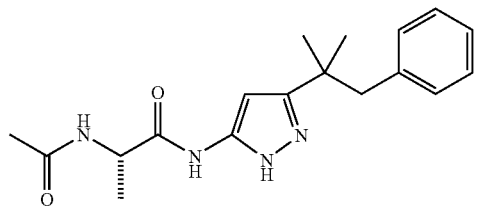

(2S)-2-Acetylamino-N-[5-(1,1-dimethyl-2-phenylethyl)-2H-pyrazol-3-yl]-propionamide MS 330 (M+H), 351 (M+Na).
$^1$H NMR (DMSO-d$_6$, 300 MHz) δ 12.07 (s, 1H), 10.23 (s, 1H), 8.05 (d, J=6.6 Hz, 1H), 7.15 (m, 3H), 6.88 (d, J=7.1 Hz, 2H), 6.17 (s, 1H), 4.36 (m, 1H), 2.83 (s, 2H), 1.81 (s, 3H), 1.19 (m, 9H).

Example 104

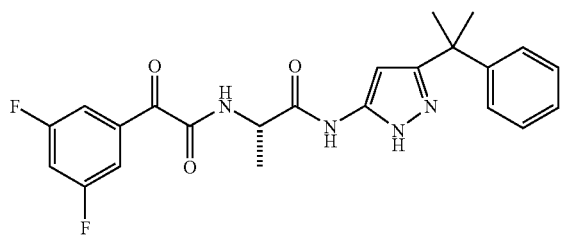

(2S)-2-[2'-(3,5-Difluorophenyl)-2'-oxo-acetylamino]-N-[5-(1-methyl-4-phenylethyl)-2H-pyrazol-3-yl]-propionamide MS 441 (M+H).
Anal Calcd for C$_{23}$H$_{22}$F$_2$N$_4$O$_3$: C, 62.72; H, 5.03; N, 12.72. Found: C, 62.36; H, 5.00; N, 12.41.
$^1$H NMR(CDCl$_3$, 300 MHz) δ 11.63 (s, 1H), 11.06 (s, 1H), 8.27 (d, J=9.3 Hz, 1H), 7.83 (m, 2H), 7.31-7.21 (m, 4H), 7.16-7.05 (m, 2H), 6.70 (s, 1H), 4.90 (m, 1H), 1.74 (s, 6H), 1.53 (d, J=7.1 Hz, 3H).

Example 105

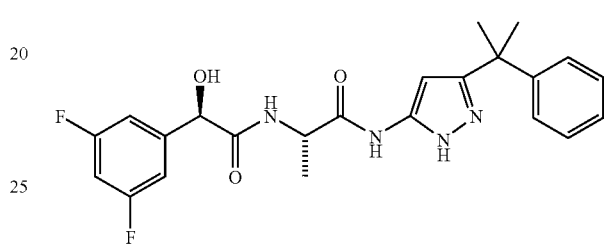

(2S,2'R)-2-[2'-(3,5-Difluorophenyl)-2'-hydroxyacetylamino]-N-[5-(1-methyl-1-phenylethyl)-2H-pyrazol-3-yl]-propionamide MS 443 (M+H), 465 (M+Na).
Anal Calcd for C$_{23}$H$_{24}$F$_2$N$_4$O$_3$.0.5H$_2$O: C, 61.19; H, 5.58; N, 12.41. Found: C, 61.72; H, 5.54; N, 12.34.

Example 106

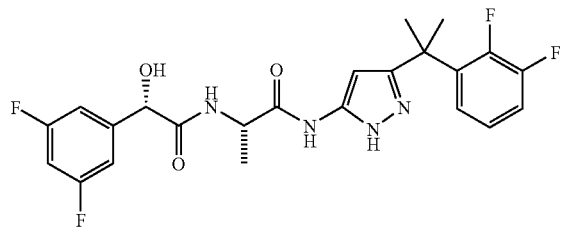

(2S,2'S)-2-[2'-(3,5-Difluorophenyl)-2'-hydroxyacetylamino]-N-[5-[1-2,3-difluorophenyl)-1-methylethyl]-2H-pyrazol-3-yl]-propionamide MS 479 (M+H), 501 (M+Na).
Anal Calcd for C$_{23}$H$_{22}$F$_4$N$_4$O$_3$.0.75H$_2$O: C, 56.15; H, 4.81; N, 11.39. Found: C, 56.23; H, 4.91; N, 11.01.

Example 107
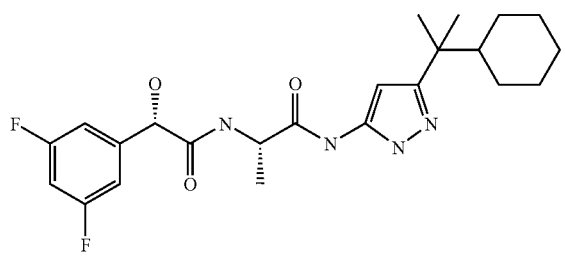
N-[5-(1-Cyclohexyl-1-methyl-ethyl)-2H-pyrazol-3-yl]-2-[2-(3,5-difluoro-phenyl)-2-hydroxy-acetylamino]-propionamide
MS 449.2 (M+H), 471.3 (M+Na).
$^1$H NMR (CD$_3$OD, 300 MHz) δ 7.09 (m, 2H), 6.87 (m, 1H), 6.32 (s, 1H), 5.08 (s, 1H), 1.40-1.80 (m, 5H), 1.41 (d, J=7.2 Hz, 3H), 1.24 (s, 6H), 0.90-1.35 (m, 6H).
$^{13}$C NMR (CD$_3$OD, 75 MHz) δ 175.1, 173.4, 165.4 (dd, J=12.3, 245.7 Hz), 155.1, 147.0 (t, J=9.5 Hz), 122.1, 111.5 (dd, J=8.3, 17.6 Hz), 104.8 (t, J=25.9 Hz), 96.8, 74.9, 51.1, 50.4, 39.3, 29.8, 28.9, 28.5, 25.8, 19.4.
Example 108
Synthesis of (2S,2'S)-2-[2'-(3,5-Difluorophenyl)-2'-hydroxyacetylamino]-N-[5-(1-methyl-4-phenylpiperidin-4-yl)-2H-pyrazol-3-yl]-propionamide
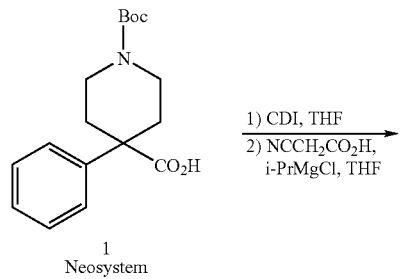
1
Neosystem
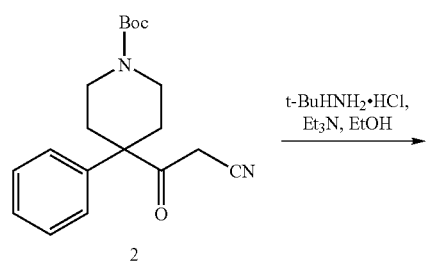
2
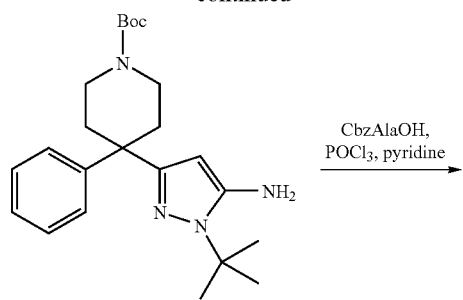
3
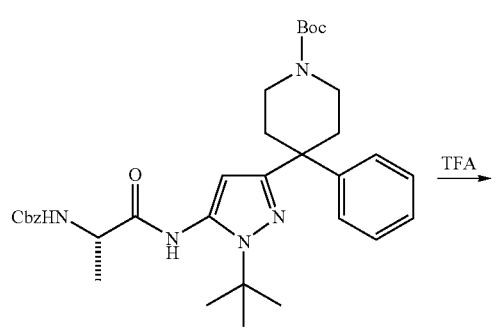
4
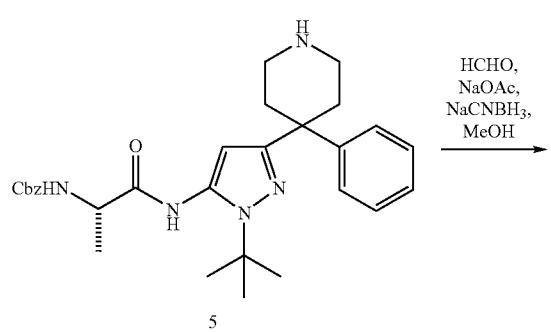
5
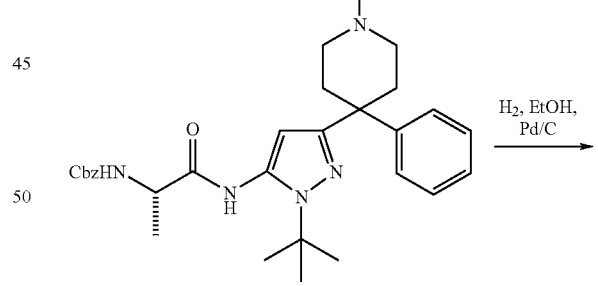
6
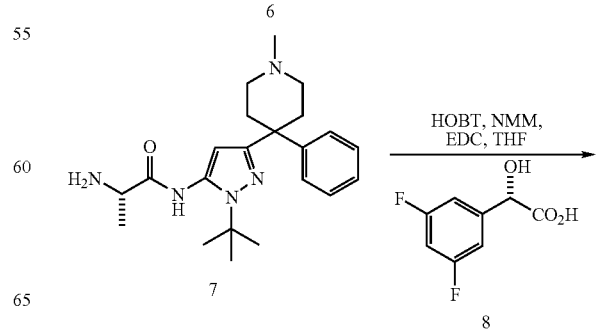
7                                    8

-continued

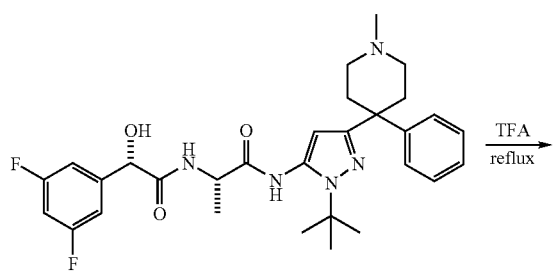

9

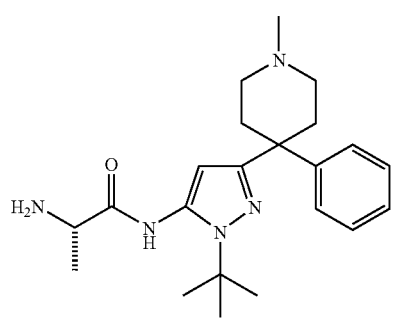

(2S)-2-Amino-N-[2-tert-butyl-5-(1-methyl-4-phenyl-piperidin-4-yl)-2H-pyrazol-3-yl]-propionamide (7)

A mixture of 0.36 g (0.7 mmol) of ester 6 and 0.36 g of 10% palladium on carbon in 5.0 mL of absolute EtOH was shaken under 30 psi of $H_2$. After 16 h, the mixture was filtered through Celite and 0.36 g of fresh 10% palladium on carbon was added to the filtrate. The mixture was again shaken under 30 psi of $H_2$ and this procedure was repeated until consumption of all starting material. The reaction mixture was filtered through Celite and the filtrate was concentrated by rotary evaporation. Purification of the material on silica gel using 4% $Et_3N$-MeOH as eluant afforded 0.14 g (51%) of amine 7 as clear, colorless oil.

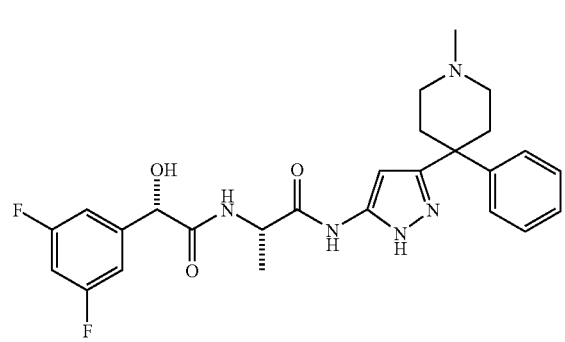

(2S,2'S)-2-[2'-(3,5-Difluorophenyl)-2'-hydroxyacetylamino]-N-[5-(1-methyl-4-phenylpiperidin-4-yl)-2H-pyrazol-3-yl]-propionamide

MS 498 (M+H).

Example 109

Synthesis of (2S,2'S)—N-[5-(1-Cyclopropyl-4-phenylpiperidin-4-yl)-2H-pyrazol-3-yl]-2-[2'-(3,5-difluorophenyl)-2'-hydroxylacetylamino]-propionamide

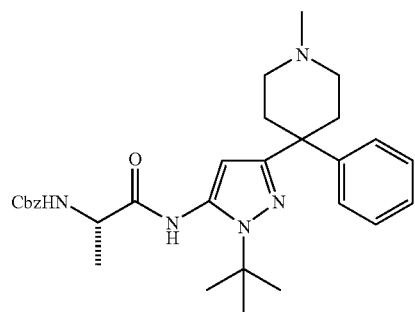

(2S)-1-[2-tert-Butyl-5-(1-methyl-4-phenylpiperidin-4-yl)-2H-pyrazol-3-ylcarbamoyl]-ethylcarbamic acid benzyl ester (6)

A solution of 0.67 g (1.3 mmol) of 5 in 10 mL of absolute MeOH was stirred at RT as 0.33 mL of a 37% aq. solution of formaldehyde was added followed by 0.33 g (4.0 mmol) of NaOAc and 0.27 g (4.3 mmol) of NaCNBH$_3$. After 16 h, the solvent was removed by rotary evaporation and the residue was extracted with water and EtOAc. The organic layer was dried over MgSO$_4$, filtered and the solvent was removed by rotary evaporation. Purification of the material on silica gel using 4% Et$_3$N-MeOH as eluant afforded 0.41 g (60%) of ester 6 as a clear, colorless glassy solid.

MS 518 (M+H).

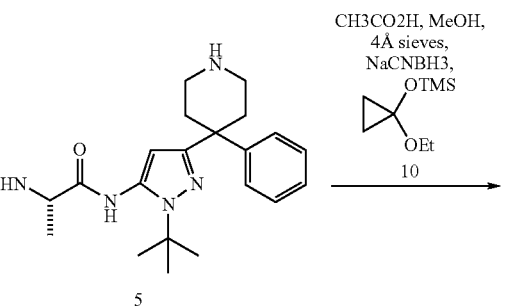

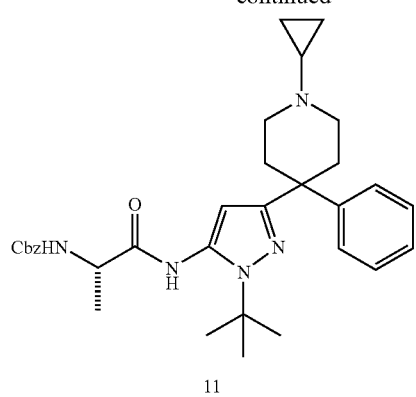

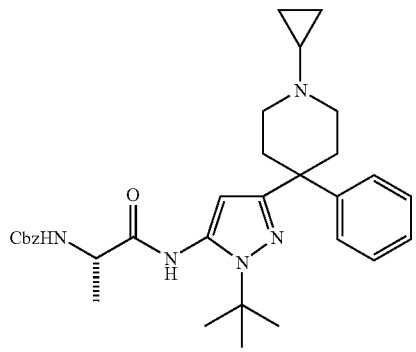

(S)-1-[2-tert-Butyl-5-(1-cyclopropyl-4-phenyl-piperidin-4-yl)-2H-pyrazol-3-ylcarbamoyl]-ethylcarbamic acid benzyl ester (11)

A solution of 1.22 g (2.4 mmol) of 5 in 20 mL of absolute MeOH was stirred at rt as 1.42 g (2.4 mmol) of conc. acetic acid, 1.28 g of 4 Å molecular sieves and 2.15 g (12.3 mmol) of ketal 10 were added followed by 0.68 g (10.8 mmol) of $NaCNBH_3$. The reaction mixture was refluxed for 16 h, cooled to RT, and filtered to remove solids. The filtrate was concentrated by rotary evaporation and extracted with water and EtOAc. The organic layer was dried over $MgSO_4$, filtered and the solvent was removed by rotary evaporation to afford 0.97 g (74%) of 11 as a clear, colorless, glassy solid.

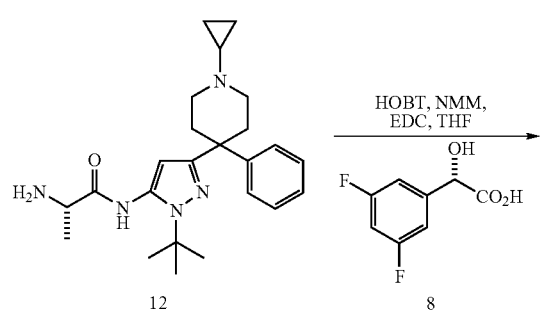

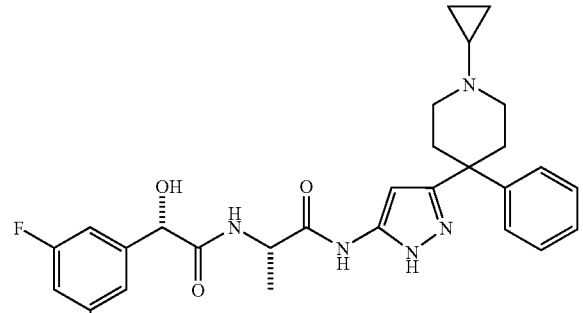

(2S,2'S)—N-[5-(1-Cyclopropyl-4-phenylpiperidin-4-yl)-2H-pyrazol-3-yl]-2-[2'-(3,5-difluorophenyl)-2'-hydroxylacetylamino]-propionamide MS 524 (M+H), 546 (M+Na).

Example 110

Synthesis of N-(5-tert-Butyl-2H-pyrazol-3-yl)-3-[(3,5-difluoro-phenyl)-formyl-amino]-benzamide

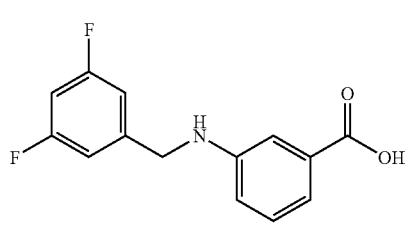

A solution of 4.0 mmoles (1.0 eq.) of 3,5-difluorobenzaldehyde and 4.0 mmole of 2-aminobenzoic acid in 60 mL of MeOH was prepared. While stirring at RT, 8.0 mmole (2.0 eq.) of NaOAc was added followed by 9.0 mmole of NaCNBH$_3$. The reaction solution was stirred at RT for 1.5 hr and rotary evaporated. The residue was taken up in 30 mL H$_2$O and 50 mL EtOAc. The layers were separated. The aqueous layer was extracted with EtOAc (2×50 mL). The combined organic layers were dried over Na$_2$SO$_4$ and vacuum filtered. The filtrate was rotary evaporated and dried under vacuum to give coupled product 5 (78%).

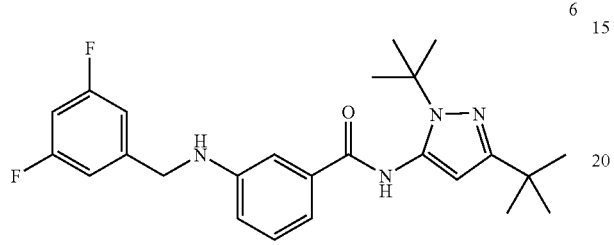

6

A solution of 3.1 mmoles (1.0 eq.) of 5 and 3.5 mmoles (1.1 eq.) of aminopyrazole in 10 mL of dry pyridine was cooled to −10° C. To the cooled solution, 3.4 mmoles (1.1 eq.) of POCl$_3$ was added. After stirring for 15 min, the orange reaction mixture was concentrated. The residue was taken up in 30 mL of H$_2$O, 20 mL of 2 M HCl, and 70 mL of EtOAc. The layers were separated and the aqueous layer was extracted with EtOAc (2×70 mL). The combined organic extracts were washed with saturated aqueous NaHCO$_3$, followed by drying over Na$_2$SO$_4$ and vacuum filtering. The filtrate was rotary evaporated. The crude product was flash chromatographed on silica using 20% EtOAc/hexanes as eluant to afford product 6 (25%).

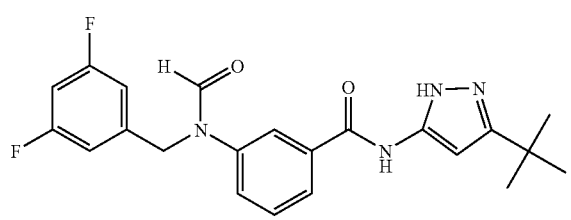

7

N-(5-tert-Butyl-2H-pyrazol-3-yl)-3-[(3,5-difluorophenyl)-formyl-amino]-benzamide A solution of 0.40 mmole of 6 was refluxed in 5 mL of formic acid for 15 min. After cooling to RT, the solution was added dropwise to saturated aqueous NaHCO$_3$. After ensuring pH 8, the solution was extracted with EtOAc (3×70 mL). The combined organic extracts were dried over Na$_2$SO$_4$ and vacuum filtered. The filtrate was rotary evaporated. The crude material was flash chromatographed on silica using 75% EtOAc/hexanes as eluant to afford product 7 (57%). This compound does not fall within general Formula I; however, it is a compound of interest because it inhibits β-amyloid peptide release and/or its synthesis. MS 413.2 (M+H), 435.2 (M+Na).

$^1$H NMR (CDCl$_3$, 300 MHz) δ 11.07 (s(br), 1H), 10.16 (s, 1H), 8.86 (s, 1H), 8.16 (s, 1H), 7.79 (d, J=7.7 Hz, 1H), 7.36 (m, 1H), 7.19 (m, 1H), 6.65 (m, 4H), 4.96 (s, 2H), 1.29 (s, 9H).

Example 111

N-(5-tert-Butyl-2H-pyrazol-3-yl)-3-(3,5-difluorophenylamino)-benzamide

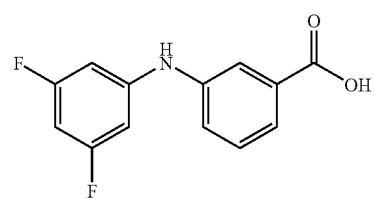

8

A suspension of 7.6 mmoles (1.0 eq.) of 2-aminobenzoic acid, 8.0 mmoles (1.1 eq.) of 3,5-difluorobromobenzene, 0.16 mmole (0.02 eq.) of Pd(OAc)$_2$, 0.16 mmole (0.02 eq.) of (S)-BINAP, and 31.8 mmoles (4.0 eq.) of sodium tert-butoxide in 20 mL of dry toluene was heated at 90° C. for 15.5 hrs. The mixture was cooled to RT and 40 mL of saturated aqueous NH$_4$Cl was added. The layers were separated and the aqueous layer was extracted with EtOAc (3×70 mL). The combined organic layers were dried over Na$_2$SO$_4$ and vacuum filtered. The filtrate was rotary evaporated. The crude material was flash chromatographed on silica with 75% EtOAc/hexanes as eluant to give coupled product 8 (15%).

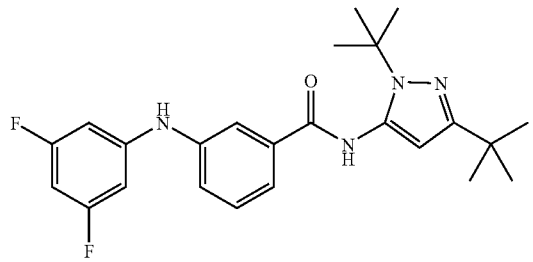

9

A solution of 1.4 mmoles (1.0 eq.) of 8 and 1.5 mmoles (1.1 eq.) of aminopyrazole in 5 mL of dry pyridine was cooled to −10° C. To the cooled solution, 1.5 mmoles (1.1 eq.) of POCl$_3$ was added. After stirring for 20 min, the orange reaction mixture was concentrated. The residue was taken up in 20 mL of H$_2$O, 10 mL of 2 M HCl, and 50 mL of EtOAc. The layers were separated and the aqueous layer was extracted with EtOAc (2×50 mL). The combined organic extracts were washed with saturated aqueous NaHCO$_3$ followed by drying over Na$_2$SO$_4$ and vacuum filtering. The filtrate was rotary evaporated. The crude product was flash chromatographed on silica using 20% EtOAc/hexanes as eluant to afford product 9 (30%).

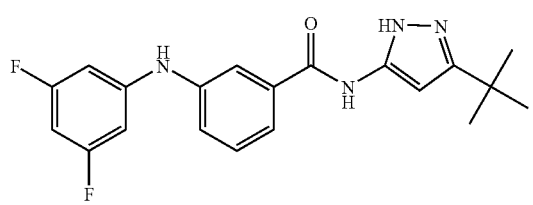

N-(5-tert-Butyl-2H-pyrazol-3-yl)-3-(3,5-difluorophenylamino)-benzamide

Hydrogen chloride gas was bubbled through a solution of 0.29 mmole of 9 in 15 mL of MeOH for 2 min. The reaction solution was refluxed for 5 hrs. The solution was rotary evaporated. The residue was dissolved in 40 mL of saturated aqueous NaHCO$_3$ and extracted with EtOAc (3×50 mL). The combined organic extracts were dried over Na$_2$SO$_4$ and vacuum filtered. The filtrate was rotary evaporated. The crude product was flash chromatographed on silica with a step gradient of 50% and 75% EtOAc/hexanes as eluants to afford product 91891 (12%). This compound does not fall within general Formula I, however, it also inhibits β-amyloid peptide release and/or its synthesis. $^1$H NMR (CD$_3$OD, 300 MHz) δ 7.71 (s(br), 1H), 7.55 (d, J=7.7 Hz, 1H), 7.46 (m, 1H), 7.37 (d, J=7.7 Hz, 1H), 6.67 (d, J=7.7 Hz, 2H), 6.47 (s, 1H), 6.38 (m, 1H), 1.38 (s, 9H).

Example 112

Synthesis of Product 14

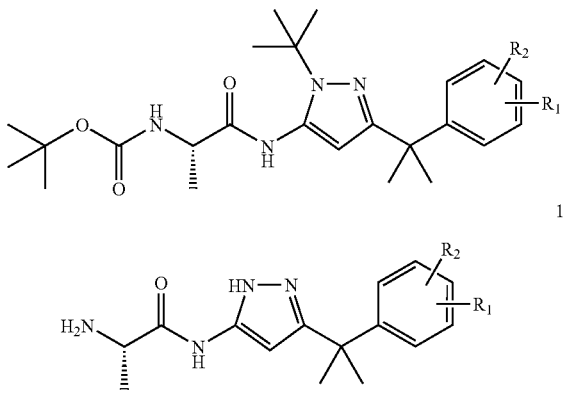

A solution of 1.2 mmole of 13 in 15 mL of TFA was refluxed overnight. After 17 hrs, the solution was cooled to RT and added dropwise to saturated aqueous NaHCO$_3$. After ensuring pH 8, the solution was extracted with EtOAc (3×70 mL). The combined organic extracts were dried over MgSO$_4$ and vacuum filtered. The filtrate was rotary evaporated and dried under vacuum to afford the product 14.

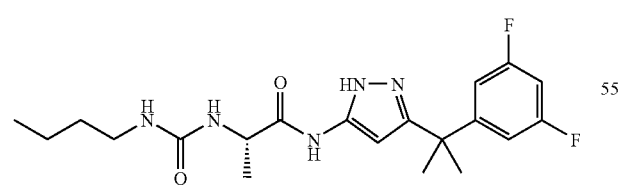

The n-butyl isocyanate intermediate was generated by treating 0.96 mmole (1.0 eq.) of 1-aminobutane with 1.9 mmole (2.0 eq.) of 1.93 M phosgene in toluene. The 1-aminobutane was dissolved in 5 mL of CH$_2$Cl$_2$ and 5 mL of saturated aqueous NaHCO$_3$ and cooled to 0° C. The phosgene was added to the methylene chloride layer and stirred vigorously for 10 min. The layers were separated. The organic layer was dried over MgSO$_4$ and vacuum filtered. The filtrate was rotary evaporated and dried under vacuum to afford n-butyl isocyanate.

In a separate flask, a solution of 0.95 mmole (1.0 eq.) of 14, 1.2 mmole (1.3 eq.) of Et$_3$N in 5 mL of THF was prepared. A solution of the n-butyl isocyanate in 2 mL of CH$_2$Cl$_2$ was added and stirred at rt for 35 min. The reaction mixture was rotary evaporated. The crude product was purified on a TLC preparatory plate using 7% MeOH/CH$_2$Cl$_2$ as eluant to give urea product 104228. MS 408.2 (M+H), 429.8 (M+Na). $^1$H NMR (CDCl$_3$, 300 MHz) δ 11.96 (s(br), 1H), 6.80 (d, J=7.1 Hz, 2H), 6.59 (m, 2H), 5.63 (d, J=8.2 Hz, 1H), 4.79 (m, 2H), 3.01 (m, 2H), 1.73 (s, 3H), 1.71 (s, 3H), 1.41 (d, J=7.1 Hz, 3H), 1.33 (m, 2H), 1.21 (m, 2H), 0.82 (t, J=7.1 Hz, 3H).

Example 113

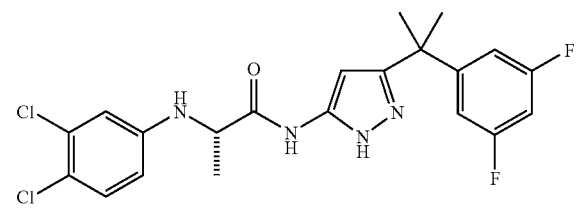

(2S)-2-(3,4-Dichlorophenylamino)-N-{5-[1-(3,5-difluorophenyl)-1-methylethyl]-2H-pyrazol-3-yl}-propionamide MS 453 (M+H).
Anal Calcd for C$_{21}$H$_{20}$Cl$_2$F$_2$N$_4$O.0.5H$_2$O: C, 54.56; H, 4.58; N, 12.12. Found: C, 54.76; H, 4.51; N, 11.83.

Example 114

Synthesis of 5-(2-[(3,5-Difluorophenyl)acetylamino]-2-(isopropylthio)acetylamino)-3-tert-butylpyrazole 18

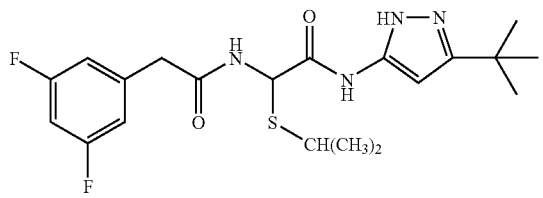

(3,5-Difluorophenyl)acetamide 1

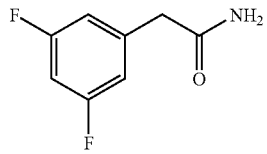

A solution of 10 g of (3,5-difluorophenyl)acetic acid in 100 mL of tetrahydrofuran was treated with 9.9 g of carbonyldiimidazole. The mixture was stirred at 25° C. for 3 hours then a vigorous stream of anhydrous ammonia was bubbled through the solution for 1 hour. The mixture was stirred for 2 days and then the solvent was evaporated at reduced pressure. The residue was suspended in 100 mL of distilled water. The mixture was filtered and the filtrant washed with distilled water twice. After drying in a stream of air, the (3,5-difluorophenyl)acetamide was obtained as 8.4 g of an ivory solid. $^1$H-NMR (DMSO-d$_6$): δ 7.51 (broad s, 1H), 7.15-6.85 (m, 3H), 3.40 (s, 2H). MS (EI): m/z 171. EA Calc'd for C—$_8$H$_7$NO: C, 56.13; H, 4.13; N, 8.18. Found: C, 56.16; H, 4.05; N, 8.07.

2-[(3,5-Difluorophenyl)acetylamino]-2-hydroxyacetic acid 2

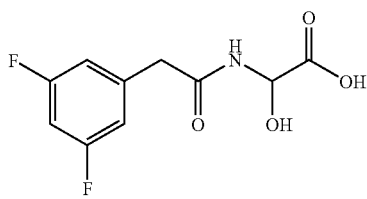

A mixture of 7.2 g of (3,5-difluorophenyl)acetamide 1 and 4.6 g of glyoxylic acid hydrate in 75 mL of acetone was refluxed 24 hours. The solvent was evaporated and the residue was dissolved in 300 mL of ethyl acetate. This solution washed with 150 mL of distilled water. The aqueous phase was discarded. The organic phase was extracted with a solution prepared by diluting 50 mL of a saturated aqueous solution of sodium bicarbonate with 150 mL of distilled water. The organic phase was discarded and the aqueous bicarbonate solution was acidified with 80 mL of 1 N aqueous sodium bisulfate solution. The acidified solution was extracted with three successive 125 mL portions of ethyl acetate. The combined organic extracts were washed with brine and then dried over magnesium sulfate. The solution was filtered and the solvent was evaporated to yield 2-[(3,5-difluorophenyl)acetylamino]-2-hydroxyacetic acid as 5.2 g of a white solid. $^1$H-NMR (DMSO-d$_6$): δ 8.95 (d, J=8 Hz, 1H), 7.15-6.90 (m, 3H), 5.37 (d, J=8 Hz, 1H), 3.50 (s, 2H). $^{13}$C-NMR (DMSO-d6$_6$) δ 171.5, 169.4, 162.4 (dd, J$_{C-F}$=13, 244 Hz), 140.6 (t, J$_{C-F}$=10 Hz), 112.6 (dd, J$_{C-F}$=8, 17 Hz), 71.5, 41.7. MS (CI+): m/z 246. EA Calc'd for C$_{10}$H$_9$F$_2$NO$_4$: C, 48.98; H, 3.71; N, 5.71. Found: C, 49.02; H, 3.72; N, 5.51.

Methyl 2-[(3,5-difluorophenyl)acetylamino]-2-methoxyacetate 2A

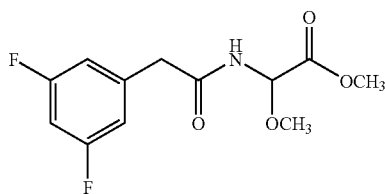

A 0° C. mixture of 1.0 g of 2-[(3,5-Difluorophenyl)acetylamino]-2-hydroxyacetic acid 2, 20 mL of methanol, and 6 mL of dichloromethane was treated with 0.3 mL of sulfuric acid. The mixture was stirred 2 days at 25° C. The solvent was evaporated at reduced pressure and the residue was partitioned between distilled water and ethyl acetate. The aqueous phase washed with ethyl acetate, and the combined organic extracts were washed successively with a saturated aqueous solution of sodium bicarbonate and brine. The solution was dried over magnesium sulfate and filtered. The solvent was evaporated at reduced pressure. The residue was chromatographed on silica gel eluting with 30% ethyl acetate in hexanes. Fractions containing the major component of the mixture were combined to yield methyl 2-[(3,5-difluorophenyl) acetylamino]-2-methoxyacetate 2A as 0.52 g of a white powder. $^1$H-NMR (DMSO-d$_6$): δ 9.15 (d, J=8.7 Hz, 1H), 7.15-6.85 (m, 3H), 5.34 (d, J=8.7 Hz, 1H), 3.69 (s, 3H), 3.60 (s, 3H), 3.24 (s, 2H)). $^{13}$C-NMR (CDCl$_3$) δ 169.9, 168.17, 163.0 (dd, J$_{C-F}$=12.8, 248 Hz), 137.4 (t, J$_{C-F}$=9 Hz), 112.2 (dd, J$_{C-F}$=8, 17 Hz), 102.9 (t, J$_{C-F}$=25 Hz), 78.3, 56.8, 52.8, 42.7. MS (CI+): m/z 274. EA Calc'd for C$_{12}$H$_{13}$F$_2$NO$_4$: C, 52.74; H, 4.81; N, 5.13. Found: C, 52.52; H, 4.87; N, 5.03.

2-[(3,5-Difluorophenyl)acetylamino]-2-methoxyacetic acid 3

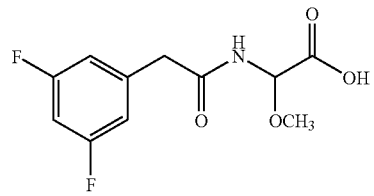

Methyl 2-[(3,5-difluorophenyl)acetylamino]-2-methoxyacetate 2A (0.4 g) was dissolved in 10 mL of dioxane and treated with 2.8 mL of a 1.0 N aqueous sodium hydroxide solution. After 1.5 h most of the solvent was removed by evaporation at reduced pressure. The mixture was acidified with an aqueous solution of sodium bisulfate and washed with two successive portions of ether. The combined organic extracts were washed with brine and then dried with magnesium sulfate. The solution was filtered and the solvent was evaporated at reduced pressure to yield 2-[(3,5-Difluorophenyl)acetylamino]-2-methoxyacetic acid 3 as 0.35 g of a white powder. $^1$H-NMR (DMSO-d$_6$): δ 9.06 (d, J=8.7 Hz, 1H), 7.15-6.85 (m, 3H), 5.23 (d, J=8.7 Hz, 1H), 3.57 (s, 3H), 3.21 (s, 2H).

5-Amino-1,3-di(tert-butyl)pyrazole (2363-46) 17

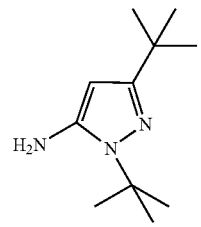

A mixture of 12.5 g of 4,4-dimethyl-3-oxopentanenitrile, 25 g of tert-butylhydrazine hydrochloride, and 27.6 g of potassium carbonate in 400 mL of ethanol was refluxed for 24 h. The mixture was cooled to 25° C. and then it was filtered. The solvent was evaporated from the filtrate and the residue was partitioned between ethyl acetate and distilled water. The organic phase washed with brine and dried (MgSO$_4$). The solvent was evaporated at reduced pressure and the residue was dissolved in a small volume of ether. The mixture was diluted with an equal volume of hexanes and then the volume of the solution was reduced by one half by evaporation at reduced pressure. The white solid which precipitated was collected by filtration to give 8.7 g of 5-Amino-1,3-di(tert-butyl)pyrazole 17. $^1$H-NMR (CDCl$_3$): δ 5.43 (s, 1H), 1.62 (s, 9H), 1.25 (s, 9H).

5-(2-[(3,5-Difluorophenyl)acetylamino]-2-(isopropylthio)acetylamino)-3-tert-butylpyrazole 18

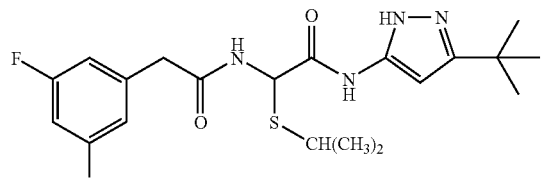

ED50 = 5 nM

Phosphorous oxychloride (0.1 mL) was added to a 0° C. solution of 0.3 g of acid 14 and 0.19 g of 5-amino-1,3-di-tert-butylpyrazole 17 in 5 mL of pyridine. After 20 min the reaction mixture was poured onto ice. The resulting suspension washed with ethyl acetate twice. The combined organic extracts were washed with distilled water, a 1 N aqueous solution of sodium bisulfate, and brine. The solution was dried (MgSO$_4$) and the solvent was evaporated at reduced pressure. The residue, which had solidified during the solvent evaporation step, was slurried with a small amount of ethyl acetate. The mixture was filtered and the solid thus obtained was dried in a stream of air to give 75 mg of a white solid.

A 59 mg sample of this material was suspended in formic acid. The reaction flask was then partially immersed in a preheated 115° C. oil bath. After 20 minutes at reflux the solution was cooled to 25° C. The formic acid was removed by evaporation at reduced pressure. After completely removing the formic acid the residue was dissolved in a few mL of chloroform and the resulting solution was filtered. The chloroform was evaporated from the filtrate and the residue suspended in tert-butyl methyl ether. The suspension was refluxed for 5 min and then it was cooled to 25° C. It was filtered and the solid thus obtained was dried in a stream of air. 5-(2-[(3,5-Difluorophenyl)acetylamino]-2-(isopropylthio) acetylamino)-3-tert-butylpyrazole 18 is obtained as 37 mg of a white powder.

$^1$H-NMR (CDCl$_3$): δ 7.06 (d, J=10 Hz, 1H), 6.9-6.7 (m, 3H), 6.54 (s, 1H), 5.99 (d, J=10 Hz, 1H), 3.62 (s, 2H), 3.1-3.1 (m, 1H), 1.31 (s, 9H), 1.27 (d, J=5.4 Hz, 3H), 1.23 (d, J=6.6 Hz, 3H)). $^{13}$C-NMR (DMSO-d$_6$) δ 172.4, 168.4, 164.9 (dd, $J_{C-F}$=13, 245 Hz), 156.0, 147.6, 141.3 (t, $J_{C-F}$=ca. 10 Hz), 113.7 (dd, $J_{C-F}$=7.7, 17 Hz), 103.6 (t, $J_{C-F}$=26 Hz), 94.7, 56.7, 43.2, 37.0, 32.6, 30.8, 27.6, 24.8, 24.6. MS (CI+): m/z 447 (M+Na$^+$). EA Calc'd for C$_{20}$H$_{26}$F$_2$N$_4$O$_2$S.1.7H$_2$O: C, 52.78; H, 6.51; N, 12.31. Found: C, 52.57; H, 6.16; N, 12.18.

Example 115

Synthesis of 5-(2-[(3,5-Difluorophenyl)acetylamino]-2-(2,2,2-(trifluoroethyl)thio)acetylamino)-3-tert-butylpyrazole 19

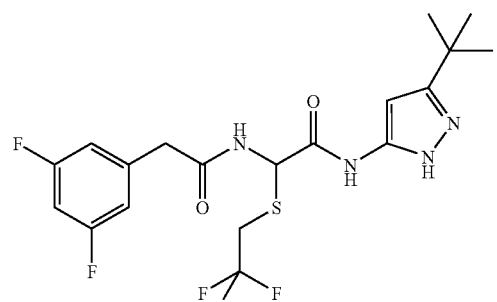

ED50 = 30 nM

This compound was prepared from the acid 2 (example 114) using a three step procedure analogous to that used for the preparation of 18 (Example 114). One difference is that the amide bond formation was performed using PhOP(O)Cl$_2$ in place of POCl$_3$. After this amide bond forming step, the intermediate was purified by filtration through silica gel eluting with 20% ethyl acetate in hexane. Compound 19 gave the following analytical data: 48.92% C, 4.59% H, 11.80% N.

Example 116

Synthesis of 5-(2-[(3,5-Difluorophenyl)acetylamino]-2-(ethoxyacetyl)amino-3-tert-butylpyrazole 20

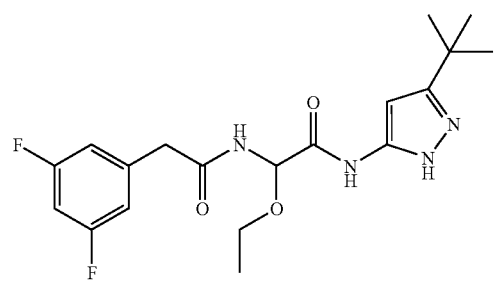

ED50 = 128 nM

A suspension of 0.4 grams of compound 18 (Example 114) in 20 mL of 1:1 dichloromethane/ethanol was treated with 0.375 grams of N-bromosuccinimide. After one hour the solution was treated with 1 mL of a saturated aqueous solution of sodium bisulfite. After an additional 5 min, the mixture was partitioned between water and ethyl acetate. The organic phase washed with brine and dried with magnesium sulfate. The solvent was evaporated at reduced pressure and the residue was recrystallized from aqueous methanol twice. The resulting solid was dissolved in 20 mL of ethanol and treated with 50 mg of 10% palladium on carbon and 300 mg of sodium acetate. The mixture was agitated under 50 psi hydrogen gas for 14 h. The mixture was filtered through celite and then the solvent was evaporated at reduced pressure. The residue was partitioned between water and ethyl acetate. The organic phase washed with brine and dried over magnesium sulfate. The solvent was evaporated at reduced pressure. The residue was recrystallized from a mixture of tert-butyl methyl ether and hexanes. The product was isolated as a white powder. Analysis gave 56.91% C, 6.11% H, and 14.20% N.

Example 117

Synthesis of 5-(2-[(3,5-Difluorophenyl)acetylamino]-2-(methylthio)acetylamino)-3-tert-butylpyrazole 21

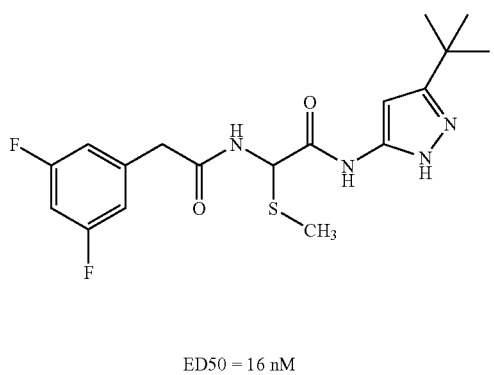

ED50 = 16 nM

This compound was prepared from the acid 11 (Example 114) using a three step procedure analogous to that used for the preparation of 18 from 14 (Example 114). Compound 21 gave the following mass spectral data: m/z=419.2 $(M+H)^+$.

Example 118

Monoethyl 2-(tert-butoxycarbonylamino)malonate 22

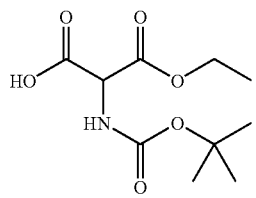

A commercial sample of diethyl 2-aminomalonate hydrochloride (7.0 g) was treated with 5.5 mL of triethylamine in a mixture of 50 mL of tetrahydrofuran and 30 mL of dimethylformamide. The resulting mixture was treated with 6.76 grams of di(tert-butyl)pyrocarbonate and stirred at 25° C. for 14 hours. The solvent was evaporated at reduced pressure and the residue was partitioned between ethyl acetate and water. The organic phase washed with a saturated aqueous solution of sodium bicarbonate, a 1 molar solution of sodium bisulfate and then with brine. It was dried over magnesium sulfate and then the solvent was evaporated at reduced pressure. The resulting oil was dissolved in a mixture of 25 mL of ethanol and 28 mL of acetone. The resulting solution was cooled to 0° C. and treated with 26 mL of a 1.0 N aqueous solution of sodium hydroxide. The mixture was allowed to warm to 25° C. and stirred 18 hours. The solvent was evaporated at reduced pressure and the residue was partitioned between ethyl acetate and water. The aqueous phase was acidified with aqueous sodium bisulfate solution and extracted with ethyl acetate. The organic phase was dried (MgSO$_4$) and the solvent was evaporated to give an oil. The properties of this compound were in good accord with those described previously (*Journal of Medicinal Chemistry* 1982, 397).

Example 119

Synthesis of 1,3-bis(tert-butyl)-5-[2-(3,5-difluorophenyl)acetylamino-2-(ethoxycarbonyl)acetylamino]pyrazole 23

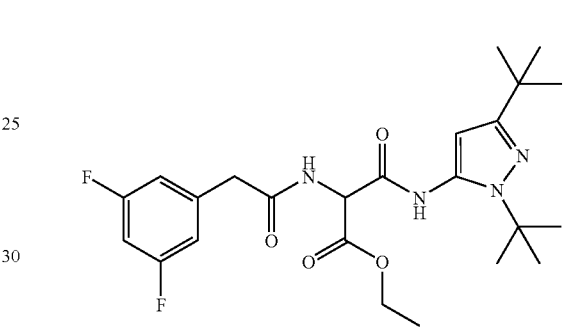

A mixture of 3.0 g of ester 22 (example 118) and 2.6 grams of aminopyrazole 17 (Example 114) in 50 mL of 0° C. pyridine was treated with 1.2 mL of phosphorus oxychloride. After 1 hour the mixture was poured into 250 mL of ice water. The mixture was filtered and the filtrant washed with water several times. The solid was dried in a stream of air to give an off white solid.

This material was dissolved in 100 mL of trifluoroacetic acid and stirred for 1.5 hours. The solvent was evaporated and the residue was partitioned between ethyl acetate and an excess of a saturated aqueous solution of sodium bicarbonate. The aqueous phase washed with ethyl acetate and the combined organic extracts were washed with brine and dried over magnesium sulfate. The solvent was evaporated at reduced pressure. The resulting oil was dissolved in a minimum volume of ethyl acetate and allowed to stand until seed crystals formed. The solvent was evaporated, and the residue was dissolved in a minimum volume of ether. The solution was diluted with a large excess of hexanes and the volume was reduced by evaporation at reduced pressure. The resulting solid was collected by filtration and washed with hexanes.

A solution of 1.0 gram of this solid, 0.43 g of N-methylmorpholine and 0.53 g of HOBt in 30 mL of dimethylformamide was treated with 0.75 grams of EDC hydrochloride. After 18 hours the mixture was partitioned between ethyl acetate and water. The aqueous phase was washed with water twice and the combined organic extracts were washed twice with water, once with a 1 N aqueous solution of sodium bisulfate, once with a saturated aqueous solution of sodium bicarbonate, and finally with brine. The solution was dried over magnesium sulfate and the solvent was evaporated at reduced pressure. Treating the residual oil with ether gave a solid precipitate, which was collected by filtration.

Example 120

Synthesis of 3-tert-butyl-5-[2-(3,5-difluorophenyl)acetylamino-2-(ethoxycarbonyl)acetylamino]pyrazole 24

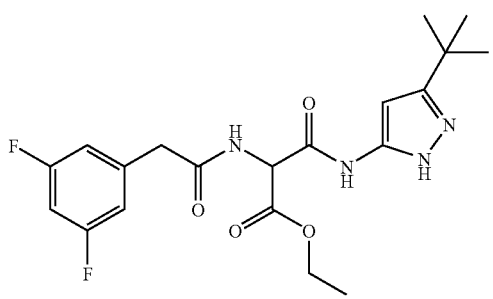

ED50 = 73 nM 250 mg of compound 23 (Example 119) was refluxed in 3 mL of formic acid for 20 min. The mixture was cooled to 25° C. and diluted with 12 mL of distilled water. The resulting precipitate was collected by filtration and dried in a stream of air. It was suspended in 5 mL of chloroform and filtered. The solvent was evaporated from the filtrate at reduced pressure. The residue was stirred with 5 mL of tert-butyl methyl ether for one hour, and then recovered by filtration. The product was obtained as a white powder. Analysis gave 56.84% C, 5.87% H, 13.28% N.

Example 121

Synthesis of 3-tert-butyl-5-[2-(3,5-difluorophenyl)acetylamino-2-(pyrrolidinocarbonyl)acetylamino]pyrazole 24

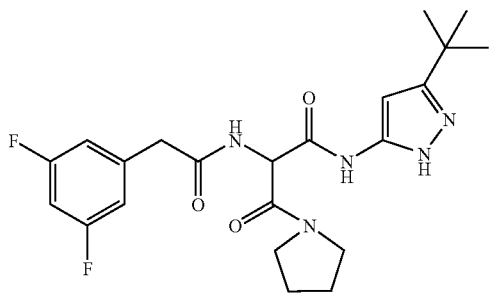

ED50 = 10,000 nM 0.7 grams of the ester 23 (Example 119) was dissolved in a mixture of 10 mL of ethanol and 10 mL of acetone. The resulting solution was treated with 2.46 mL of 1.0 N aqueous sodium hydroxide solution. After 48 hours the mixture was acidified with aqueous sodium bisulfate solution. It was partitioned between ethyl acetate and water. The aqueous phase washed with ethyl acetate and the combined organic extracts were washed with brine. The solution was dried over magnesium sulfate and the solvent was evaporated at reduced pressure to give an ivory solid.

A solution 0.3 g of this solid, 0.062 mL of pyrrolidine, and 0.19 gram of HOBt in 15 mL of DMF was treated with 0.14 grams of EDC hydrochloride. After 20 hours the mixture was partitioned between ethyl acetate and water. The aqueous phase washed with ethyl acetate and the combined organic extracts were washed with aqueous sodium bisulfate, pH 9 phosphate buffer, and brine. The solution was dried over magnesium sulfate and the solvent was evaporated to give a white powder.

This powder was refluxed in 1 mL of formic acid for 20 minutes. The solvent was evaporated in a stream of nitrogen. The residue was partitioned between ethyl acetate and water. The aqueous phase washed with ethyl acetate, and the combined organic extracts were washed with brine. The organic phase was dried over magnesium sulfate, and the solvent was evaporated at reduced pressure. The residual solid was briefly stirred with 1 mL of tert-butyl methyl ether and then filtered. This solid gave the following mass spectral data: m/z—448.2 $(M+H)^+$.

The following non-limiting formulation examples (Examples 122-131) illustrate representative pharmaceutical compositions of the present invention.

Example 122

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Example 123

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Example 124

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Example 125

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Example 126

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Example 127

Suppositories, each containing 25 mg of active ingredient are made as follows:

| Ingredient | Amount |
|---|---|
| Active Ingredient | 25 mg |
| Saturated fatty acid glyceride | 2,000 mg |

The active ingredient is passed through a No. 60 mesh U.S. sieve and suspended in the saturated fatty acid glycerides previously melted using the mini-mum heat necessary. The mixture is then poured into a suppository mold of nominal 2.0 g capacity and allowed to cool.

Example 128

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Example 129

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Example 130

A subcutaneous formulation may be prepared as follows:

| Ingredient | Quantity |
| --- | --- |
| Active Ingredient | 5.0 mg |
| Corn Oil | 1.0 mL |

Example 131

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin to | 100 g |

The white soft paraffin is heated until molten. The liquid paraffin and emulsifying wax are incorporated and stirred until dissolved. The active ingredient is added and stirring is continued until dispersed. The mixture is then cooled until solid.

Example 132

β-Amyloid Precursor Protein Accumulation Assay

An assay to evaluate the accumulation of Aβ is used to detect potential inhibitors of secretase. The assay uses the N 9 cell line, characterized for expression of exogenous APP by immunoblotting and immunoprecipitation.

The effect of test compounds on the accumulation of Aβ in the conditioned medium is tested by immunoprecipitation as described in WO 01/19797. Briefly, N 9 cells are grown to confluency in the 6-well plates. Test compounds dissolved in DMSO are added together with the addition of radiolabel. The cells are incubated for 4 h at 37° C. in a tissue culture incubator.

At the end of the incubation period, the conditioned medium is harvested and pre-cleared by the addition of normal mouse serum and of protein A Sepharose, mixed by end-over-end rotation for 30 minutes at 4° C., followed by a brief centrifugation in a microfuge. The supernatant is then harvested and transferred to fresh tubes containing of a monoclonal antibody directed against an internal peptide sequence in Aβ and protein A Sepharose. After incubation overnight at 4° C., the samples are washed. The pellet after the last wash is resuspended in SDS sample buffer and boiled for 3 minutes. The supernatant is then fractionated on SDS gels. The gels are dried and exposed to X-ray film or analyzed by phosphorimaging. The resulting image is analyzed for the presence of Aβ polypeptides. The steady-state level of Aβ in the presence of a test compound is compared to wells treated with DMSO (1%) alone. A typical test compound is considered active if it blocks Aβ accumulation in the conditioned medium, and has and $IC_{50}$ less than 100 μM.

Example 133

C-Terminus β-Amyloid Precursor Protein Accumulation Assay

The effect of test compounds on the accumulation of C-terminal fragments is determined by immunoprecipitation of APP and fragments thereof from cell lysates as described in WO 01/19797. N 9 cells are metabolically labeled as above in the presence or absence of test compounds. At the end of the incubation period, the conditioned medium are harvested and cells lysed in buffer. Lysates are precleared with normal rabbit serum and protein A-Sepharose, followed by the addition of BC-1 antiserum and protein A-Sepharose for 16 hours at 4° C. The immunoprecipitates are washed bound proteins eluted by boiling in SDS sample buffer and fractionated by Tris/Tricine SDS-PAGE. After exposure to X-ray film or phosphorimager, the resulting images are analyzed for the presence of C-terminal APP fragments. The steady-state level of C-terminal APP fragments is compared to wells treated with DMSO (1%) alone. A typical test compound is considered active if it stimulates C-terminal fragment accumulation in the cell lysates, and has an $IC_{50}$ less than

Example 134

Aβ Immunoprecipitation Assay

This immunoprecipitation assay as described in WO 01/19797 is specific for γ secretase (i.e., proteolytic activity required to generate the C-terminal end of Aβ either by direct cleavage or generating a C-terminal extended species which subsequently further proteolyzed). Briefly, N 9 cells are pulse-labeled in the presence of a reported γ secretase inhibitor for 1 h, followed by washing to remove the radiolabel and the inhibitor. The media is replaced and test compounds are added. Aβ is isolated from the conditioned medium and C-terminal fragments from cell lysates. The test compounds are characterized to determine whether a stabilization of C-terminal fragments is observed and whether Aβ is generated from these accumulated precursor. A typical test compound is considered active if it prevents the generation of Aβ out of accumulated C-terminal fragments and has an $IC_{50}$ less than 100 μM.

Example 135

Cellular Screen for the Detection of Inhibitors of β-Amyloid Production

Compounds of Formula I are assayed for their ability to inhibit β-amyloid peptide production in a cell line possessing the Swedish mutation. This screening assay employed cells (K293=human kidney cell line) which were stably transfected with the gene for amyloid precursor protein 751 (APP751) containing the double mutation $Lys_{651}$ $Met_{652}$ to $Asn_{651}$ $Leu_{652}$ (APP751 numbering) in the manner described in WO 94/10569 and Citron et al (*Nature*, 360:672-674 (1992)). This mutation is commonly called the Swedish mutation. The cells, designated as "293 751 SWE", are plated in Corning 96-well plates at $1.5\text{-}2.5\times10^4$ cells per well in Dulbecco's minimal essential media (Sigma, St. Louis, Mo.) plus 10% fetal bovine serum. Cell number is important in order to achieve β-amyloid ELISA results within the linear range of the assay (about 0.2 to 2.5 ng per mL).

Following overnight incubation at 37° C. in an incubator equilibrated with 10% carbon dioxide, media were removed and replaced with 200 μL of a compound of formula I (drug) containing media per well for a two hour pretreatment period and cells were incubated as above. Drug stocks were prepared in 100% dimethyl sulfoxide such that at the final drug concentration used in the treatment, the concentration of dimethyl sulfoxide did not exceed 0.5% and, in fact, usually equaled 0.1%.

At the end of the pretreatment period, the media are again removed and replaced with fresh drug containing media as above and cells are incubated for an additional two hours. After treatment, plates are centrifuged in a Beckman GPR at 1200 rpm for five minutes at room temperature to pellet cellular debris from the conditioned media. From each well, 100 μL of conditioned media or appropriate dilutions thereof are transferred into an ELISA plate precoated with antibody 266 (*Nature*, 359:325-327 (1992)) against amino acids 13-28 of β-amyloid peptide as described in WO 94/10569 and stored at 4° C. overnight. An ELISA assay employing labelled antibody 6C6 (*Nature*, 359:325-327 (1992)) against amino acids 1-16 of β-amyloid peptide is run the next day to measure the amount of β-amyloid peptide produced.

Cytotoxic effects of the compounds are measured by a modification of the method of Hansen, et al. (*J. Immun. Meth.*, 119:203-210 (1989)). To the cells remaining in the tissue culture plate is added 25 μL of a 3-(4,5-dimethylthiazol-2-yl)-2,5-diphenyltetrazolium bromide (MTT) (Sigma, St. Louis, Mo.) stock solution (5 mg/mL) to a final concentration of 1 mg/mL. Cells are incubated at 37° C. for one hour, and cellular activity was stopped by the addition of an equal volume of MTT lysis buffer (20% w/v sodium dodecylsulfate in 50% dimethylformamide, pH 4.7). Complete extraction is achieved by overnight shaking at room temperature. The difference in the $OD_{562}$ nm and the $OD_{650}$ mn is measured in a Molecular Device's $UV_{max}$ microplate reader as an indicator of the cellular viability.

The results of the β-amyloid peptide ELISA are fit to a standard curve and expressed as ng/mL β-amyloid peptide. In order to normalize for cytotoxicity, these results are divided by the MTT results and expressed as a percentage of the results from a drug free control.

Example 136

In Vivo Suppression of β-Amyloid Release and/or Synthesis

This example illustrates how the compounds of this invention could be tested for in vivo suppression of β-amyloid release and/or synthesis. For these experiments, 3 to 4 month old PDAPP mice are used (Games et al., Nature 373:523-52 (1995)). Depending upon which compound is being tested, the compound is usually formulated at either 5 or 10 mg/ml. Because of the low solubility factors of the compounds, they may be formulated with various vehicles, such as corn oil (Safeway, South San Francisco, Calif.); 10% EtOH in corn oil (Safeway); 2-hydroxypropyl-β-cyclodextrin (Research Biochemicals International, Natick Mass.); and carboxy-methyl-cellulose (Sigma Chemical Co., St. Louis, Mo.).

The mice are dosed subcutaneously with a 26 gauge needle and 3 hours later the animals are euthanized via $CO_2$ narcosis and blood is taken by cardiac puncture using a 1 cc 25G ⅝" tuberculin syringe/needle coated with solution of 0.5 M EDTA, pH 8.0. The blood is placed in a Becton-Dickinson vacutainer tube containing EDTA and spun down for 15 minutes at 1500×g at 5° C. The brains of the mice are then removed and the cortex and hippocampus are dissected out and placed on ice.

1. Brain Assay

To prepare hippocampal and cortical tissue for enzyme-linked immunosorbent assays (ELISAs) each brain region is homogenized in 10 volumes of ice cold guanidine buffer (5.0 M guanidine-HCl, 50 mM Tris-HCl, pH 8.0) using a Kontes motorized pestle (Fisher, Pittsburgh Pa.). The homogenates are gently rocked on a rotating platform for three to four hours at room temperature and stored at −20° C. prior to quantitation of β-amyloid.

The brain homogenates are diluted 1:10 with ice-cold casein buffer (0.25% casein, phosphate buffered saline (PBS), 0.05% sodium azide, 20 μg/ml aprotinin, 5 mM EDTA, pH 8.0, 10 .mu.g/ml leupeptin), thereby reducing the final concentration of guanidine to 0.5 M, before centrifugation at 16,000×g for 20 minutes at 4° C. The β-amyloid standards (1-40 or 1-42 amino acids) were prepared such that the final composition equaled 0.5 M guanidine in the presence of 0.1% bovine serum albumin (BSA).

The total β-amyloid sandwich ELISA, quantitating both β-amyloid (aa 1-40) and β-amyloid (aa 1-42) consists of two monoclonal antibodies (mAb) to β-amyloid. The capture antibody, 266, is specific to amino acids 13-28 of β-amyloid. The antibody 3D6, which is specific to amino acids 1-5 of β-amyloid, is biotinylated and served as the reporter antibody in the assay. The 3D6 biotinylation procedure employs the manufacturer's (Pierce, Rockford Ill.) protocol for NHS-biotin labeling of immunoglobulins except that 100 mM sodium bicarbonate, pH 8.5 buffer is used. The 3D6 antibody does not recognize secreted amyloid precursor protein (APP) or full-length APP but detects only β-amyloid species with an amino terminal aspartic acid. The assay has a lower limit of sensitivity of about 50 pg/ml (11 pM) and shows no cross-reactivity to the endogenous murine .beta.-amyloid peptide at concentrations up to 1 ng/ml.

The configuration of the sandwich ELISA quantitating the level of β-amyloid (aa 1-42) employs the mAb 21F12 (which recognizes amino acids 33-42 of β-amyloid) as the capture antibody. Biotinylated 3D6 is also the reporter antibody in this assay which has a lower limit of sensitivity of about 125 pg/ml (28 pM).

The 266 and 21F12 capture mAbs are coated at 10 μg/ml into 96 well immunoassay plates (Costar, Cambridge Mass.) overnight at room temperature. The plates are then aspirated and blocked with 0.25% human serum albumin in PBS buffer for at least 1 hour at room temperature, then stored desiccated at 4° C. until use. The plates are rehydrated with wash buffer (Tris-buffered saline, 0.05% Tween 20) prior to use. The samples and standards are added to the plates and incubated overnight at 4° C. The plates are washed three times with wash buffer between each step of the assay. The biotinylated 3D6, diluted to 0.5 μg/ml in casein incubation buffer (0.25% casein, PBS, 0.05% Tween 20, pH 7.4) is incubated in the well for 1 hour at room temperature. Avidin-HRP (Vector, Burlingame Calif.) diluted 1:4000 in casein incubation buffer is added to the wells for 1 hour at room temperature. The colorimetric substrate, Slow TMB-ELISA (Pierce, Cambridge, Mass.), is added and allowed to react for 15 minutes, after which the enzymatic reaction is stopped with addition of 2 N $H_2SO_4$. Reaction product is quantified using a Molecular Devices Vmax (Molecular Devices, Santa Clara, Calif.) measuring the difference in absorbance at 450 nm and 650 nm n.

2. Blood Assay

The EDTA plasma is diluted 1:1 in specimen diluent (0.2 gm/l sodium phosphate.H$_2$O (monobasic), 2.16 gm/l sodium phosphate.7H$_2$O (dibasic), 0.5 gm/l thimerosal, 8.5 gm/l sodium chloride, 0.5 ml Triton X-405, 6.0 g/l globulin-free bovine serum albumin; and water). The samples and standards in specimen diluent are assayed using the total β-amyloid assay (266 capture/3D6 reporter) described above for the brain assay except the specimen diluent is used instead of the casein diluents described.

Although the invention has been described with reference to the presently preferred embodiments, it should be understood that various modifications can be made without departing from the scope of the invention.

What is claimed is:

1. A compound of Formula II:

[Formula II structure]

wherein R$_1$ is aryl, or substituted aryl; X' is H or OH; R$_2$ is CH$_3$, R$_3$ is H, or t-butyl; R$_7$ is aryl, substituted aryl, or U-aryl, wherein U is O or CH$_2$; and R$_8$ and R$_9$ are independently H, or alkyl.

2. The compound of claim 1, wherein R$_3$ is H.

3. A pharmaceutical formulation comprising the compound according to claim 1 and a pharmaceutically acceptable carrier.

4. The compound of claim 1, wherein R$_1$ is 3,5-difluorophenyl.

5. A compound of Formula II:

[Formula II structure]

wherein R$_1$ is aryl or heteroaryl, cycloalkyl, or heterocycle, optionally substituted with one or more of —F, —Br, —OH, —CF$_3$, C$_{1-6}$ alkyl; C$_{1-3}$ alkoxy and methylenedioxy, X' is H or —OH; R$_3$ is H, or t-butyl; R$_7$ is aryl or U-aryl optionally substituted with one or more groups consisting of C$_{1-6}$ alkyl, chloro, fluoro, bromo, —NO$_2$, C$_{1-3}$ alkoxy, —CF$_3$, —N(R$_{7a}$)$_2$, C(O)R$_{7a}$—C(O)N(R$_{7a}$)$_2$, and —NHC(O)R$_{7a}$, wherein each R$_{7a}$ is independently chosen from H and C$_{1-6}$alkyl, U is O, —CH$_2$— or S; and R$_8$ and R$_9$ are each independently C$_{1-6}$ alkyl.

6. The compound of claim 5, wherein R$_3$ is H and R$_8$ and R$_9$ are both methyl.

7. The compound of claim 5, wherein R$_1$ is 3,5-difluorophenyl and X' is hydroxyl.

8. The compound of claim 5, wherein R$_3$ is H, R$_1$ is 3,5-difluorophenyl and X' is hydroxyl.

9. The compound of claim 5, wherein R$_7$ is aryl optionally substituted with one or more groups consisting of C$_{1-6}$ alkyl, chloro, fluoro, bromo, —NO$_2$, C$_{1-3}$ alkoxy, —CF$_3$, —N(R$_{7a}$)$_2$, C(O)R$_{7a}$ and —C(O)N(R$_{7a}$)$_2$, —NHC(O)R$_{7a}$, wherein each R$_{7a}$ is independently chosen from H and C$_{1-6}$ alkyl.

10. The compound of claim 1 chosen from the group consisting of: N-{5-[1-(4-chloro-phenyl)-1-methyl-ethyl]-2H-pyrazol-3-yl}-2-[2-(3,5-difluoro-phenyl)-2-hydroxy-acetylamino]-propionamide and, N-{5-[1-(4-nitro-phenyl)-1-methyl-ethyl]-2H-pyrazol-3-yl}-2-[2-(3,5-difluoro-phenyl)-2-hydroxy-acetylamino]-propionamide, N-{5-[1-(4-Amino-phenyl)-1-methyl-ethyl]-2H-pyrazol-3-yl}-2-[2-(3,5-difluoro-phenyl)-2-hydroxy-acetylamino]-propionamide, N-{5-[1-(4-Acetylamino-phenyl)-1-methyl-ethyl]-2H-pyrazol-3-yl}-2-[2-(3,5-difluoro-phenyl)-2-hydroxy-acetylamino]-propionamide, 2-[2-(3,5-Difluoro-phenyl)-2-hydroxy-acetylamino]-N-[5-(1-phenyl-ethyl)-2H-pyrazol-3-yl]-propionamide, 2-[2-(3,5-Difluoro-phenyl)-2-hydroxy-acetylamino]-N-{5-[1-(2-fluoro-phenyl)-1-methyl-ethyl]-2H-pyrazol-3-yl}-propionamide, 2-[2-(3,5-Difluoro-phenyl)-2-hydroxy-acetylamino]-N-{5-[1-(3,5-dimethyl-phenyl)-1-methyl-ethyl]-2H-pyrazol-3-yl}-propionamide, 2-[2-(3,5-Difluoro-phenyl)-2-hydroxy-acetylamino]-N-{5-[1-(2,4-difluoro-phenyl)-1-methyl-ethyl]-2H-pyrazol-3-yl}-propionamide, 2-[2-(3,5-Difluoro-phenyl)-2-hydroxy-acetylamino]-N-{5-[1-(4-trifluoromethyl-phenyl)-1-methyl-ethyl]-2H-pyrazol-3-yl}-propionamide, 2-[2-(3,5-Difluoro-phenyl)-2-hydroxy-acetylamino]-N-{5-[1-(4-dimethylamino-phenyl)-1-methyl-ethyl]-2H-pyrazol-3-yl}-propionamide, 2-[2-(3,5-Difluoro-phenyl)-2(S)-hydroxy-acetylamino]-N-[5-(1,1-dimethyl-2-phenyl-ethyl)-2H-pyrazol-3-yl]-propionamide, 2-[2-(3,5-Difluoro-phenyl)-2(R)-hydroxy-acetylamino]-N-[5-(1,1-dimethyl-2-phenyl-ethyl)-2H-pyrazol-3-yl]-propionamide, 2-[2-(3,5-Difluoro-phenyl)-2-hydroxy-acetylamino]-N-{5-[1-(3,5-difluoro-phenyl)-1-methyl-ethyl]-2H-pyrazol-3-yl}-propionamide, 2-Chloro-N-(1-{5-[1-(3,5-difluoro-phenyl)-1-methyl-ethyl]-2H-pyrazol-3-ylcarbamoyl}-ethyl)-benzamide, N-(1-{5-[1-(3,5-Difluoro-phenyl)-1-methyl-ethyl]-2H-pyrazol-3-ylcarbamoyl}-ethyl)-2-trifluoromethyl-benzamide, N-{5-[1-(3,5-Difluoro-phenyl)-1-methyl-ethyl]-2H-pyrazol-3-yl}-2-[2-hydroxy-2-(2-trifluoromethyl-phenyl)-acetylamino]-propionamide, 2-[2-(4-tert-Butyl-phenyl)-2-hydroxy-acetylamino]-N-{5-[1-(3,5-difluoro-phenyl)-1-methyl-ethyl]-2H-pyrazol-3-yl}-propionamide, 2-[2-(4-tert-Butyl-phenyl)-2-hydroxy-acetylamino]-N-{5-[1-(3,5-difluoro-phenyl)-1-methyl-ethyl]-2H-pyrazol-3-yl}-propionamide, 2-[2-(3-Chloro-phenyl)-2-hydroxy-acetylamino]-N-{5-[1-(3,5-difluoro-phenyl)-1-methyl-ethyl]-2H-pyrazol-3-yl}-propionamide, N-{5-[1-(3,5-Difluoro-phenyl)-1-methyl-ethyl]-2H-pyrazol-3-yl}-2-(2-hydroxy-2-p-tolyl-acetylamino)-propionamide, 2-[2-(4-Chloro-phenyl)-2-hydroxy-acetylamino]-N-{5-[1-(3,5-difluoro-phenyl)-1-methyl-ethyl]-2H-pyrazol-3-yl}-propionamide, N-{5-[1-(3,5-Difluoro-phenyl)-1-methyl-ethyl]-2H-pyrazol-3-yl}-2-[2-hydroxy-2-(4-methoxy-phenyl)-acetylamino]-propionamide, N-{5-[1-(3,5-Difluoro-phenyl)-1-methyl-ethyl]-2H-pyrazol-3-yl}-2-[2-hydroxy-2-(4-trifluoromethyl-phenyl)-acetylamino]-propionamide, 2-[2-(2-Chloro-phenyl)-2-hydroxy-acetylamino]-N-{5-[1-(3,5-difluoro-phenyl)-1-methyl-ethyl]-2H-pyrazol-3-yl}-propionamide, N-{2-tert-Butyl-5-[1-(4-fluoro-phenyl)-1-methyl-ethyl]-2H-pyrazol-3-yl}-2-[2-(3,5-difluoro-phenyl)-2-hydroxy-acetylamino]-propionamide, N-{2-tert-Butyl-5-[1-(3,5-difluoro-phenyl)-1-methyl-ethyl]-2H-pyrazol-3-yl}-2-[2-(3,5-difluoro-phenyl)-2-hydroxy-acetylamino]-propionamide, N-[2-tert-Butyl-5-(1,1-dimethyl-2-phenyl-ethyl)-2H-pyrazol-3-yl]-2-[2-(3,5-difluoro-phenyl)-2-hydroxy-acetylamino]-propionamide, N-[2-tert-Butyl-5-(1,1-dimethyl-2-phenyl-ethyl)-2H-pyrazol-3-yl]-2-[2-(3,5-difluoro-phenyl)-2-hydroxy-acetylamino]-propionamide, N-[2-tert-Butyl-5-(1,1-dimethyl-2-phenyl-ethyl)-2H-pyrazol-3-yl]-2-phenylacetylamino-propionamide, N-(1-{2-tert-Butyl-5-[1-(3,5-difluoro-phenyl)-1-methyl-ethyl]-2H-pyrazol-3-ylcarbamoyl}-ethyl)-3-trifluoromethyl-benzamide, N-{2-tert-Butyl-5-[1-(3,5-difluoro-phenyl)-1-methyl-ethyl]-2H-pyrazol-3-yl}-2-[2-(4-tert-butyl-phenyl)-2-hydroxy-acetylamino]-propionamide, N-{2-tert-Butyl-5-[1-(3,5-difluoro-phenyl)-1-methyl-ethyl]-2H-pyrazol-3-yl}-2-[2-(3-chloro-phenyl)-2-hydroxy-acetylamino]-propionamide, N-{5-[1-(3,5-Difluoro-phenyl)-1-methyl-ethyl]-2H-pyrazol-3-yl}-2-[2-(4-fluoro-phenyl)-2-hydroxy-acetylamino]-propionamide, N-{5-[1-(3,5-Difluoro-phenyl)-1-methyl-ethyl]-2H-pyrazol-3-yl}-2-(2-hydroxy-2-phenyl-acetylamino)-propionamide, 2-(2-Hydroxy-2-phenyl-acetylamino)-N-[5-(1-methyl-1-phenyl-ethyl)-2H-pyrazol-3-yl]-propionamide, 2-[(3,5-Difluoro-phenyl)-acetylamino]-N-{5-[1-(3,5-difluoro-phenyl)-1-methyl-ethyl]-2H-pyrazol-3-yl}-propionamide, (2-Benzo[1,3]dioxol-5-yl-acetylamino)-N-{5-[1-(3,5-difluoro-phenyl)-1-methyl-ethyl]-2H-pyrazol-3-yl}-propionamide, 2-[2-(4-Chloro-phenyl)-2-hydroxy-acetylamino]-N-[5-(1-methyl-1-phenyl-ethyl)-2H-pyrazol-3-yl]-propionamide, 2-[2-(2,3-Difluoro-phenyl)-2-hydroxy-acetylamino]-N-{5-[1-(3,5-difluoro-phenyl)-1-methyl-ethyl]-2H-pyrazol-3-yl}-propionamide, 2-[2-(3,5-Dimethoxy-phenyl)-acetylamino]-N-[5-(1-methyl-1-phenyl-ethyl)-2H-pyrazol-3-yl]-propionamide, 2-[2-(3,5-Bis-trifluoromethyl-phenyl)-acetylamino]-N-[5-(1-methyl-1-phenyl-ethyl)-2H-pyrazol-3-yl]-propionamide, 2-(2-Benzo[1,3]dioxol-5-yl-acetylamino)-N-{2-tert-butyl-5-[1-(3,5-difluoro-phenyl)-1-methyl-ethyl]-2H-pyrazol-3-yl}-propionamide, N-[2-tert-Butyl-5-(1-methyl-1-phenyl-ethyl)-2H-pyrazol-3-yl]-2-[2-hydroxy-2-(4-trifluoromethyl-phenyl)-acetylamino]-propionamide, N-{2-tert-Butyl-5-[1-(3,5-difluoro-phenyl)-1-methyl-ethyl]-2H-pyrazol-3-yl}-2-[2-(3,5-difluoro-phenyl)-acetylamino]-propionamide, N-[2-tert-Butyl-5-(1-methyl-1-phenyl-ethyl)-2H-pyrazol-3-yl]-2-[2-(4-chloro-phenyl)-2-hydroxy-acetylamino]-propionamide, N-{2-tert-Butyl-5-[1-(3,5-difluoro-phenyl)-1-methyl-ethyl]-2H-pyrazol-3-yl}-2-[2-(2,3-difluoro-phenyl)-2-hydroxy-acetylamino]-propionamide, N-{2-tert-Butyl-5-[1-(3,5-difluoro-phenyl)-1-methyl-ethyl]-2H-pyrazol-3-yl}-2-(2-hydroxy-2-phenyl-acetylamino)-propionamide N-[2-tert-Butyl-5-(1-methyl-1-phenyl-ethyl)-2H-pyrazol-3-yl]-2-(2-hydroxy-2-phenyl-acetylamino)-propionamide, 2-[2-(3,5-Difluorophenyl)-2-hydroxy-acetylamino]-N-[5-(1-methyl-1-phenyl-ethyl)-2H-pyrazol-3-yl]-propionamide, N-{5-[1-(3-Chloro-phenyl)-1-methyl-ethyl]-2H-pyrazol-3-yl}-2-[2-(3,5-difluoro-phenyl)-2-hydroxy-acetylamino]-propionamide, 2-[2-(3,5-Difluoro-phenyl)-2-hydroxy-acetylamino]-N-{5-[1-(3,4-difluoro-phenyl)-1-methyl-ethyl]-2H-pyrazol-3-yl}-propionamide, 2-[2-(3,5-Difluoro-phenyl)-2-hydroxy-acetylamino]-N-{5-[1-(3-fluoro-phenyl)-1-methyl-ethyl]-2H-pyrazol-3-yl}-propionamide2-[2-(3,5-Difluoro-phenyl)-2-hydroxy-acetylamino]-N-{5-[1-methyl-1-(3-trifluoromethyl-phenyl)-ethyl]-2H-pyrazol-3-yl}-propionamide, N-{5-[1-(3,4-Dichloro-phenyl)-1-methyl-ethyl]-2H-pyrazol-3-yl}-2-[2-(3,5-difluoro-phenyl)-2-hydroxy-acetylamino]-propionamide, 2-[2-(3,5-Difluoro-phenyl)-2-hydroxy-acetylamino]-N-{5-[1-(3-methoxy-phenyl)-1-methyl-ethyl]-2H-pyrazol-3-yl}-propionamide, 2-[2-(3,5-Difluoro-phenyl)-2-hydroxy-acetylamino]-N-[5-(1-methyl-1-phenylethyl)-2H-pyrazol-3-yl]-propionamide, 2-[2-(3,5-Difluorophenyl)-2-hydroxyacetylamino]-N-[5-[1-2,3-difluorophenyl]-1-methylethyl]-2H-pyrazol-3-yl]-propionamide.

* * * * *